US009775723B2

(12) United States Patent
Boyd et al.

(10) Patent No.: US 9,775,723 B2
(45) Date of Patent: Oct. 3, 2017

(54) INSTRUMENT AND SYSTEM FOR PLACING GRAFT, IMPLANT AND GRAFT MATERIAL FOR MINIMALLY INVASIVE POSTEROLATERAL FUSION

(71) Applicant: SPINE WAVE, INC., Shelton, CT (US)

(72) Inventors: Lawrence M. Boyd, Durham, NC (US); John J. Ratcliffe, Jr., Wendell, NC (US); Tim E. Adamson, Charlotte, NC (US); Paul J. Grata, Miramar, FL (US)

(73) Assignee: SPINE WAVE, INC., Shelton, CT (US)

( * ) Notice: Subject to any disclaimer, the term of this patent is extended or adjusted under 35 U.S.C. 154(b) by 81 days.

(21) Appl. No.: 14/757,713

(22) Filed: Dec. 23, 2015

(65) Prior Publication Data

US 2016/0367294 A1    Dec. 22, 2016

Related U.S. Application Data

(60) Provisional application No. 62/180,156, filed on Jun. 16, 2015.

(51) Int. Cl.
*A61B 17/70* (2006.01)
*A61F 2/46* (2006.01)
*A61B 17/88* (2006.01)

(52) U.S. Cl.
CPC ........ *A61F 2/4601* (2013.01); *A61B 17/8811* (2013.01); *A61B 17/7094* (2013.01)

(58) Field of Classification Search
CPC ............... A61F 2/4601; A61B 17/8811; A61B 17/7094; A61B 17/1642
See application file for complete search history.

(56) References Cited

U.S. PATENT DOCUMENTS

| | | | |
|---|---|---|---|
| 5,002,546 A * | 3/1991 | Romano | A61B 17/1628 408/127 |
| 5,484,437 A | 1/1996 | Michelson | |
| 5,658,286 A | 8/1997 | Sava | |
| 5,720,751 A | 2/1998 | Jackson | |
| 5,762,629 A | 6/1998 | Kambin | |
| 5,902,332 A | 5/1999 | Schatz | |
| 6,059,807 A * | 5/2000 | Boudjema | A61B 10/0096 606/185 |

(Continued)

*Primary Examiner* — Ellen C Hammond
*Assistant Examiner* — Stuart S Bray
(74) *Attorney, Agent, or Firm* — Hoffmann & Baron, LLP

(57) ABSTRACT

In one aspect, an instrument for placing a graft, implant and/or graft material at a target site for enhancing posterolateral fusion between two or more vertebrae is provided which includes a housing and an actuable trigger associated with the housing. A curved rigid access tube extends from the housing, the access tube terminating at a distal end. A sheath is disposed about, and moveable relative to the access tube, and a transmission is disposed in the housing. In an initial state, the sheath extends distally past the distal end of the access tube, a space being defined within the sheath distally of the distal end of the access tube to accommodate the graft, implant and/or graft material. The transmission is configured to cause an incremental displacement of the sheath relative to the distal end of the access tube upon an actuation of the trigger.

20 Claims, 73 Drawing Sheets

(56) References Cited

U.S. PATENT DOCUMENTS

| | | |
|---|---|---|
| 6,294,041 B1 | 9/2001 | Boyce |
| 6,395,007 B1* | 5/2002 | Bhatnagar ........... A61B 17/3472 |
| | | 606/86 R |
| 6,485,518 B1 | 11/2002 | Cornwall et al. |
| 6,565,605 B2 | 5/2003 | Goble et al. |
| 6,602,226 B1* | 8/2003 | Smith ...................... A61F 2/958 |
| | | 604/101.02 |
| 6,719,795 B1 | 4/2004 | Cornwall et al. |
| 6,758,863 B2 | 7/2004 | Estes et al. |
| 6,821,227 B2* | 11/2004 | Williams ............ B60K 17/3467 |
| | | 475/204 |
| 6,821,277 B2 | 11/2004 | Teitelbaum |
| 6,843,807 B1 | 1/2005 | Boyce et al. |
| 6,899,713 B2 | 5/2005 | Shaolian et al. |
| 7,074,239 B1 | 7/2006 | Cornwall et al. |
| 7,097,648 B1* | 8/2006 | Globerman ......... A61B 17/1637 |
| | | 606/247 |
| 7,223,269 B2 | 5/2007 | Chappuis |
| 7,452,369 B2 | 11/2008 | Barry |
| 7,497,869 B2 | 3/2009 | Justis |
| 7,517,358 B2 | 4/2009 | Petersen |
| 7,582,106 B2 | 9/2009 | Teitelbaum et al. |
| 7,708,761 B2 | 5/2010 | Petersen |
| 7,722,895 B1 | 5/2010 | McKay et al. |
| 7,837,713 B2 | 11/2010 | Petersen |
| 8,002,775 B2 | 8/2011 | McKay |
| 8,070,782 B2 | 12/2011 | McKay |
| 8,337,556 B2 | 12/2012 | Shaolian et al. |
| 8,470,354 B2 | 6/2013 | McKay et al. |
| 8,486,077 B1 | 7/2013 | Kornel |
| 8,845,640 B2* | 9/2014 | McLean ............. A61B 17/7032 |
| | | 606/86 A |
| 8,945,137 B1* | 2/2015 | Greenhalgh ..... A61B 17/00234 |
| | | 606/93 |
| 9,314,252 B2* | 4/2016 | Schaller ................ A61B 17/16 |
| 9,510,885 B2* | 12/2016 | Burger ............... A61B 17/8811 |
| 9,610,083 B2* | 4/2017 | Kuntz ................ A61B 17/1642 |
| 2002/0173850 A1 | 11/2002 | Brodke et al. |
| 2003/0144671 A1* | 7/2003 | Brooks ...................... A61F 2/95 |
| | | 606/108 |
| 2003/0191523 A1 | 10/2003 | Hojeibane |
| 2004/0049270 A1 | 3/2004 | Gewirtz |
| 2004/0097469 A1 | 5/2004 | Little et al. |
| 2005/0177237 A1 | 8/2005 | Shappley et al. |
| 2006/0036273 A1* | 2/2006 | Siegal ................ A61B 17/1757 |
| | | 606/190 |
| 2006/0111779 A1 | 5/2006 | Petersen |
| 2006/0235279 A1 | 10/2006 | Hawkes et al. |
| 2006/0282155 A1* | 12/2006 | Fearn ...................... A61F 2/966 |
| | | 623/1.12 |
| 2007/0055279 A1* | 3/2007 | Sand ................. A61B 17/8811 |
| | | 606/92 |
| 2007/0077267 A1 | 4/2007 | Motz, IV et al. |
| 2007/0233146 A1* | 10/2007 | Henniges ........... A61B 17/3472 |
| | | 606/91 |
| 2007/0270844 A1 | 11/2007 | Lin et al. |
| 2009/0054901 A1* | 2/2009 | Oh ........................ A61F 2/4455 |
| | | 606/99 |
| 2009/0076551 A1 | 3/2009 | Petersen |
| 2009/0105713 A1* | 4/2009 | Nimgaard ................. A61F 2/95 |
| | | 606/99 |
| 2009/0177206 A1* | 7/2009 | Lozier ............... A61B 17/1617 |
| | | 606/93 |
| 2009/0234397 A1 | 9/2009 | Petersen |
| 2009/0259298 A1 | 10/2009 | Mayberry et al. |
| 2010/0030255 A1 | 2/2010 | Berra et al. |
| 2010/0036443 A1* | 2/2010 | Hutton ............... A61B 17/7032 |
| | | 606/86 R |
| 2010/0076480 A1* | 3/2010 | Lu ........................ A61F 2/4601 |
| | | 606/192 |
| 2010/0222829 A1 | 9/2010 | Petersen |
| 2010/0241177 A1* | 9/2010 | Schaller ............. A61B 17/7094 |
| | | 606/86 A |
| 2010/0268232 A1* | 10/2010 | Betz ......................... A61F 2/30 |
| | | 606/79 |
| 2010/0268234 A1* | 10/2010 | Aho ................... A61B 17/1617 |
| | | 606/80 |
| 2010/0298832 A1* | 11/2010 | Lau .................... A61B 17/1642 |
| | | 606/80 |
| 2010/0312279 A1* | 12/2010 | Gephart ............. A61B 17/3421 |
| | | 606/264 |
| 2012/0016369 A1* | 1/2012 | O'Halloran ........ A61B 17/1671 |
| | | 606/93 |
| 2012/0215259 A1 | 8/2012 | Cannestra |
| 2012/0253316 A1* | 10/2012 | Oktavec ............. A61B 17/3472 |
| | | 604/506 |
| 2012/0277801 A1 | 11/2012 | Marik et al. |
| 2013/0345710 A1 | 12/2013 | Kleiner et al. |
| 2014/0221967 A1* | 8/2014 | Childs ................ A61B 17/8805 |
| | | 604/506 |
| 2015/0112352 A1* | 4/2015 | Krause .................. A61F 2/4601 |
| | | 606/94 |
| 2015/0230834 A1 | 8/2015 | Cannestra |
| 2016/0081732 A1* | 3/2016 | Baroud .............. A61B 17/8811 |
| | | 623/23.62 |
| 2016/0296344 A1* | 10/2016 | Greenhalgh .......... A61F 2/4601 |
| 2017/0020673 A1* | 1/2017 | Colclough ................ A61F 2/28 |
| 2017/0112507 A1* | 4/2017 | Crainich ............ A61B 17/1642 |

\* cited by examiner

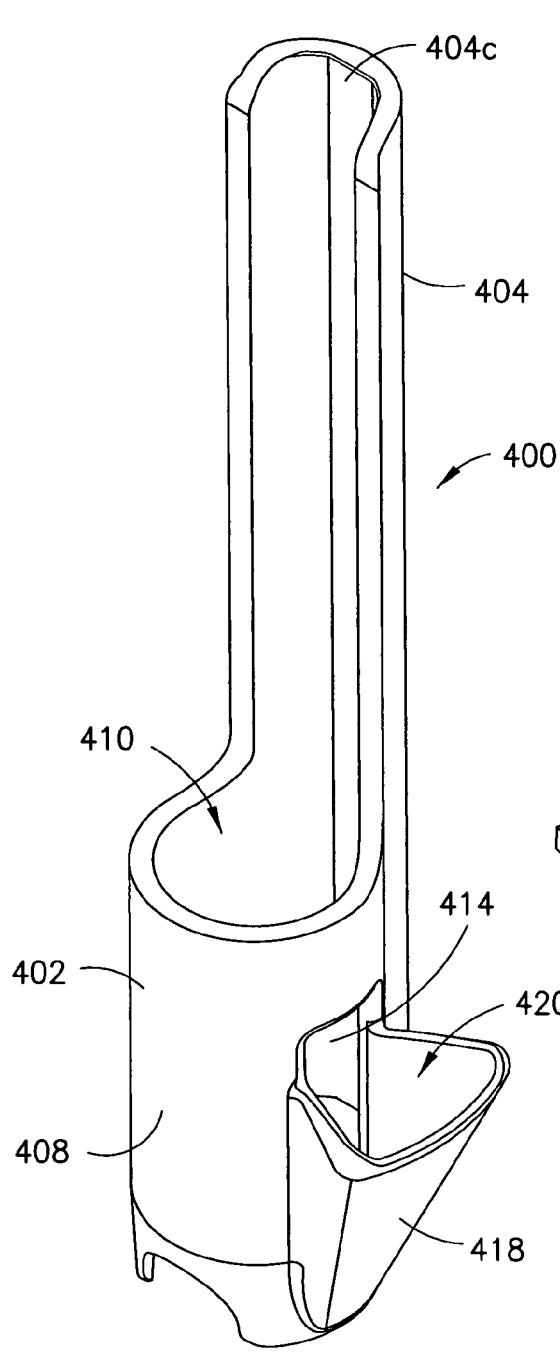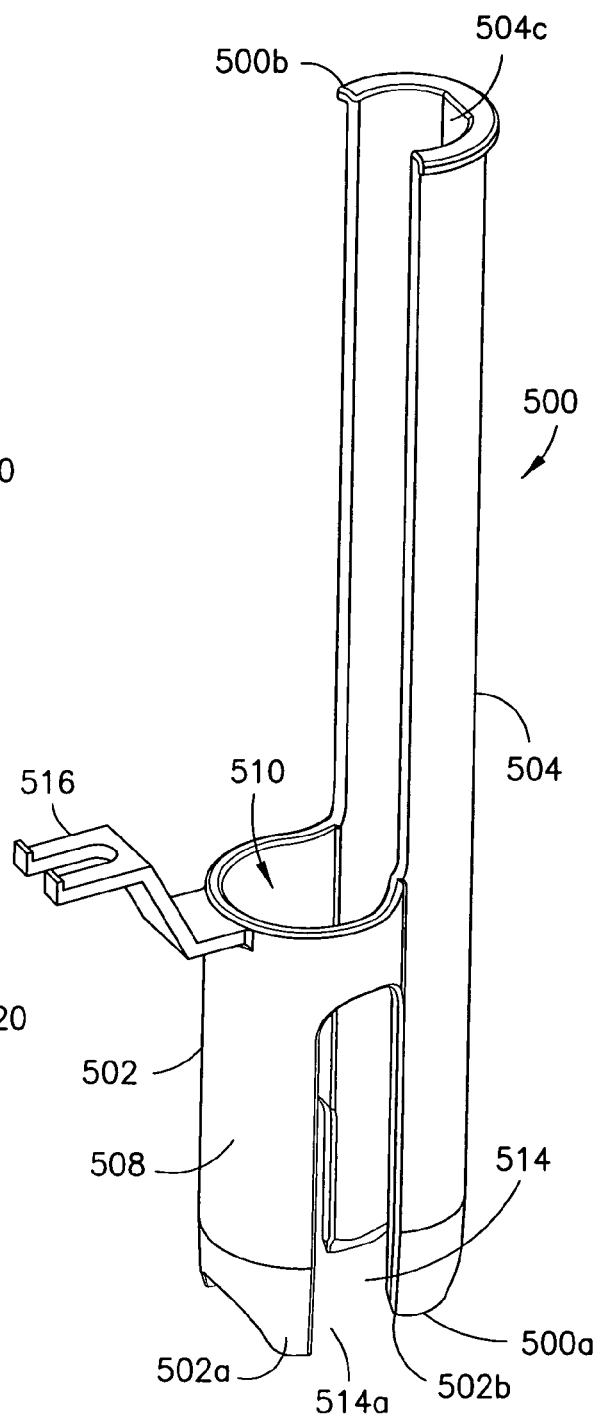

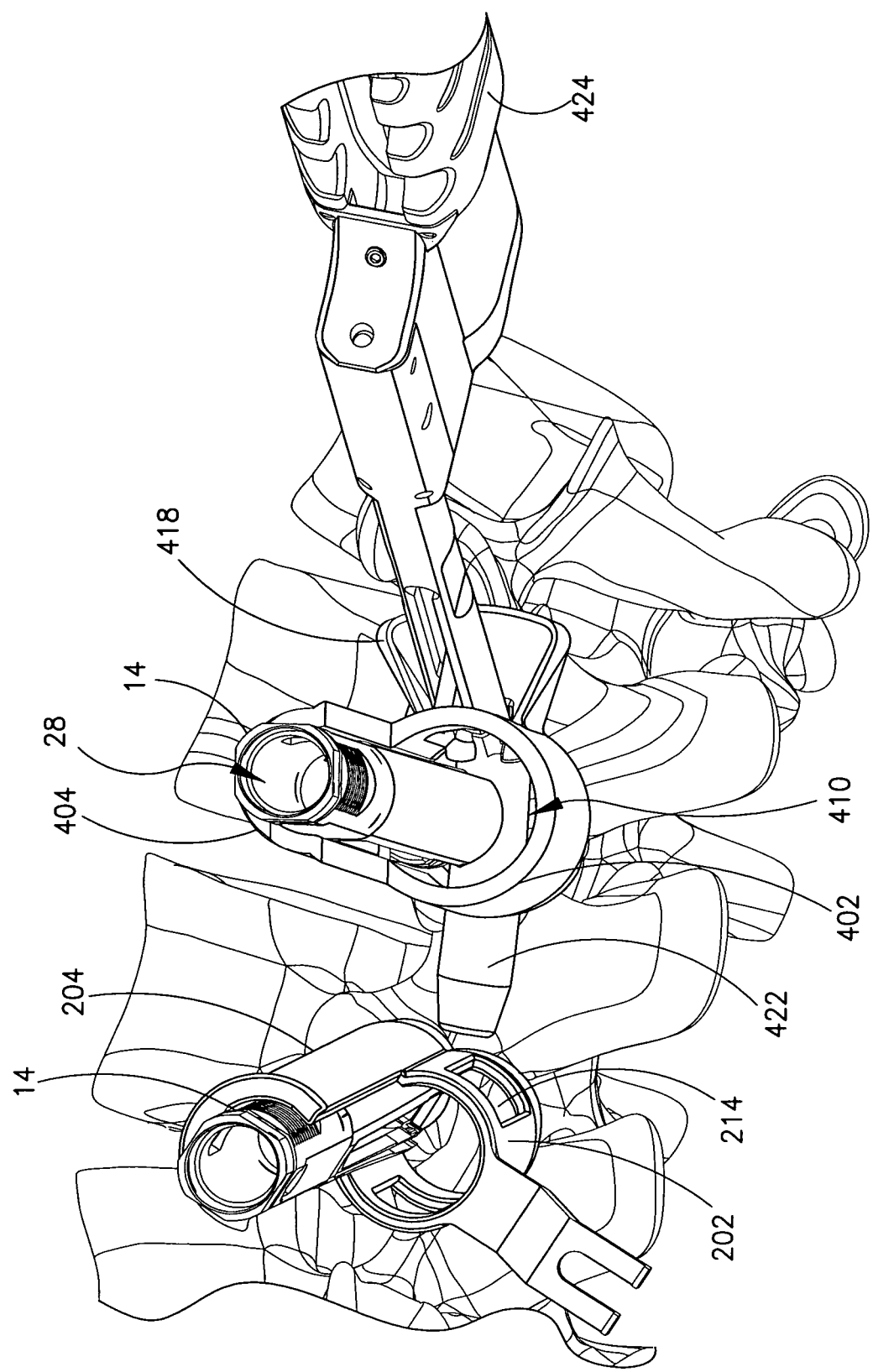

INSTRUMENT AND SYSTEM FOR PLACING GRAFT, IMPLANT AND GRAFT MATERIAL FOR MINIMALLY INVASIVE POSTEROLATERAL FUSION

CROSS-REFERENCE TO RELATED APPLICATION

This application claims the benefit of U.S. Provisional Patent Application No. 62/180,156, filed Jun. 16, 2015, the contents which are incorporated by reference herein.

BACKGROUND OF THE INVENTION

The purpose of this invention is to provide for an instrument and system useable for placing a graft, implant and/or graft material at a target site during a minimally invasive posterolateral fusion procedure. The instrument and system herein may be used with the system and methods of posterolateral fusion disclosed in U.S. application Ser. No. 14/740,381, filed Jun. 16, 2015, and assigned to the same assignee as herein. U.S. application Ser. No. 14/740,381 is incorporated by reference herein.

SUMMARY OF THE INVENTION

In one aspect, an instrument for placing a graft, implant and/or graft material at a target site for enhancing posterolateral fusion between two or more vertebrae is provided which includes a housing and an actuable trigger associated with the housing. A curved rigid access tube extends from the housing, the access tube terminating at a distal end. A sheath is disposed about, and moveable relative to the access tube, and a transmission is disposed in the housing. In an initial state, the sheath extends distally past the distal end of the access tube, a space being defined within the sheath distally of the distal end of the access tube to accommodate the graft, implant and/or graft material. The transmission is configured to cause an incremental displacement of the sheath relative to the distal end of the access tube upon an actuation of the trigger.

These and other features of the invention will be better understood through a study of the following detailed description and accompanying drawings.

BRIEF DESCRIPTION OF THE DRAWINGS

FIG. 8 is a perspective view of a third embodiment of a tubular retractor.

FIG. 10 is an enlarged top view of FIG. 9 illustrating the blunt dilator extending through an access port of the tubular retractor as visualized by a surgeon through the access port.

FIG. 11 is a perspective view of a fourth embodiment of a tubular retractor.

DETAILED DESCRIPTION OF THE INVENTION

Figure 1:
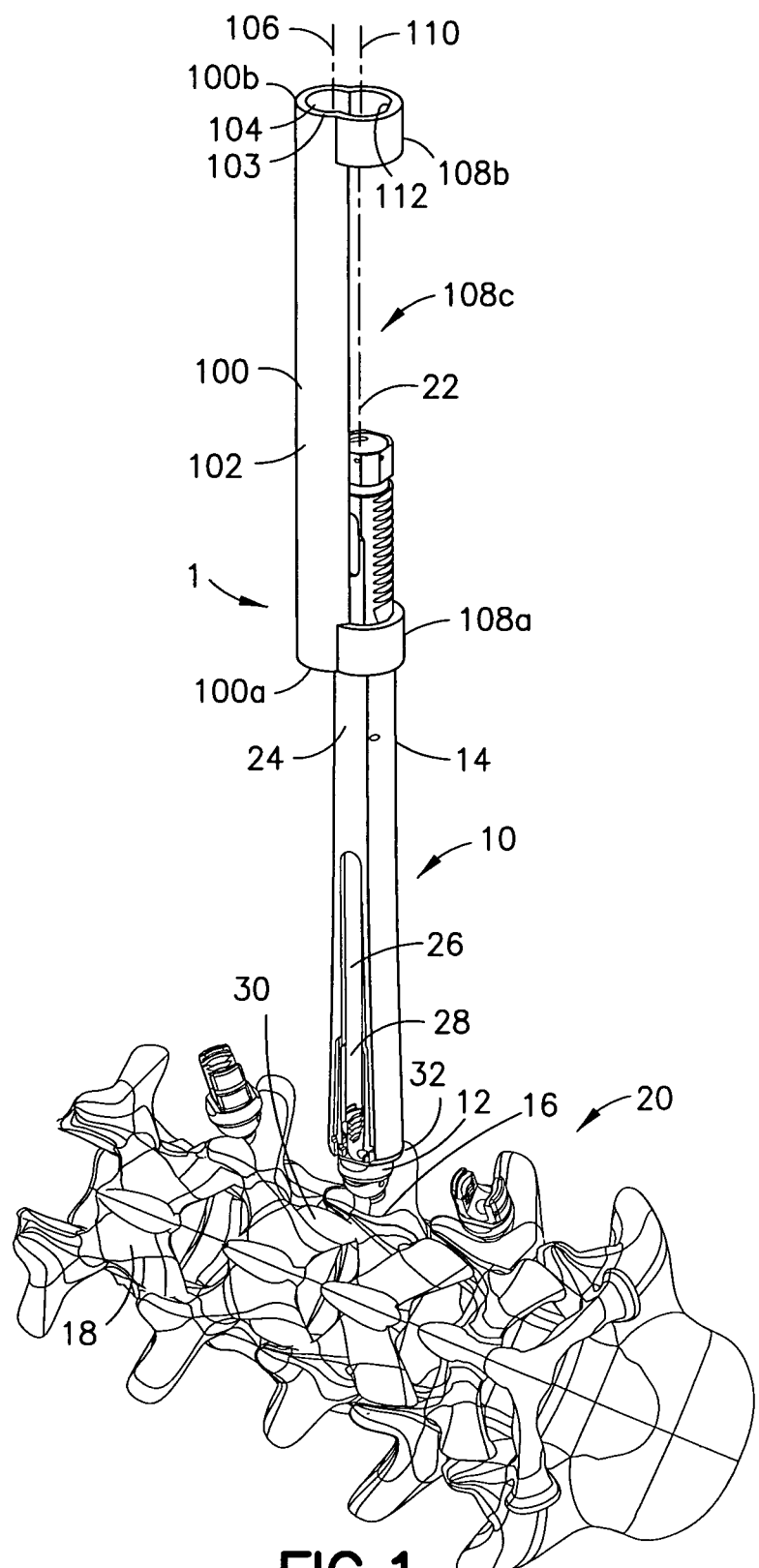
FIG. 1 is a top perspective view of a portion of a spine illustrating partially assembled components a minimally invasive spinal fusion system including a first embodiment of a tubular retractor of the invention.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

As set forth herein, the subject invention provides the ability to visualize and access surrounding bony elements and soft tissues in a mobile manner while utilizing a well-established anchor point in the pedicle of spinal vertebrae. Instrumentation necessary for soft tissue preparation and bony removal may be placed either directly through the access port, through access slots in the side of the tubular retractor, or through slotted elements in the screw extension. This instrumentation provides for efficient and desired preparation of the surrounding tissues prior to delivery of an implant and bone graft materials. The system disclosed hereinbelow for establishing a pathway between adjacent vertebrae comprise a series of blunt dissectors or dilators that may then be followed by a deployable graft implant.

One aspect of the system described herein is in allowing a surgeon to perform a posterior lateral fusion using minimally invasive access and visualization techniques such as a fixed and mobile tubular retractor. In general, the instrumentation and method allows for safe access through the overlying tissue and muscle, direct visualization of the bony elements (e.g. the preparation of the fusion bed), and delivery of bone graft material between multiple spinal segments necessary to achieve spinal fusion. As is well known, a spinal segment comprises opposing vertebral bodies of a spine and the intervertebral disc therebetween.

Figure 2:
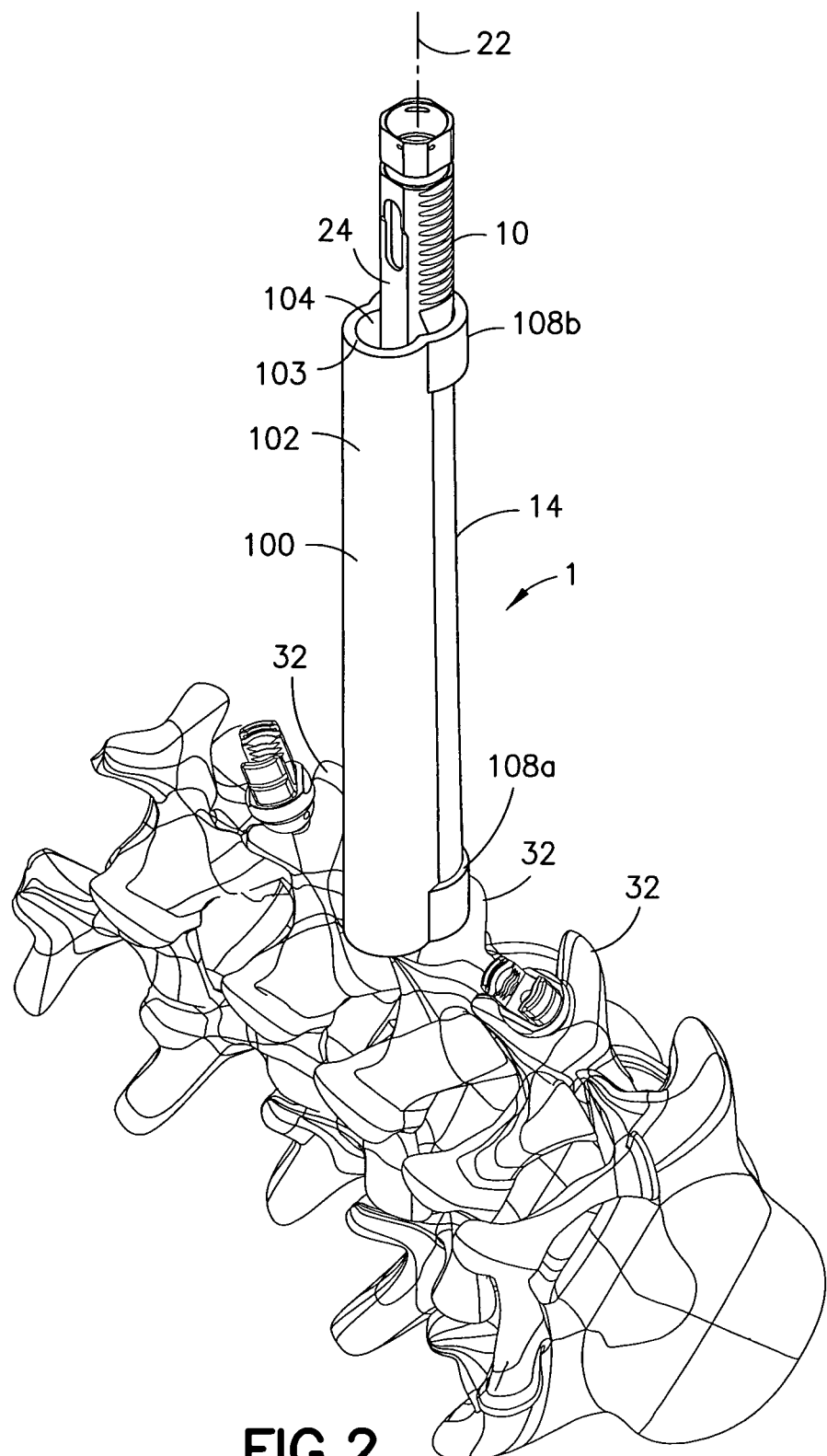
FIG. 2 is the view of FIG. 1 with the components of the minimally invasive spinal fusion system assembled and attached to the spine.

Turning now to FIGS. 1-2, details of one particular arrangement of a minimally invasive spinal fusion system 1 comprising a pedicle screw extension assembly 10 and a tubular retractor 100 for minimally invasive spine fusion are described. Pedicle screw extension assembly 10 comprises a spinal screw 12 and an elongate screw extension 14 releasably attached to screw 12. Spinal screw is an elongate fixation member, preferably a multi-axial pedicle screw attached as shown to a pedicle 16 of a vertebral body 18 of a spine 20. Elongate extension 14 defines a longitudinal axis 22 extending generally centrally along the length of extension 14. Extension 14 is generally cylindrical along its outer length and has a pair of flat diametrically opposed surfaces 24 extending lengthwise. A pair of substantially opposite slots 26 extends through flat surfaces 24, each slot 26 communicating with a lumen 28 extending generally centrally through extension 14 along 20. Pedicle screw 12 includes a threaded shaft 12a and a yoke 12b articulatingly and rotatably attached to said screw shaft 12a (see FIG. 15). Elongate screw extension 14 is releasably coupled to yoke 12b for articulation and rotation of extension 14 about screw shaft 12a. Details of pedicle screw extension assembly 10 and the arrangement by which elongate extension 14 is releasably coupled to yoke 12b are described more fully in U.S. Pat. No. 8,845,640, entitled "Pedicle Screw Extension for Use in Percutaneous Spinal Fixation", issued in the name of Scott Mclean et al. on Sep. 30, 2014 (the '640 Patent). The '640 Patent is assigned to the same assignee as is the subject application, the contents of the '640 patent being incorporated herein by reference in their entirety.

Referring still to FIGS. 1-2, tubular retractor 100 provides for a closed channel access to the facet region 30 of spine 20, tubular retractor 100 being releasably affixed to the multi-axial pedicle screw 12 through extension 14. Tubular retractor 100 is slid over extension 14 and pushed down through an incision formed through the skin in order to abut against the posterior spinal elements of spine 20. Instruments, as will be described, may be passed through the closed tubular working space in order to access the facet capsule and adjacent midline elements of spine 20.

Tubular retractor 100 is preferably elongate having a distal end 100a, a proximal end 100b and an axial length therebetween. Tubular retractor 100 includes an access port 102 including a partially cylindrical wall 103 defining a partially cylindrical pathway 104 extending substantially the entire length of tubular retractor 100, pathway 104 being configured for instrument access and visualization by the surgeon. Pathway 104 defines a second longitudinal axis 106 extending along the length of tubular retractor 100 through distal end 100a and proximal end 100b. Tubular retractor 100 includes a pair of generally circular attachment rings 108a and 108b disposed respectively at the distal end 100a and proximal end 100b. Rings 108a and 108b are axially spaced from each other and together define an attachment portion for attaching tubular retractor 100 to elongate extension 14, the axial length of the combined rings 108a and 108b being different than and less than the length of access port 102. Each of rings 108a and 108b has a curved interior surface for relatively close sliding fit over the generally cylindrical outer surface of extension 14. An interior surface 112 of each of rings 108a and 108b is formed as a flat surface to provide a cooperative keying arrangement with one of flat surfaces 24 of extension 14, as will be described. Rings 108a and 108b together define a third longitudinal axis 110 that is generally parallel to and offset from second longitudinal axis 106. The open axial space 108c between rings 108a and 108b defines a side opening of tubular retractor 100 that is in communication with pathway 104.

FIG. 2 demonstrates the attachment of tubular retractor 100 to screw extension 14, which is placed down through the same incision of the skin of the patient through which pedicle screw extension assembly 10 extends. During attachment, flat surfaces 112 of rings 108a and 108b slidingly engage flat surfaces 24 and extension 14 releasably fixing tubular retractor 100 to extension 14 in a manner to prevent relative rotation between tubular retractor 100 and screw extension 14 while allowing relative axial movement therebetween. Thus, joint articulation and rotation of tubular retractor 100 relative to threaded shaft 12a of pedicle screw 12 is provided. During attachment third longitudinal axis 110 of rings 108a and 108b is substantially coaxial with first longitudinal axis 22 of screw extension 14 with second longitudinal axis 106 of pathway 104 being laterally offset from first longitudinal axis 22. As such, pathway 104 is laterally offset from screw extension 14 and rotatable and articulatable with screw extension 14 about spinal screw shaft 12a. As depicted in FIG. 2, tubular retractor 100 is fully seated with access port 102 defining a closed working channel pathway 104 having a fixed area transverse to second longitudinal axis 106 for safe access to spinal facets and other posterior spinal elements. Instruments can be placed through pathway 104 to remove soft tissues overlying bony elements of the posterior portion of spine 20, followed by decortication of bony surfaces and placement of a suitable bone graft, as will be described. In addition, tubular retractor 100 can be rotated laterally about first longitudinal axis 22 for access to the transverse processes 32 of the spine 20. Upon rotation of tubular retractor 100 about first longitudinal axis 22 of extension 14 an area of bony surface of spine 20 is exposed adjacent pedicle screw 12 that is greater than the fixed area of said pathway 104. Further, pathway 104 may be accessed through side opening 108c via slots 26 extending through screw extension 14. Tissue preparation instruments or bone graft material devices may be introduced through side opening 108c, through slots 26 and into pathway 104 while the surgeon has full access to and visualization of the prepared site through pathway 104 to observe the tissue preparation or bone graft material delivery.

Figure 3:
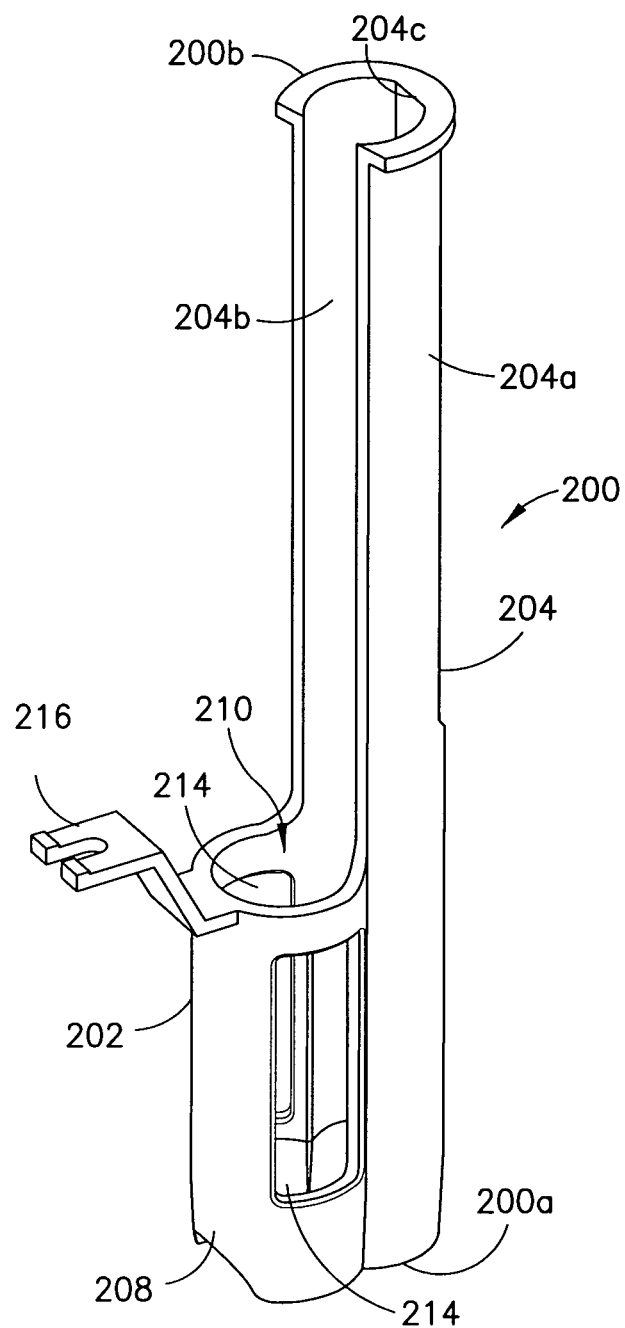
FIG. 3 is a perspective view of a second embodiment of a tubular retractor.
Figure 4:
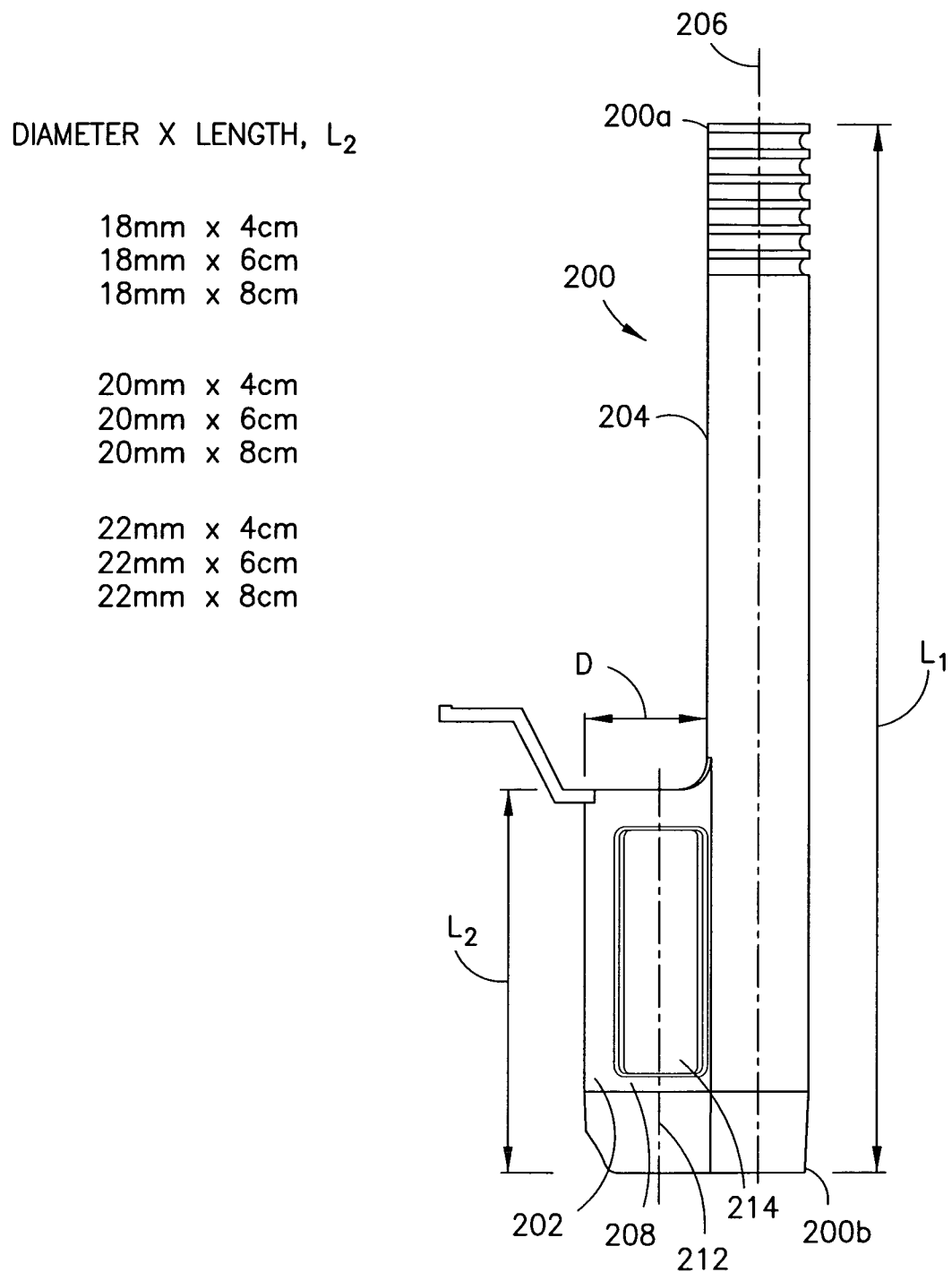
FIG. 4 is a side elevation view of the tubular retractor of FIG. 3.

Turning now to FIGS. 3-4, a second alternative tubular retractor 200 for use in minimally invasive spinal fusion system 1 is described. Tubular retractor 200 is elongate having a distal end 200a and a proximal end 200b and overall length $L_1$ extending from distal end 200a to proximal end 200b as illustrated in FIG. 4. Tubular retractor 200 comprises an access port 202 and an attachment portion 204. Attachment portion 204 extends longitudinally over the length $L_1$ and access port 202 extends from distal end 200a for a length $L_2$ along tubular retractor 200 toward proximal end 200b. Length $L_2$ of access port 202 is different than and less than the length $L_1$ of attachment portion 204. Length $L_1$ is adapted to the amount of soft tissue and muscle overlying the spinal elements and necessary to safely reach the site of bone fusion procedure. Attachment portion 204 comprises a generally curved open channel 204a and defines a longitudinal attachment axis 206 similar to third longitudinal axis 110 defined by attachment rings 108a and 108b of tubular retractor 100. Attachment portion 204 has a curved interior surface 204b for relatively close sliding fit over the generally cylindrical outer surface of screw extension 14 as illustrated in FIG. 3. An interior surface 204c of attachment portion 204 is formed as a flat surface as depicted in FIG. 3 to provide a cooperative keying arrangement with one of flat surfaces 24 of extension 14, as described hereinabove with respect to tubular retractor 100.

Access port 202 includes a partially cylindrical wall 208 defining a substantially enclosed, partially cylindrical pathway 210 extending the length $L_2$ of access port 202, pathway 210 being configured for instrument access and visualization by the surgeon. Pathway 210 defines a longitudinal access axis 212 similar to second longitudinal axis 106 defined by access port 102 of tubular retractor 100. Longitudinal access axis 212 is generally parallel to and offset from longitudinal attachment axis 206. Access port 202 has a pair of side openings defined by windows 214 extending through two substantially opposing sides of wall 208 in communication with pathway 210, windows 214 being configured for placement of instruments and implants, as well as for potentially enhanced visualization and illumination.

Pathway 210 of access port 202 has a dimension transverse to longitudinal access axis 212, such as diameter D, as shown in FIG. 3, defining pathway 210 as a fixed, substantially enclosed area for safe access to spinal facets and other posterior spinal elements. Instruments can be placed through pathway 210 to remove soft tissues overlying bony elements of the posterior portion of spine 20, followed by decortication of bony surfaces and placement of a suitable bone graft, as will be described.

The tubular retractors 200 range in sizes adaptable to patient anatomy variations. The diameter D and the length $L_2$ of access port 202 may vary based on patient anatomy. A surgeon may use different lengths or different diameters depending on the curvature of the spine and amount of overlying soft tissues and muscle. The configuration of tubular tractors 200 as shown in FIG. 3 demonstrates a diameter D ranging from 18 mm to 22 mm, with lengths $L_2$ from 4 cm up to 8 cm. A kit of different sized tubular retractors 200 and various instruments, dilators and graft implants described hereinbelow may be provided for a surgical procedure. The surgeon may select an access port length $L_2$ to be as short as possible (just exiting the skin line, S in FIG. 16), in order to maximize the available angular trajectory that may be used for visualization and placement of instruments such as rongeurs or drills for bone decortication. In addition, the presence of side access windows 214 provides for an alternate way to place instruments in a trajectory different from the line-of-sight of the surgeon through pathway 210. A tab 216 projects from wall 208 that allows the surgeon to optionally affix tubular retractor 200 to an operating room table (via a flexible arm assembly not shown) for additional stabilization or for hands-free operation through access port 202.

Figure 5:
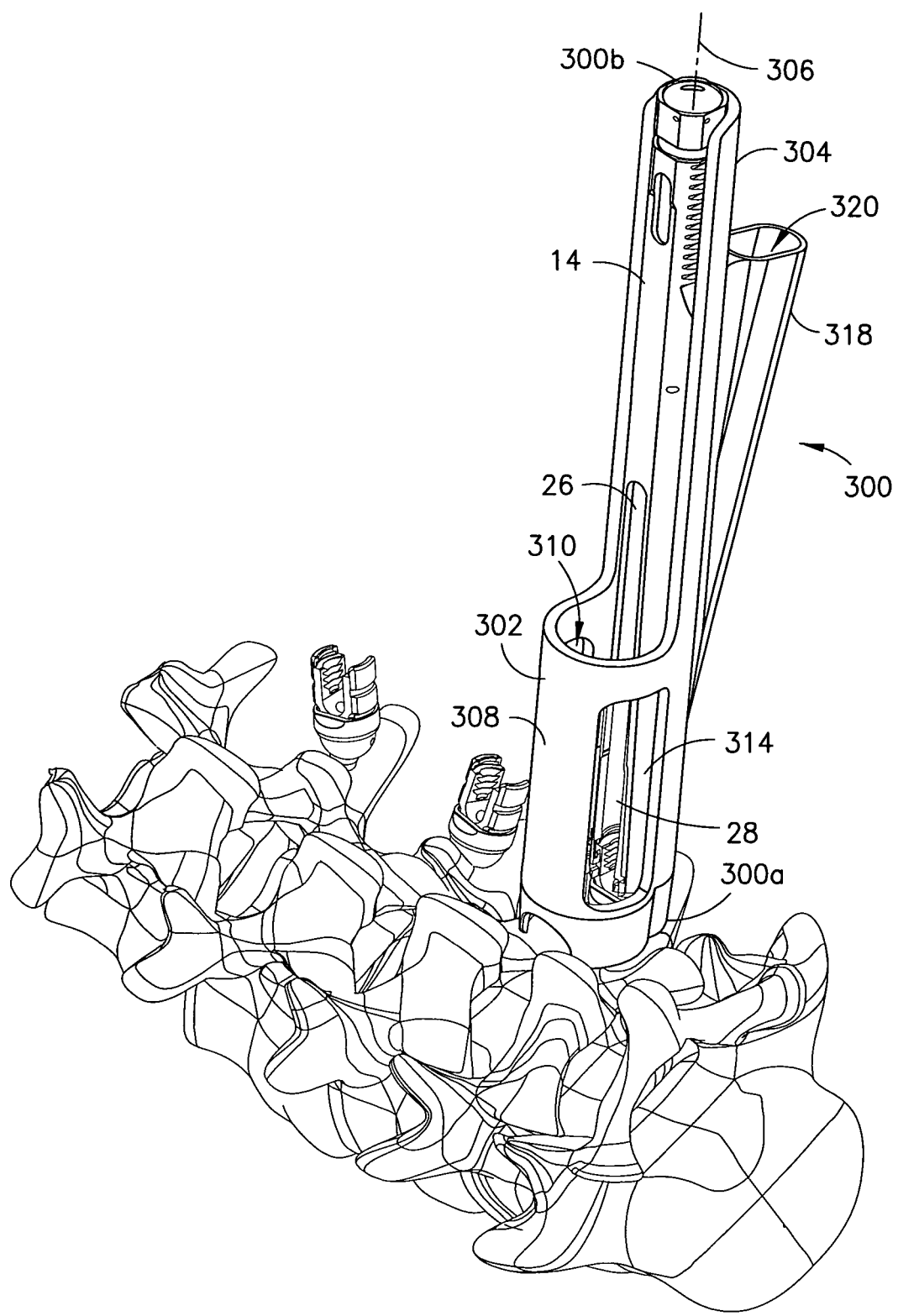
FIG. 5 is top perspective view of a third embodiment of the tubular retractor attached to the spine.
Figure 6:
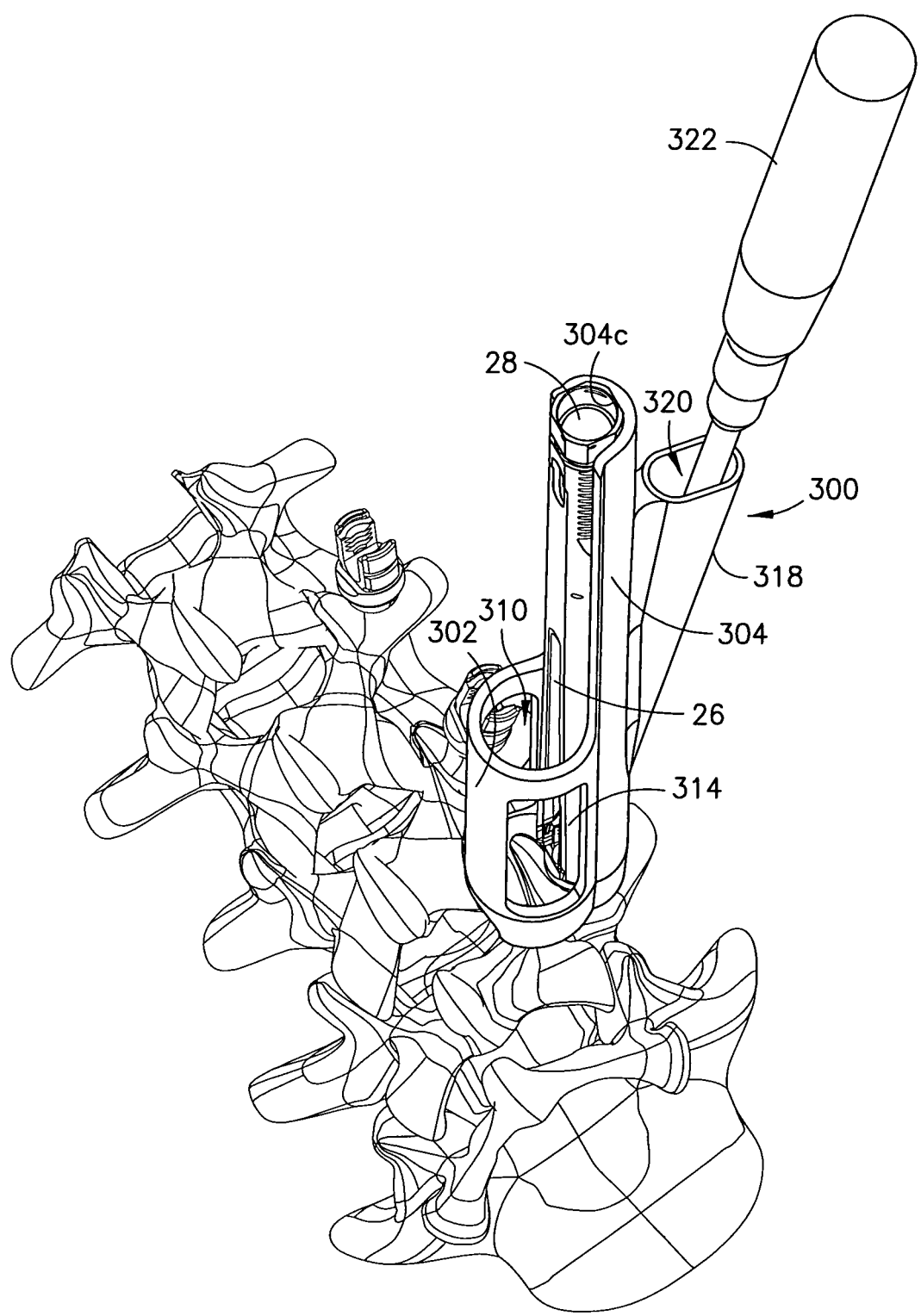
FIG. 6 is top perspective view of the tubular retractor of FIG. 5 in use with a tissue preparation instrument.
Figure 7:
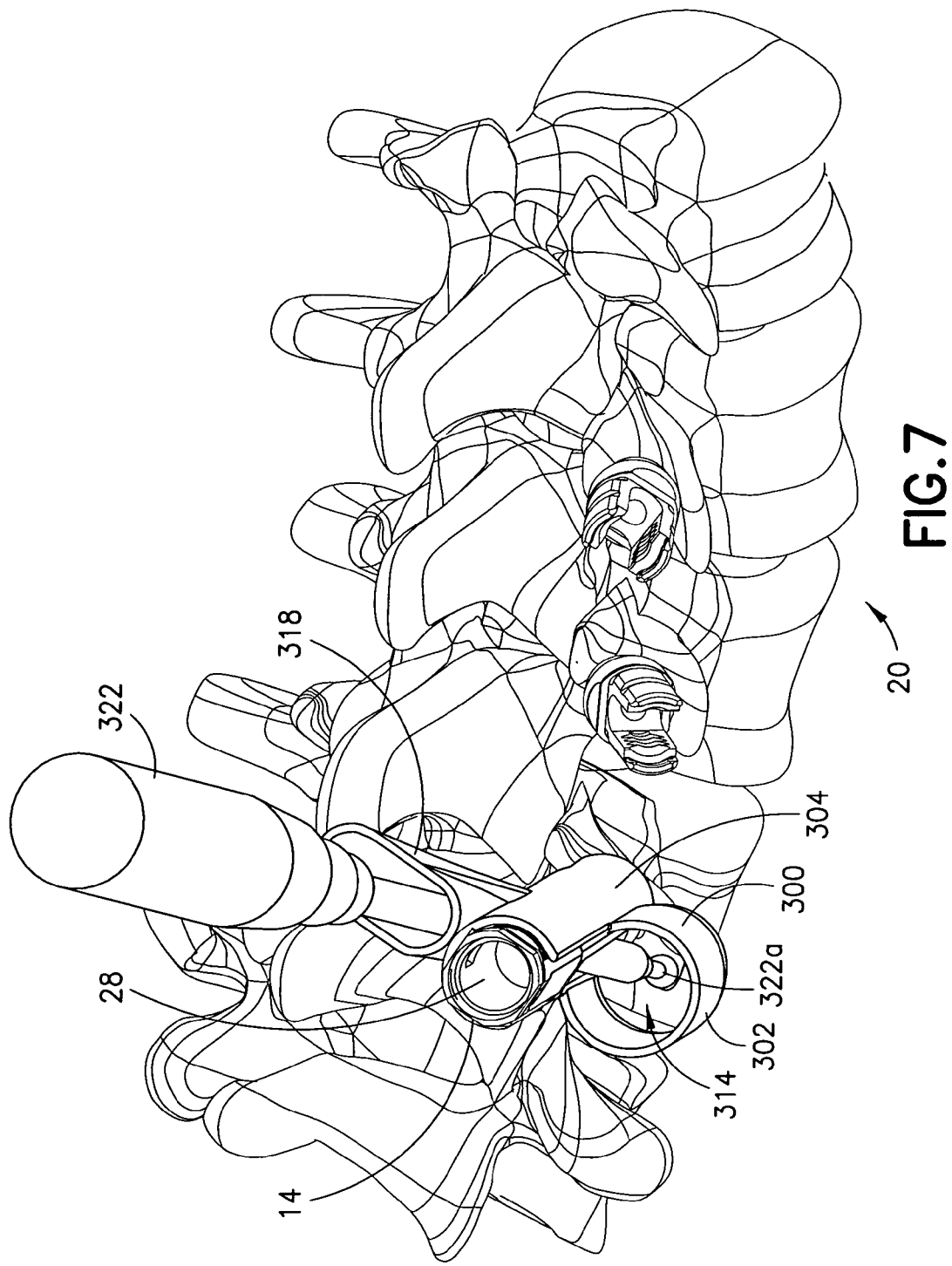
FIG. 7 is an enlarged top view of FIG. 6 illustrating the visualization of the access port of the tubular retractor as would be seen by a surgeon.

Turning now to FIGS. 5-7, a third alternative tubular retractor 300 for use in minimally invasive spinal fusion system 1 is described. Tubular retractor 300 includes a modification of tubular retractor 200. Reference numerals illustrating elements of tubular retractor 300 that are common with tubular retractor 200 are increased by 100 for ease of description. In tubular retractor 300, an angular side access port 318 having a guide channel 320 extends from attachment portion 304. A side opening defined by an angular side access channel 320 intersects longitudinal attachment axis 306 of attachment portion 304 and communicates through the slots 26 and lumen 28 of extension 14 with pathway 310 of access port 302 to allow for angled access to the pathway 310 across the screw extension 14. This allows for placement of an instrument 322 such as a drill or burr into the working space of pathway 310 without potentially obstructing the direct visualization of the pathway 310 by the surgeon. In addition, depth stops may be added to instruments 322 placed down angular side access channel 320 for greater control of penetration depth while removing soft tissue and bone prior to graft delivery. The top view of spine 20 as illustrated in FIG. 7 demonstrates placement of the instrument tip 322a across screw extension 14 and into the operative pathway 310 provided by tubular retractor 300. In this embodiment it is also possible to add a depth stop across the extension slot in order to limit the depth of penetration of the powered instrument. Multiple tissue preparation instruments for preparing bony surfaces or soft tissue for may be placed simultaneously through the three different access openings provided by pathway 310, windows 314 and angular access channel 320.

Figure 9:
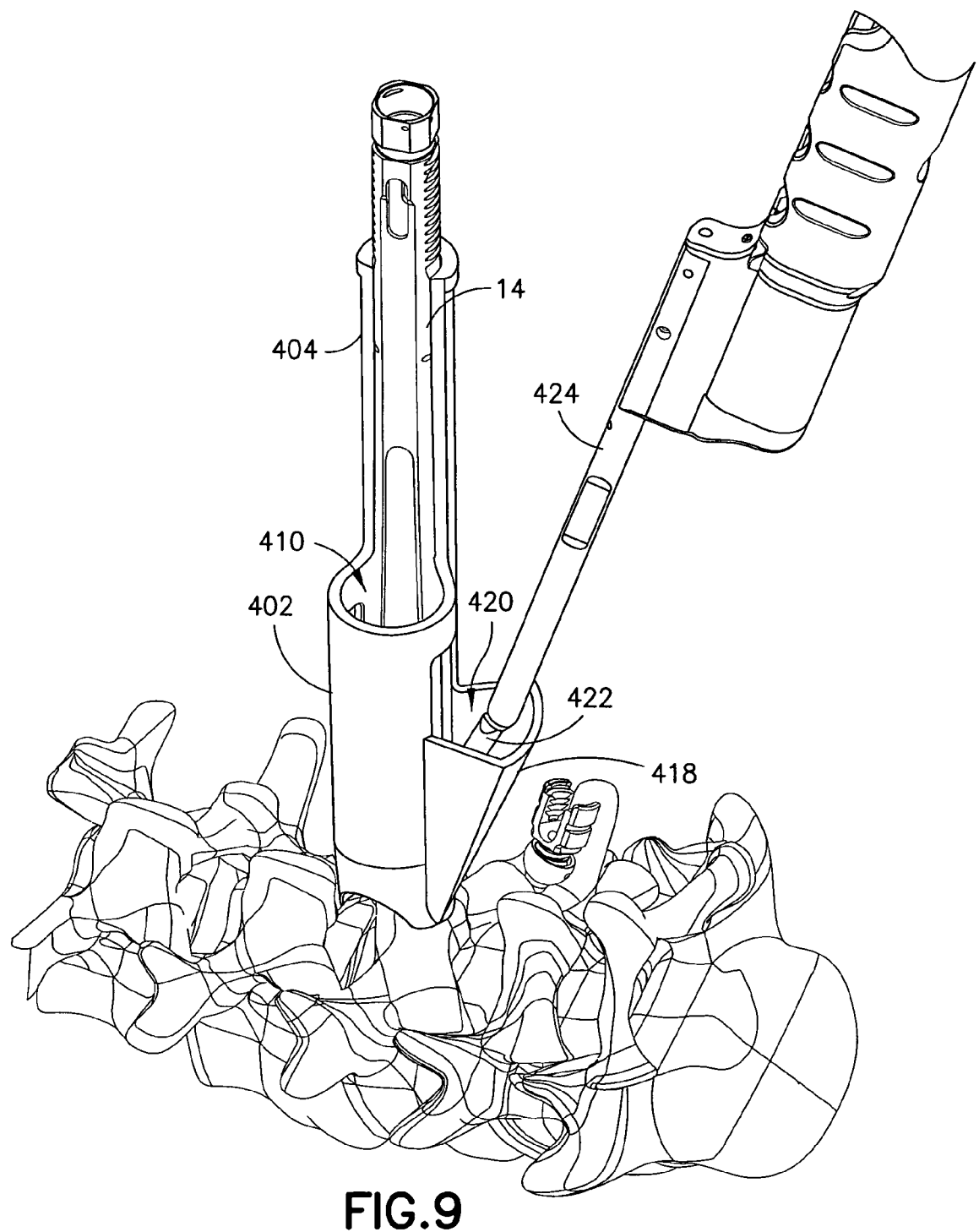
FIG. 9 is top perspective view of the tubular retractor of FIG. 8 in use with a blunt tissue dilator introducer.

Referring now to FIGS. 8-10, a fourth alternative tubular retractor 400 for use in minimally invasive spinal fusion system 1 is described. Tubular retractor 400 includes a modification of tubular retractor 200. Reference numerals illustrating elements of tubular retractor 400 that are common with tubular retractor 200 are increased by 200 for ease of description. In tubular retractor 400, an angular window guide funnel 418 having a guide channel 420 communicates with one of windows 414. The configuration of tubular retractor 400 may facilitate a controlled placement of a blunt dilator 422 by an introducer instrument 424 as shown in FIG. 9 capable of creating a subcutaneous tissue pathway between two spinal vertebral bodies as shown in FIG. 10 prior to graft insertion. The shape of guide funnel 418 may assist in reducing tissue migration into window 414.

Turning now to FIG. 11, a fifth alternative tubular retractor 500 for use in minimally invasive spinal fusion system 1 is described. Tubular retractor 500 includes a modification of tubular retractor 200. Reference numerals illustrating elements of tubular retractor 500 that are common with tubular retractor 200 are increased by 300 for ease of description. Tubular retractor 500 may be used for placement of a bone graft material between adjacent spinal levels. An opening 514a is provided at distal end of windows 514. These respective openings 514a allow for initially placing a bone graft material in a generally 90° orientation (relative to the skin line S) and then rotating the graft material up to about 90° into position between the distal forks 502a and 502b on either side of opening 514a prior to deploying the graft material between the two spine segments.

Having described various alternative tubular retractors, a method of using such tubular retractors in minimally invasive spinal fusion system 1 is now set forth, with reference primarily, but not exclusively, to tubular retractor 200 and FIGS. 12-21. The primary anchor point for the various steps involved in the access, visualization, preparation, and grafting procedure is based on the fixation of multi-axial pedicle screw 12 into the pedicle of a vertebral body. This is a well-known and established anchor point. Once the tubular retractor 200 is affixed to the screw extension 14, pathway 210 is laterally offset from screw extension 14 and rotatable and articulatable with screw extension 14 about spinal screw shaft 12a. The surgeon is therefore able to rely upon a fixed access point that is stable and well known anatomically to establish access to bony surfaces of spinal elements surrounding pedicle screw 12. In addition, the multi-axial feature of pedicle screw 14 allows for multiple angles of visualization, preparation, and graft placement as the tubular retractor 200 is rotated and pivoted about the screw shaft 12a.

Figure 12:
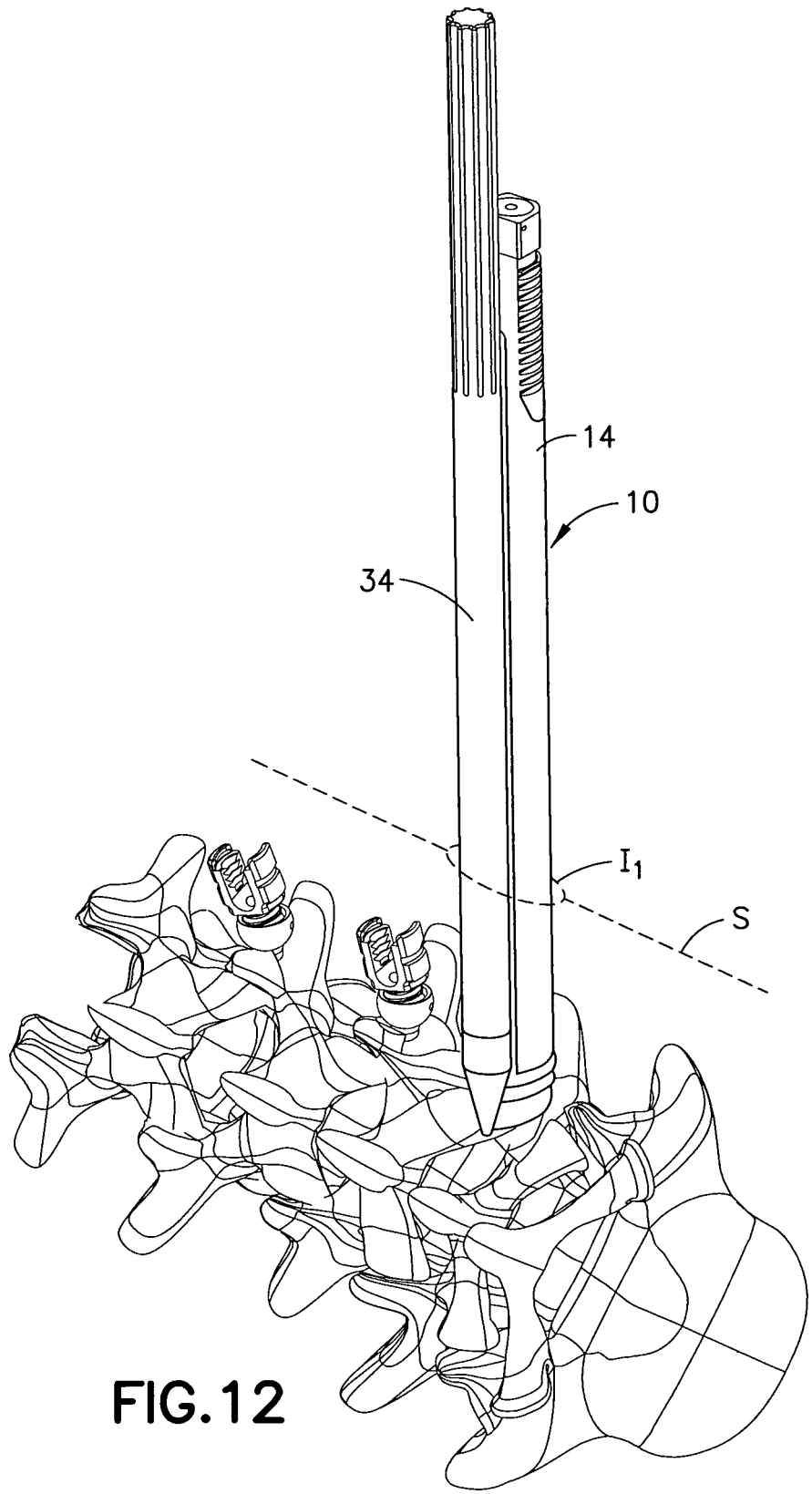
FIG. 12 is a top perspective view of a first tissue dilator being inserted through tissue of a patient adjacent to a pedicle screw extension assembly attached to the spine.
Figure 13:
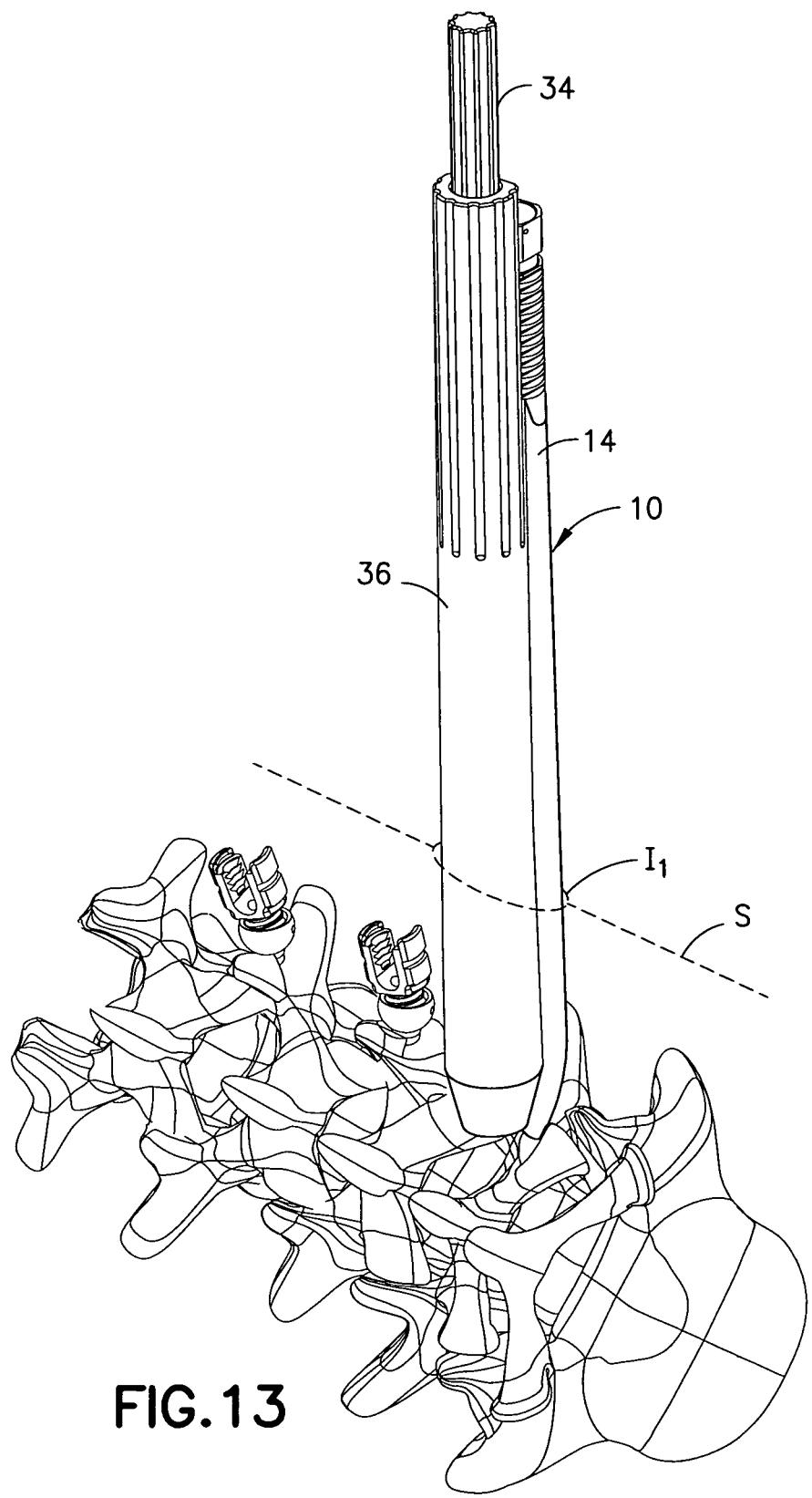
FIG. 13 is a top perspective view of a second tissue dilator being inserted through tissue of a patient adjacent to the pedicle screw extension assembly attached to the spine.

The initial step of the procedure involves the formation of small incision $I_1$ through the skin line S and into the tissue of a patient as shown in FIG. 12. The term "small incision" as used herein is meant to mean an incision of about 4 mm to 25 mm in length sufficient for introduction of the initial dilator 34, and preferably in the range of about 5 mm to 10 mm. A pedicle screw extension assembly 10 is placed through a first incision $I_1$ with pedicle screw 12 threadedly attached to the pedicle 16 of a vertebral body 18 in a manner as described in the '640 patent, incorporated herein by reference. Screw extension 14 has a length that projects outwardly from skin line S. The skin and tissues adjacent to screw extension 14 are dilated using a series of progressively larger smooth dilators, the initial dilator 34 being shown in FIG. 12. The initial dilator 24 is slid axially adjacent to screw extension 14. This is followed by one or more larger dilators to provide for the exposure necessary for placement of outer tubular retractor 200. The largest dilator 36 is shown in FIG. 13.

Figure 14:
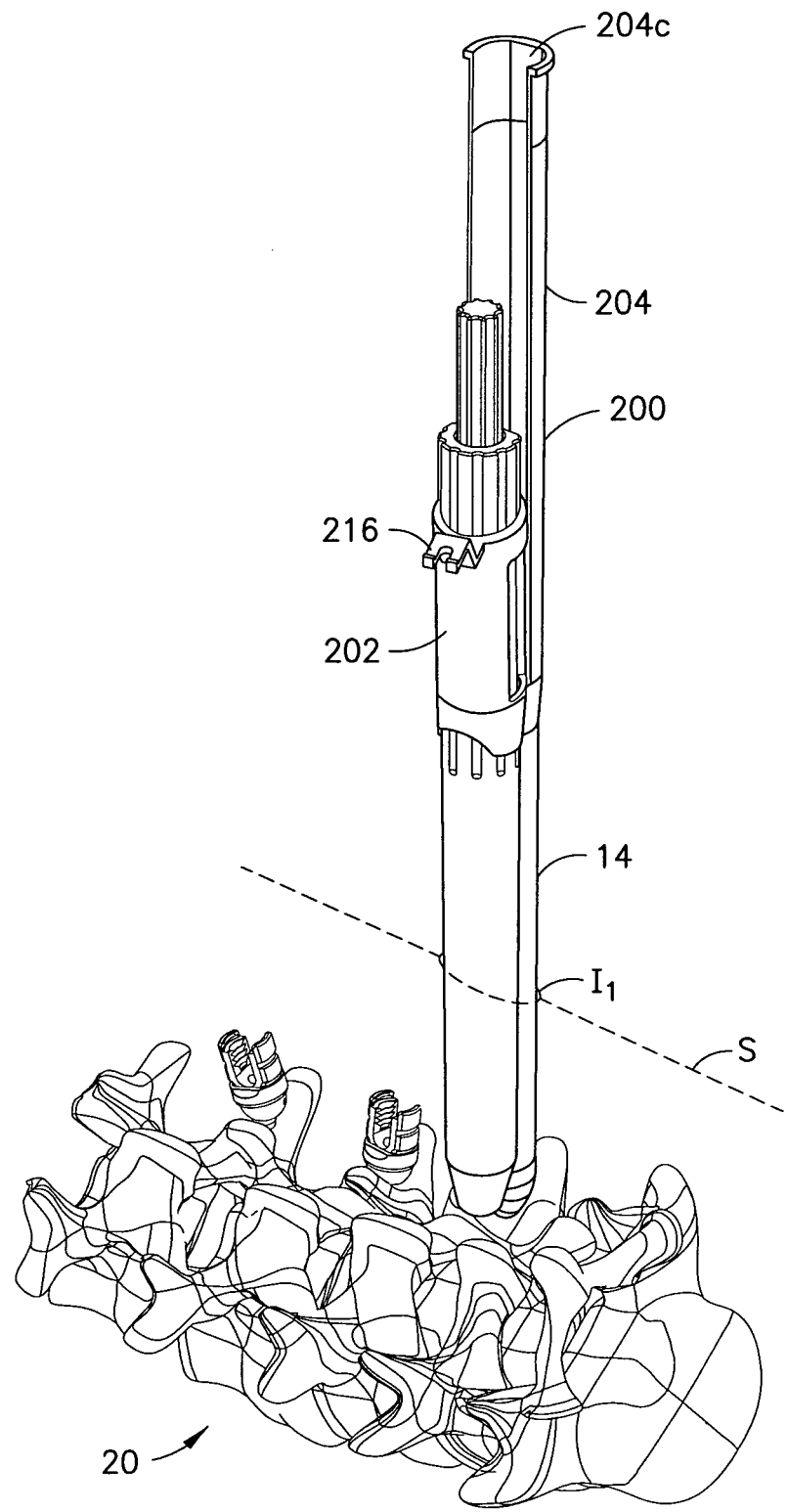
FIG. 14 is view of tubular retractor of the second embodiment shown in FIG. 3 slidingly attached to the second tissue dilator in FIG. 13.
Figure 15:
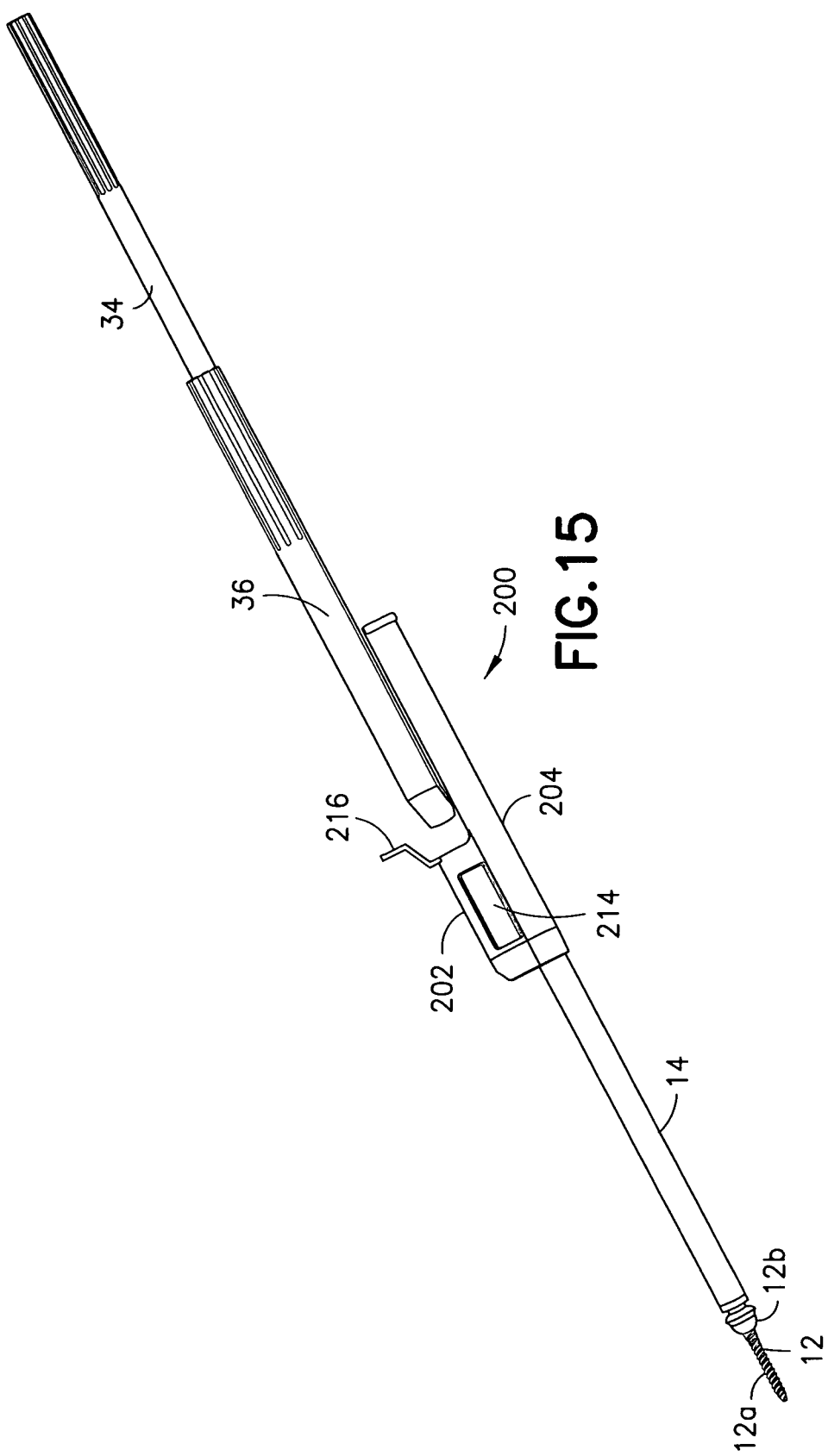
FIG. 15 is a side exploded elevation view of the pedicle screw extension assembly, tissue dilator and retractor as shown in FIG. 13.

Once the tissue has been dilated, tubular retractor 200 may be placed as is illustrated in FIG. 14. Tubular retractor 200 is slid downward in close contact with dilator 36 and screw extension 14 and is manipulated through the skin S and a muscle layers down to the posterior elements of the spine 20. The presence of a tab 216 allows for stabilization of the tubular retractor 200 once fully seated, but also provides the surgeon with an easy handle for pushing down and manipulating tubular retractor 200 through the soft tissues and muscle. FIG. 15 shows the sequential arrangement from the pedicle screw 12 fixed to the vertebral body through the screw extension 14 and tubular retractor 200 and dilators 34 and 36.

Figure 16:
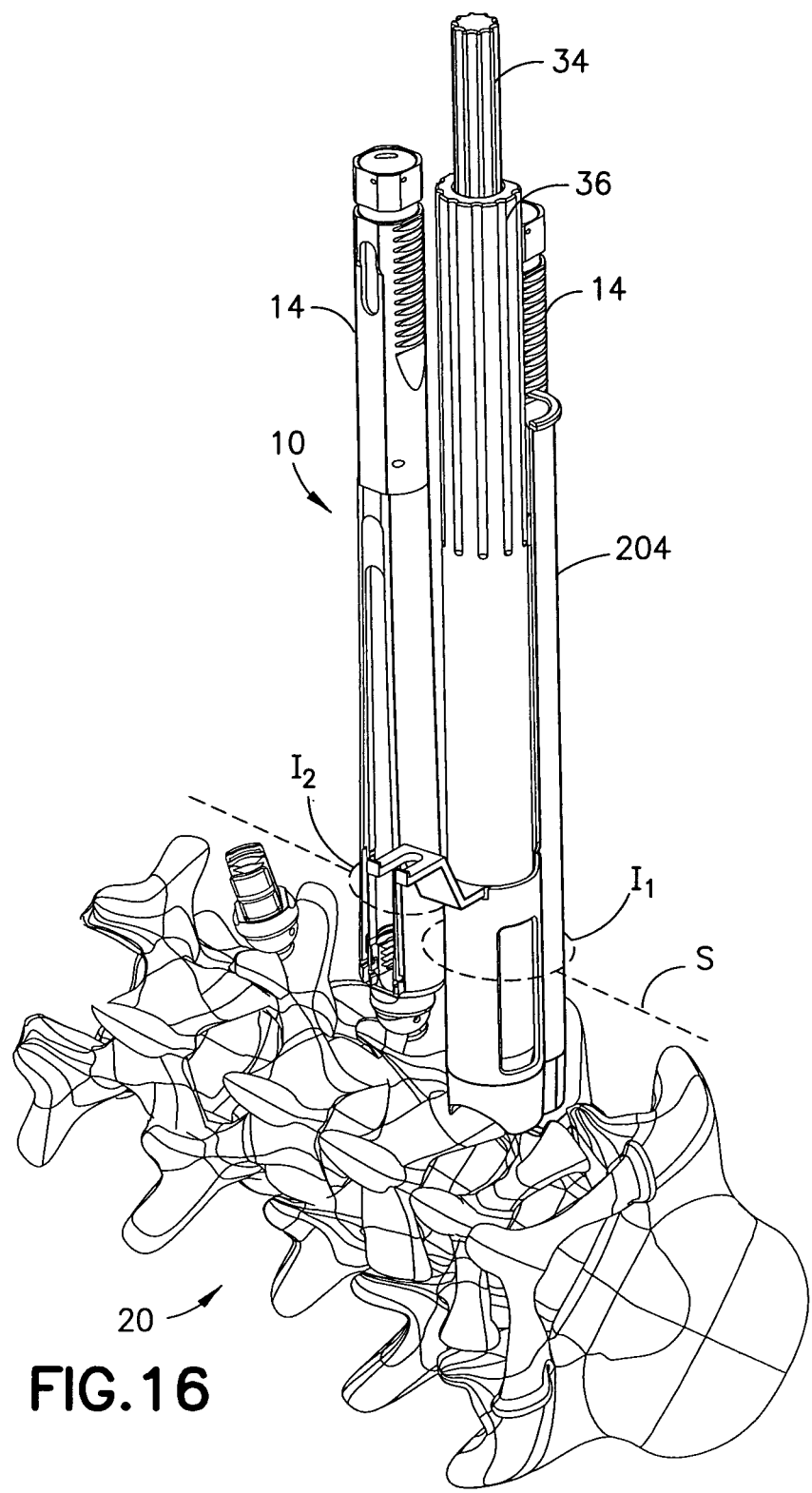
FIG. 16 is a further top perspective view of FIG. 13 showing a second pedicle screw extension assembly extending through tissue of the patient.

At completion as shown in FIG. 16, tubular retractor 200 is placed fully down and seated against the posterior elements of spine 20. At this point, dilators 34 and 36 are removed and an access channel is provided directly to the posterior elements through pathway 210. During placement of tubular retractor 200 over dilator 36 and pedicle screw extension 14 flat interior surfaces 204c of attachment portion 204 engage one of opposing flat surfaces 24 on screw extension 14 thereby keying tubular retractor 200 to screw extension 14 substantially preventing relative rotation therebetween. Because screw extension 14 is attached to multiaxial pedicle screw 12, tubular retractor 200 may be rotated and pivoted about screw shaft 12*a* in order to allow direct visualization and access to the midline elements of spine 20, such as the facet and pars intra-articularis in the medial direction. In addition, tubular retractor 200 may be rotated laterally for direct visualization of the inter-transverse processes.

Figure 17:
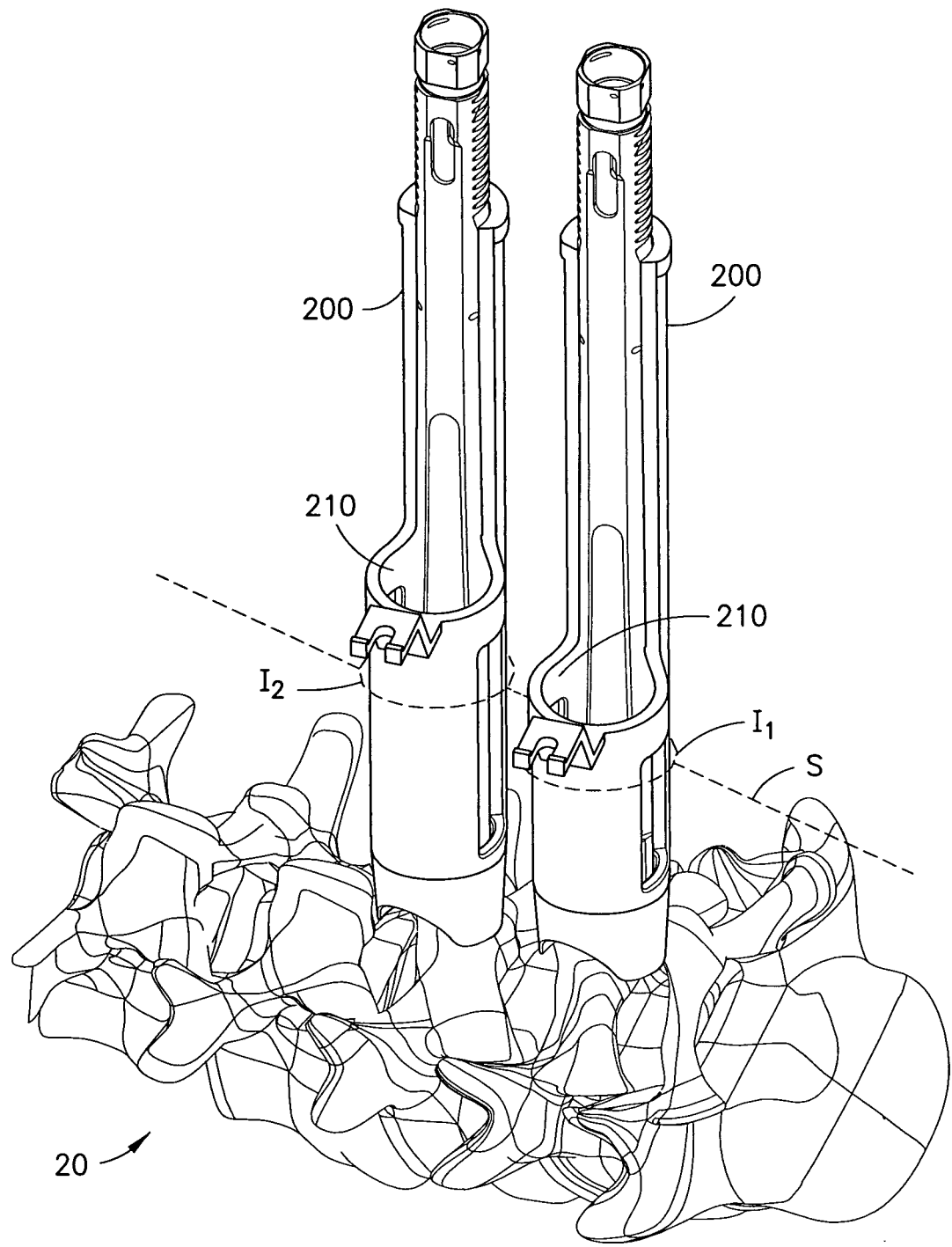
FIG. 17 is a further top perspective view of FIG. 16 with the tissue dilator removed and a second tubular retractor placed over the second pedicle screw extension assembly.
Figure 18:
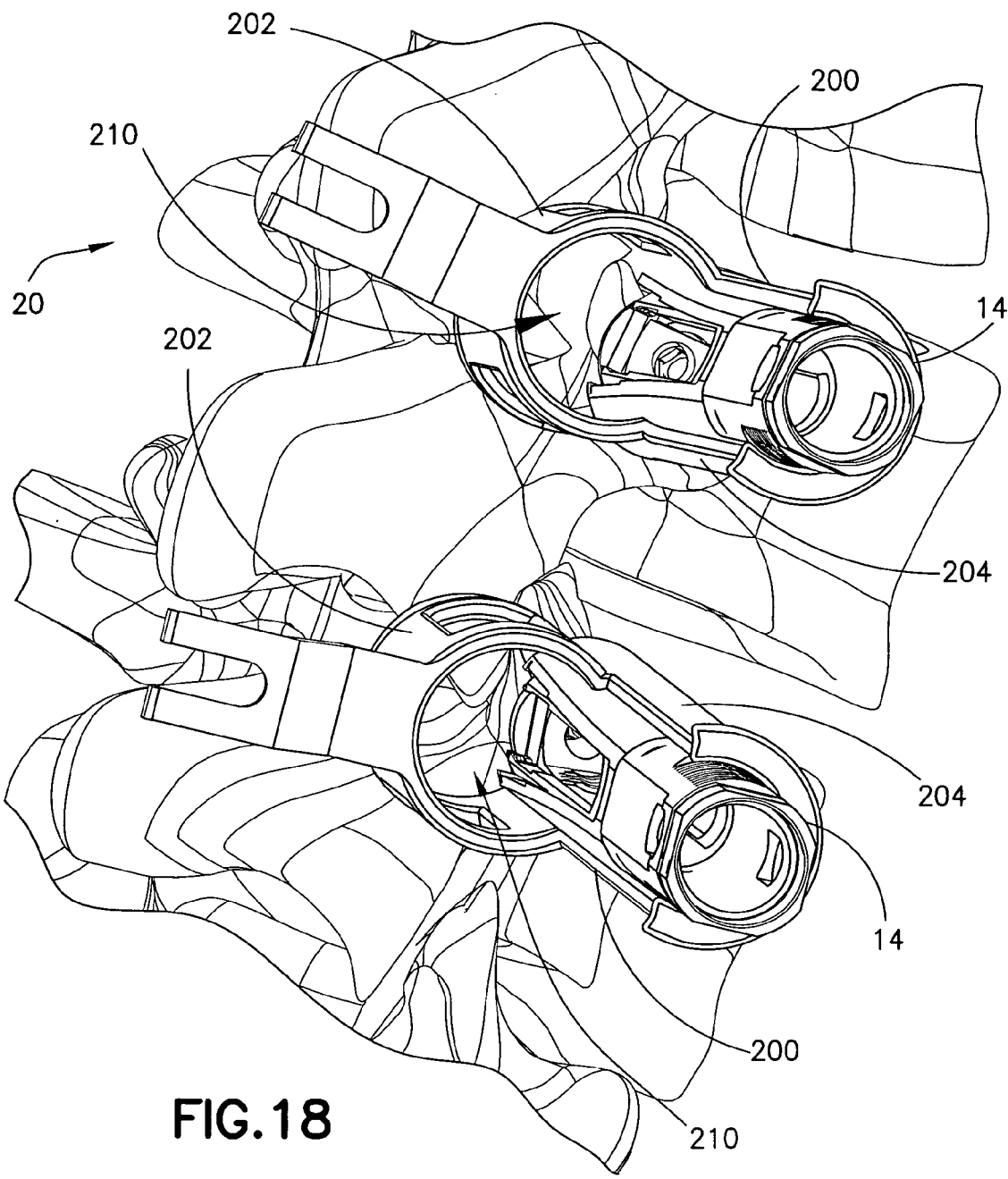
FIG. 18 is an enlarged top view of FIG. 17 is visualized by a surgeon to the access ports of the first and second tubular retractors.

Multiple tubular retractors 200 may be placed in order to provide access to the posterior spinal elements across one or more spinal segments. As shown, for example in FIG. 16, a second small incision $I_2$ may be made through the skin line S and into the tissue of a patient at an adjacent vertebral level of spine 20. A second pedicle screw extension assembly 10 may be placed through incision $I_2$ with pedicle screw 12 threadedly attached to the pedicle 16 of the adjacent vertebral body 18 in the same manner as the attachment of the first pedicle screw extension assembly 10. Likewise a second tubular retractor 200 as shown in FIG. 17 may be slid downward in close contact with a dilator 36 and screw extension 14 and manipulated through the skin S and muscle layers down to the posterior elements of the spine 20 as with first tubular retractor 200. Different sized tubular attractors 200 are shown placed in the regions adjacent to the posterior spinal elements. A top view as shown in FIG. 18 demonstrates the visualization of the spinal elements through the tubular retractors 200 as would be seen by the surgeon. There are multiple sizes of tubular retractors 200 that would be available based on the working space required and the anatomy of the patient and thickness of overlying soft tissues of muscle in the region.

Figure 19:
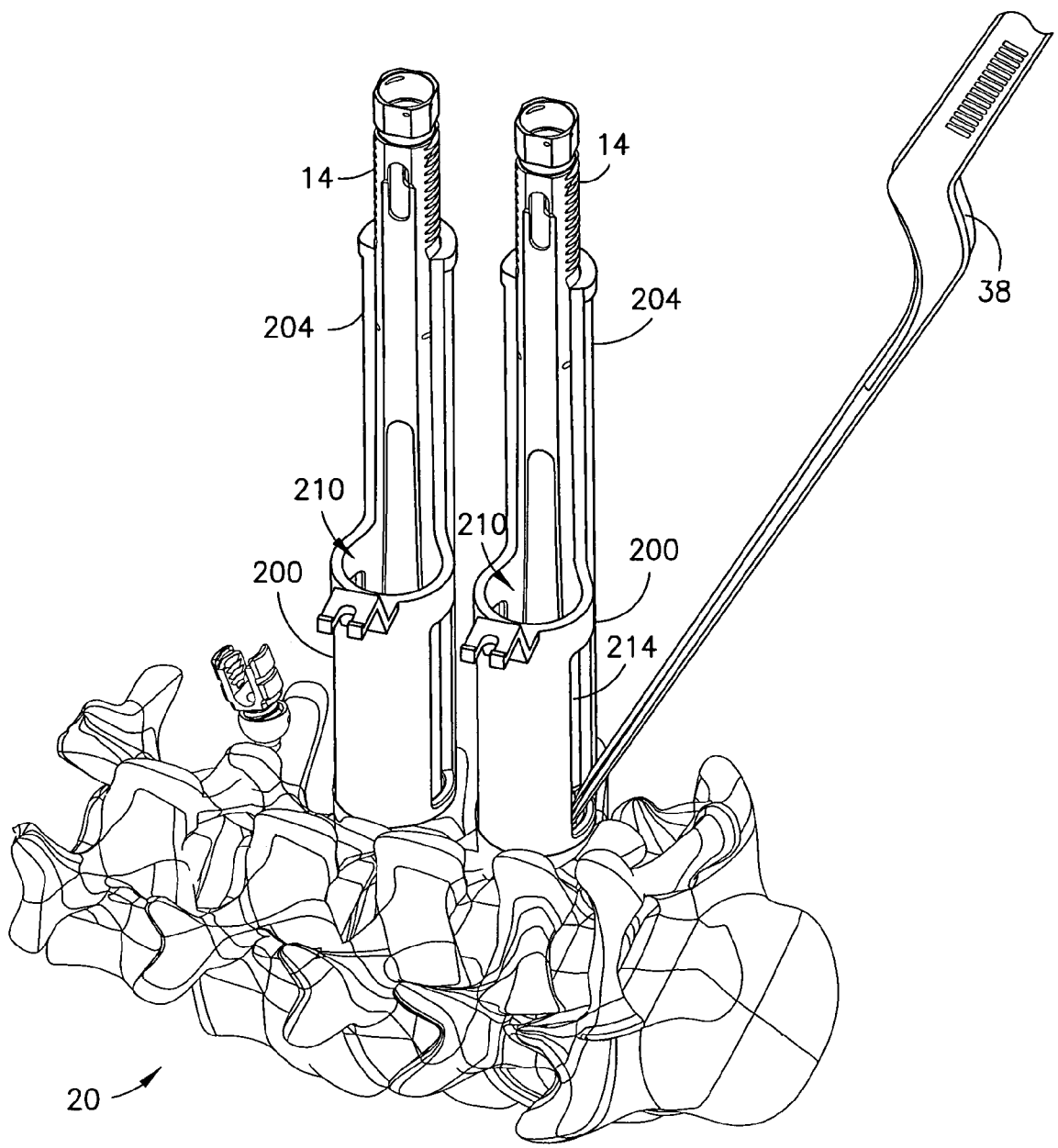
FIG. 19 is a top perspective view of FIG. 17 showing use of an electrocautery device placed directly through a side window of one tubular retractor.

Once tubular retractor 200 has been placed and a visualization pathway is provided down to the posterior spinal elements of spine 20, the next step in the procedure is to remove soft tissues overlying the bony structures. FIG. 19 shows use of an electrocautery device 38 for removal of overlying soft tissues and blood vessel cauterization with the tip of electrocautery device placed directly through side window 214. The soft tissues must be removed prior to bony preparation necessary for securing bleeding decorticated bone along the spinal elements required for achieving spinal fusion. While an electrocautery device 38 is shown, other instruments such as rongeurs and curetttes may also be used to efficiently remove overlying soft tissues under direct visualization by the surgeon.

There are multiple means by which the surgeon may choose to visualize the working space though pathway 210 and to provide for access by the instruments for soft tissue removal and bony preparation. For example, an operative microscope may prove useful for visualization and navigation during the surgical procedure. A surgeon may utilize operative loops that provide for magnification and direct illumination by way of a light source that is fixed to the surgeon's forehead. Finally, a separate endoscopic camera system may be used for illumination and visualization, where the small tubular endoscope would be placed down the working pathway 210 and visualized on a separate monitor within the operating suite.

Figure 20:
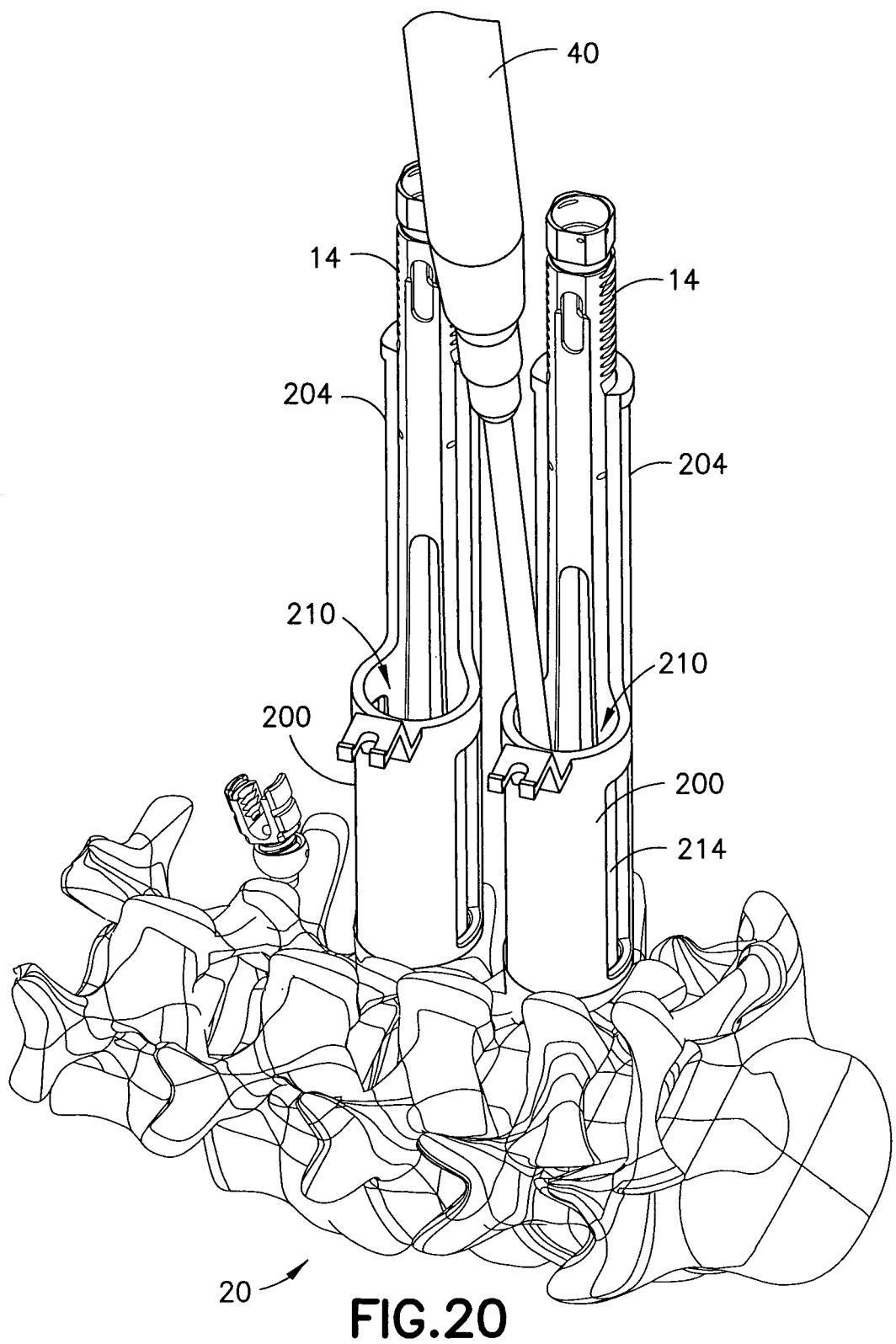
FIG. 20 is a top perspective view of FIG. 17 showing a powered drill placed directly through the pathway of the access port of one tubular retractor.
Figure 21:
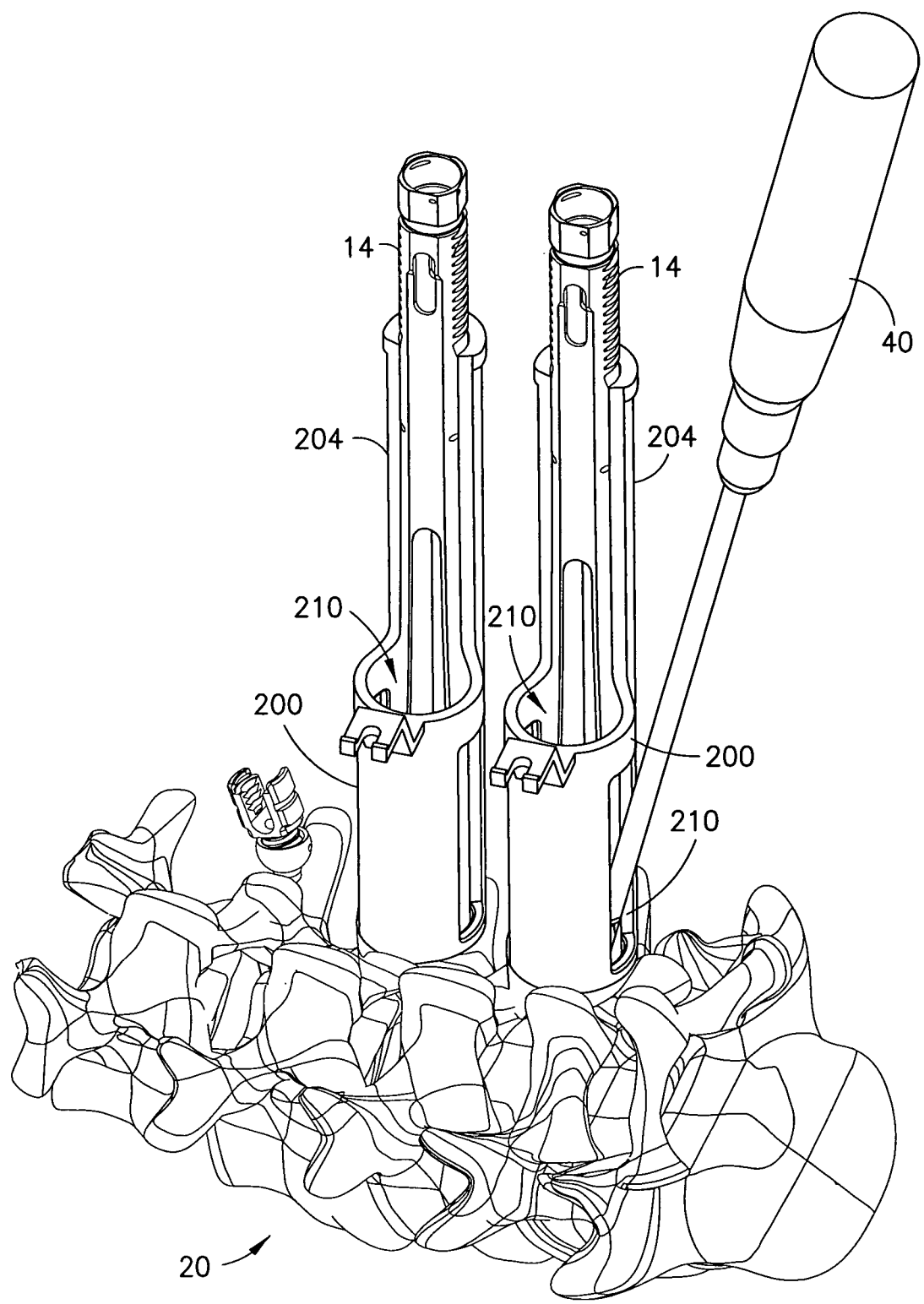
FIG. 21 is a top perspective view of FIG. 17 showing use of a power drill placed directly through a side window of one tubular retractor.

Instruments may be placed by way of a number of access corridors. FIG. 20 shows a powered drill 40 or burr for controlled preparation and removal of the bone. Drill 40 is placed directly through pathway 210. In FIG. 21 drill 40 is placed through one of the side windows 214 while the surgeon directly visualizes its operation through the pathway 210 of tubular retractor 200.

One of the primary advantages of system 1 is the ability to balance control with a wide range of orientation and access corridors for addressing the adjacent bony elements, both medial (facet, pars interarticularis, lamina) and lateral (transverse processes). Having multiple degrees of freedom provided by the multiaxial pedicle screw 12 provides the surgeon with variations in orientation that are desirable to adequately decorticate the surrounding bony elements prior to graft placement for spinal fusion.

Once the adjacent soft tissues have been removed and the posterior bony elements have been decorticated to expose bleeding bone, the next step is for the surgeon to deposit a suitable bone graft on the prepared bony surfaces. In some cases, it may be adequate simply to place bone graft around the decorticated facet joint to fuse the facet joint. Bone graft material may be placed through a side opening, such as one of windows 214, or through pathway 210 of tubular 200. Facet fusion can provide for some enhanced stability alone or in combination with an interbody spinal fusion. However, in many cases the facet joint on one side of the spine will have been removed in order to allow for passage of an interbody implant. Fusion of the contralateral facet joint alone may provide some benefit, but creation of a bridging bony fusion across two spinal segments on both sides of the spine provides for a more robust and conventional posterior lateral spinal fusion.

Figure 22:
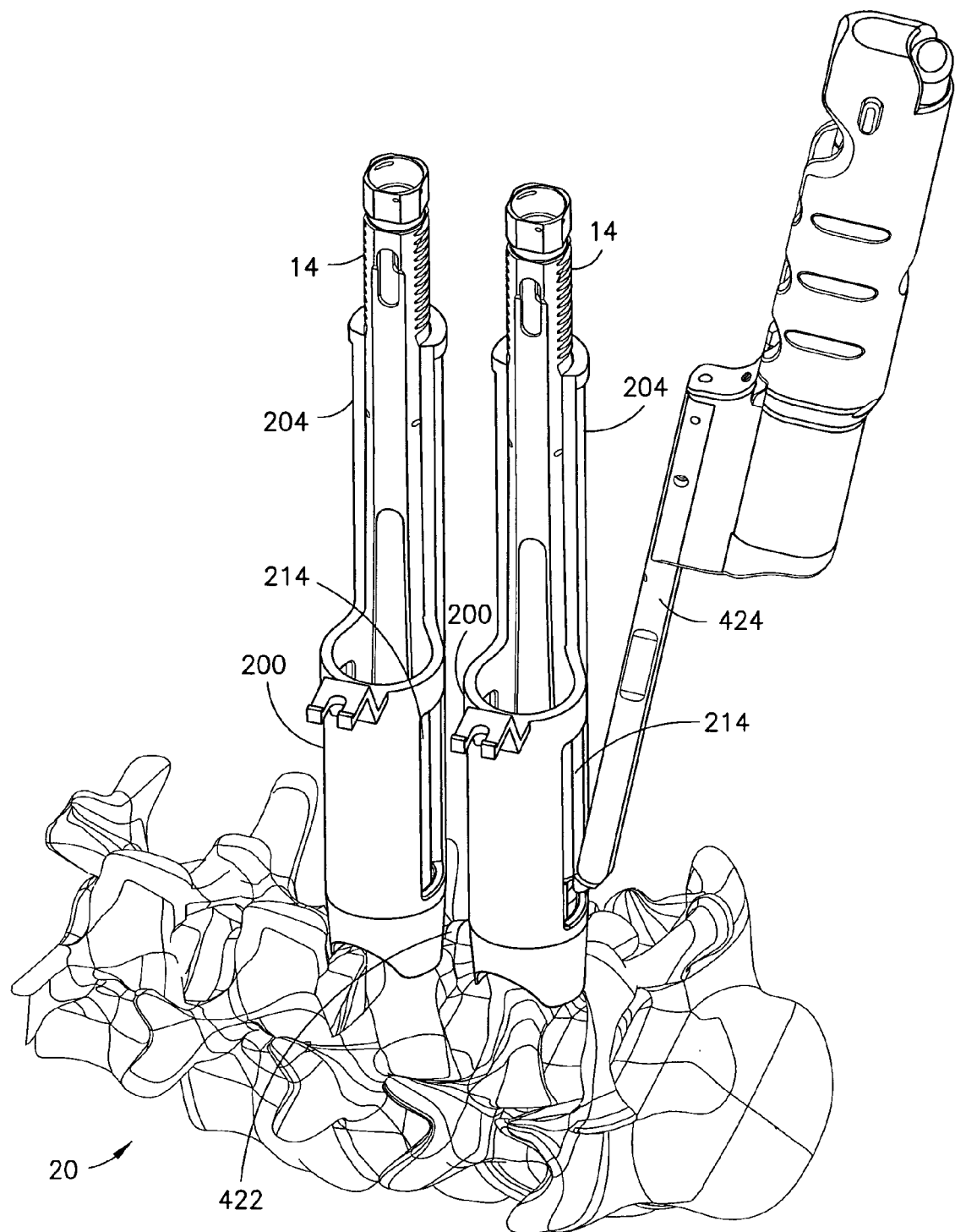
FIG. 22 is a top perspective view of FIG. 17 showing a blunt dilator attached to and introducer with the blunt dilator being placed through side opening window of one tubular retractor.

In the case where such as a bridging fusion is desired, a dilator, such as blunt dilator 422 described hereinabove with reference to FIGS. 9-10 may be affixed to the an introducer, such as introducer instrument 424 to create a subcutaneous passageway through tissue between the two spinal segments. FIG. 22 shows the placement of blunt dilator 422 through side opening window 214 of tubular retractor 200. It should be appreciated, however, that tubular retractors 400 and 500 as described hereinabove may also be used in the placement of blunt dilator 422 for creating the subcutaneous passageway. Blunt dilator 422 may be placed under direct visualization and then pushed through the soft tissue passageway until it extends into window 214 of the second tubular retractor 200.

FIG. 22 demonstrates the use of multiposition introducer instrument 424 that allows for placement of blunt dilator 422 at multiple orientations. Initially, blunt dilator 422 may be placed in a nearly vertical orientation through incision $I_1$ down along the sides of the screw extension 14 and into window 214 of tubular retractor 200. Once blunt dilator 422 contacts the posterior bony elements of spine 20 it may be rotated into a 90 degree orientation and pushed subcutaneously across the passageway between the two spinal elements. Multiple sizes of blunt dilators 422 may be used in a progressive manner to safely and gently dilate the tissues between adjacent spinal levels.

Following creation of the tissue passageway between spinal segments, there are number of graft material options that could be useful for bridging the spinal elements, such as those shown in FIGS. 23-31. As described further below, these graft material options include a cylindrical and pliable bone or synthetic graft material tube. The cylindrical graft may be solid, hollow or partially open and can be used to contain an injected graft material, for example. Graft implant designs may also include a more rigid cortical bone, a pliable cancellous bone plug, or synthetic graft material shape to mimic the spinal curvature and provided with a channel and outlets for injection of flowable graft material two fully fill the variable anatomy around the graft implant. Further, a series of sleeves that are pliable and perforated could be placed in a manner analogous to placement of a cardiovascular or urologic stent.

Figure 23:
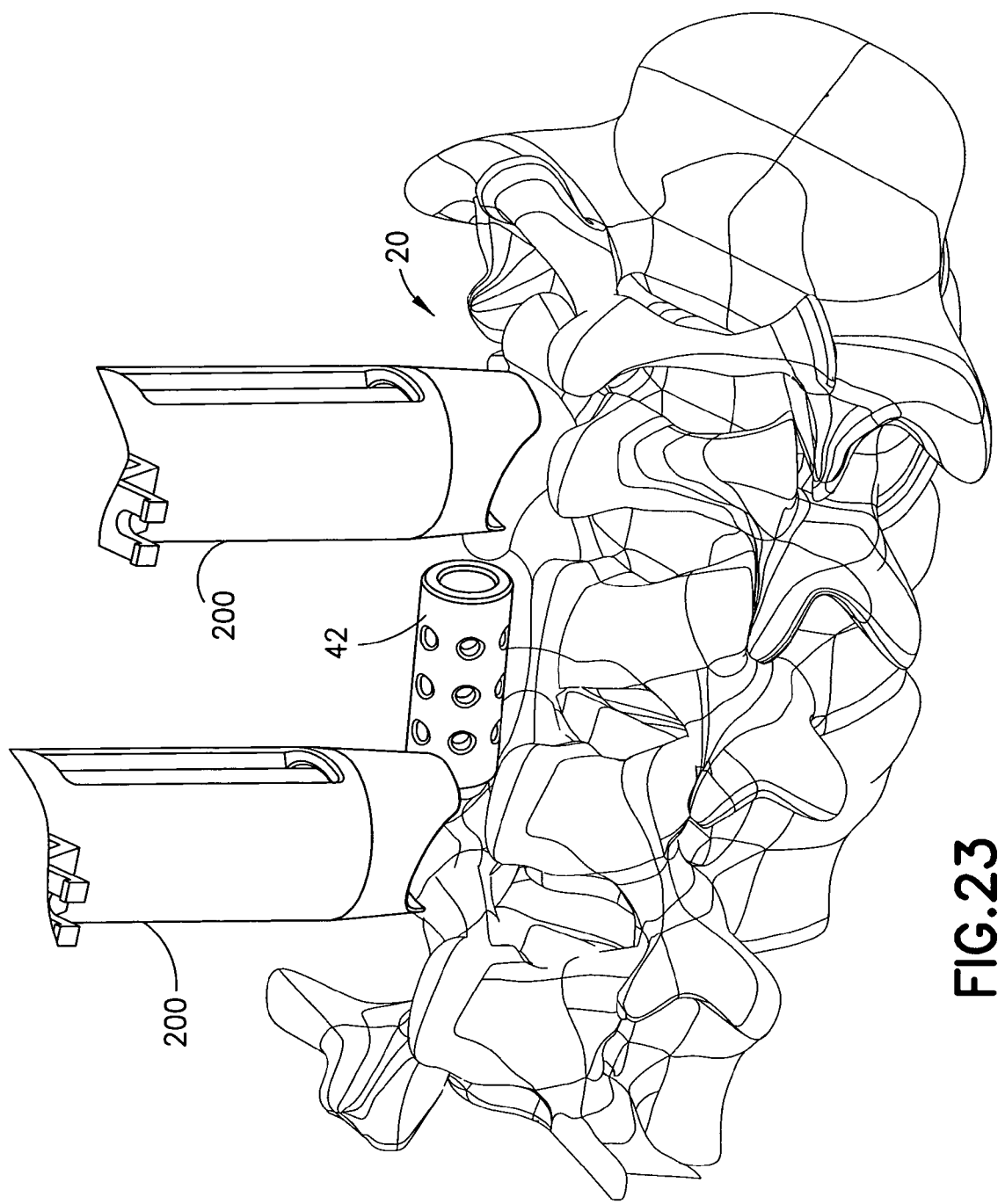
FIG. 23 is an enlarged top perspective view of FIG. 17 showing placement of a hollow perforated graft between spinal elements.
Figure 24:
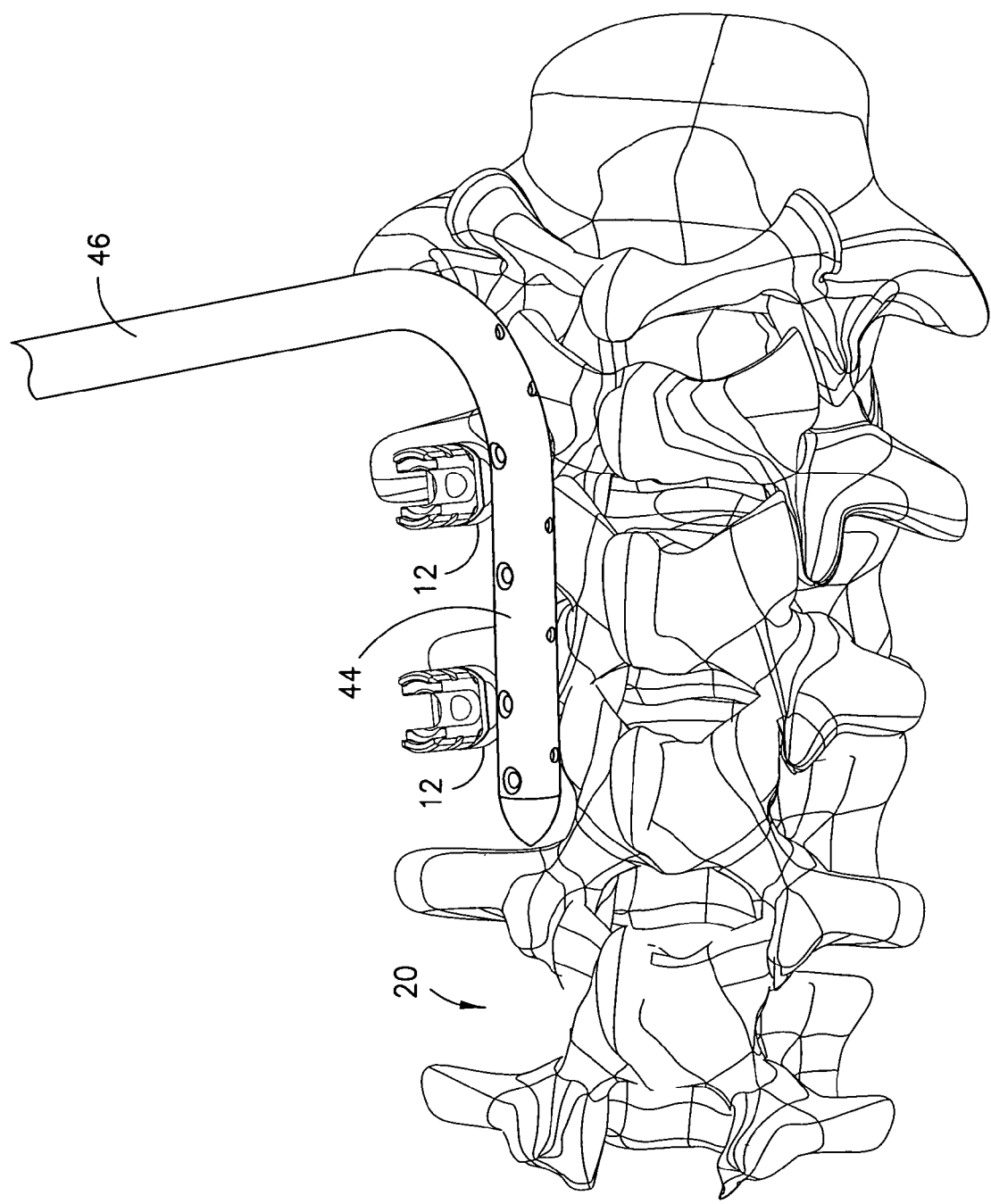
FIG. 24 is a view similar to the view of FIG. 23 showing an alternative perforated tube placed between spinal elements for graft material delivery.

FIG. 23 shows placement of a hollow perforated graft 42 that may allow for a bony incorporation and act as a pathway and scaffold for placement of additional fusion-facilitating materials. Alternatively, a perforated tube 44 could be placed as shown in FIG. 24 (without showing retractors 200 for clarity) allowing for injection of a biomaterial capable of securing bridging spinal fusion. This perforated tube 44 may be removed after placement of the fusion material. Once the tissue passageway is bridged with tube 44, a long cannula 46 may be used for injection of a flowable bone graft substitute. Such flowable bone graft material may include a synthetic hardening bone graft substitute that would set and provide for the appropriate rigidity and stabilization to secure spinal fusion.

Figure 25:
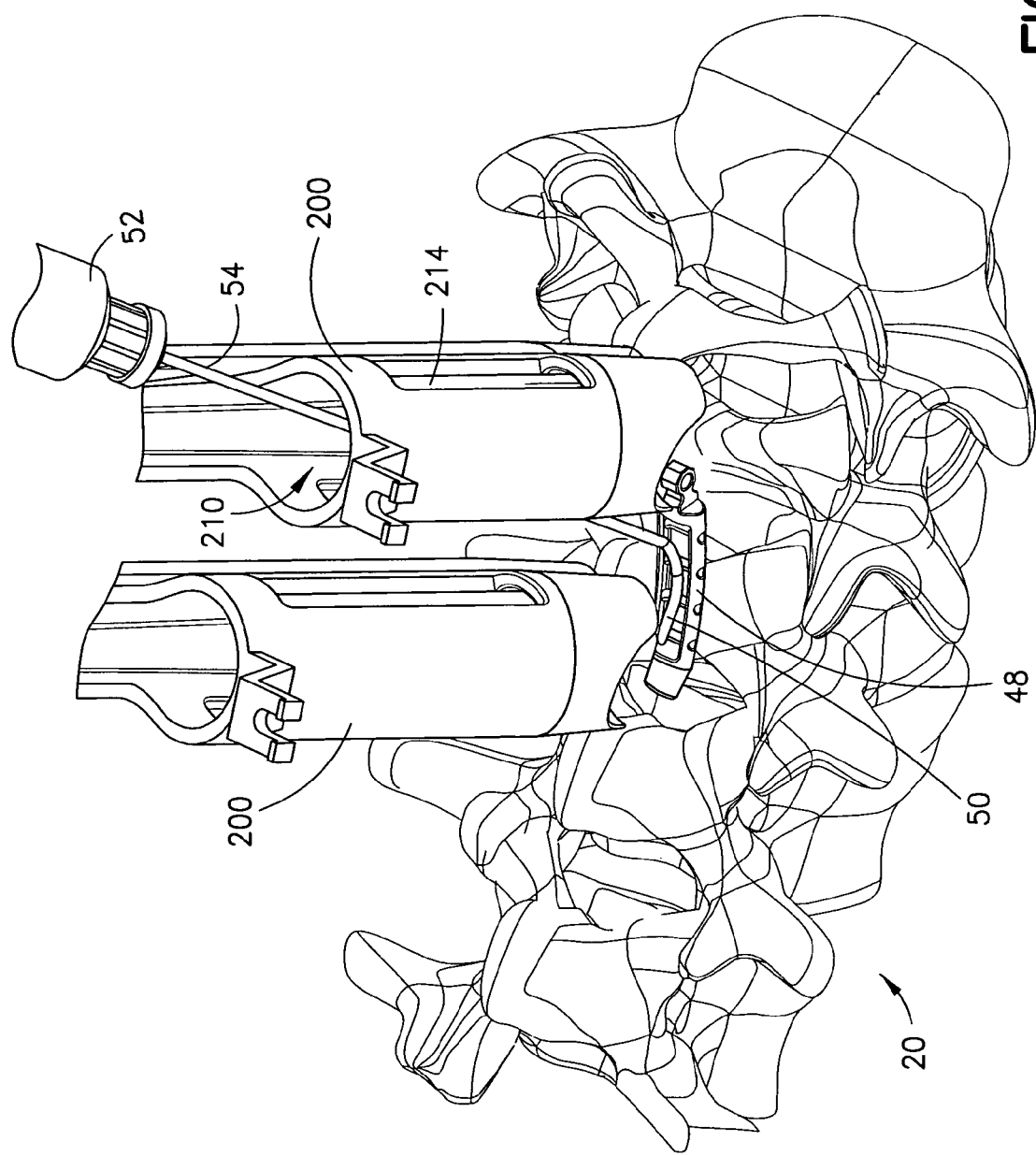
FIG. 25 is a view similar to the view of FIG. 23 showing an alternative manufactured perforated anatomical implant followed by injection of flowable biomaterial.

A manufactured perforated anatomical implant 48 is shown in FIG. 25. Implant 48 may be fabricated from metal, polymer, ceramic, or a natural material such as allograft bone. Implant 48 would help to maintain the tissue passageway previously created, while providing a scaffold onto which and into which injectable biomaterial could be delivered. Following placement of implant 48 across the spinal segment, additional spinal fusion-enabling material 50 may be placed with direct visualization by an injector 52 through pathway 210 of tubular retractor 200. FIG. 25 demonstrates this method of perforated implant delivery followed by flowable biomaterial injection. The flowable biomaterial could be one of many options available to surgeons. It may involve a setting artificial ceramic material, or could involve the use of a slurry of morselized autograft or allograft or bone marrow aspirate containing mesenchymal stem cells, all capable of injection by way of relatively small diameter cannula 54, as shown.

Figure 26:
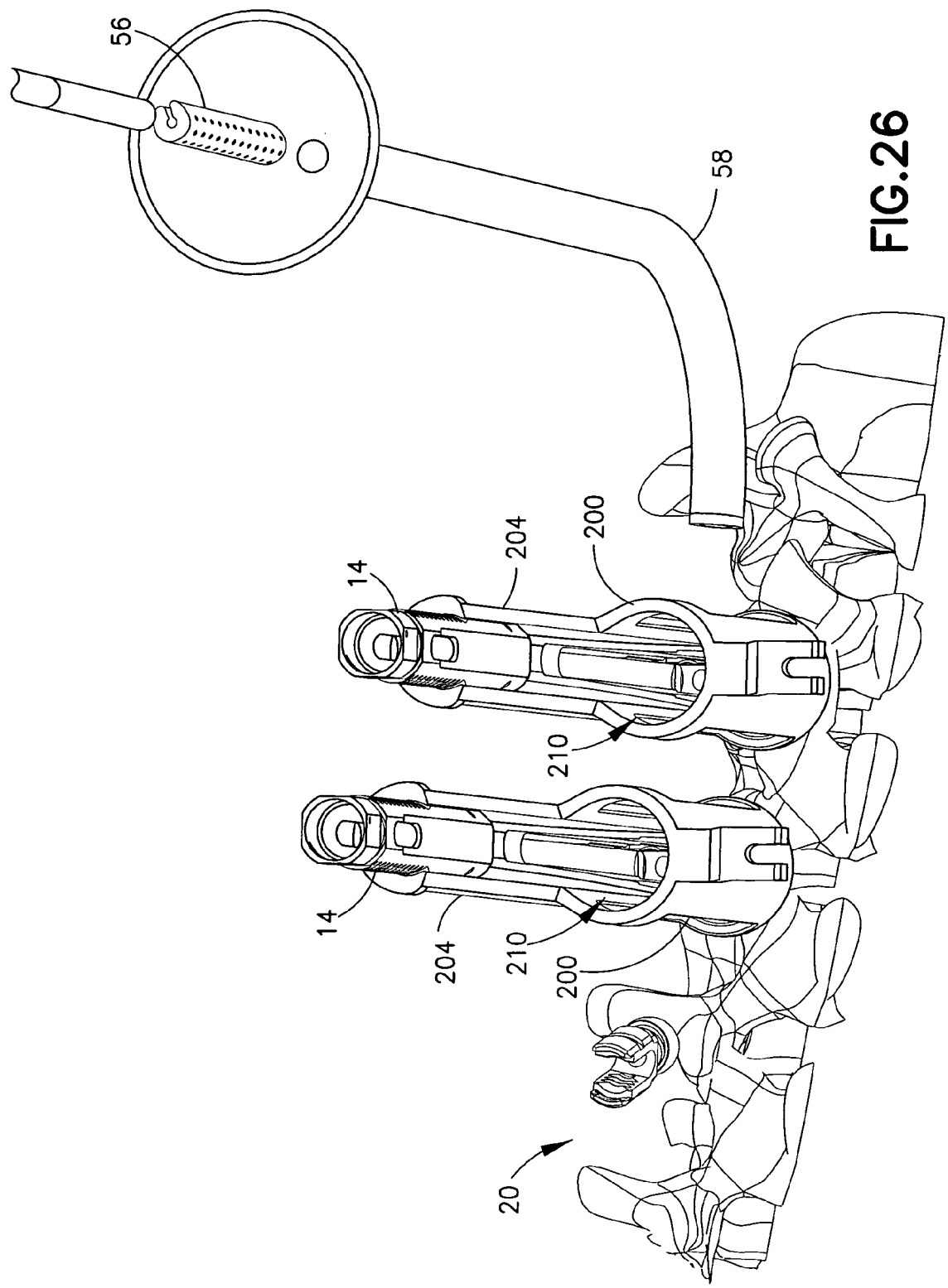
FIG. 26 a is a view similar to the view of FIG. 23 showing an alternative flexible and perforated tubular implant being pushed along a curved rigid access tube.
Figure 27:
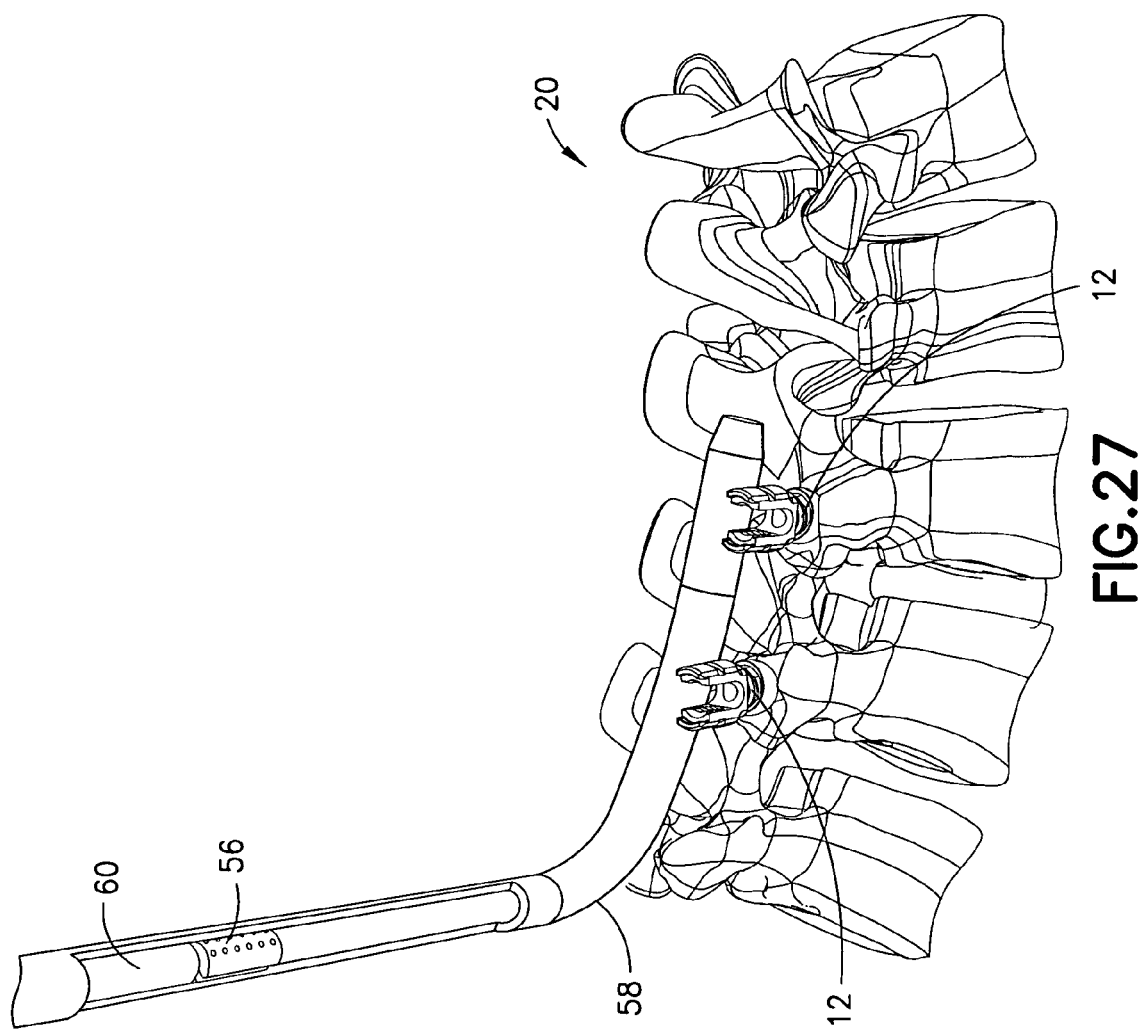
FIG. 27 is a view similar to the view of FIG. 26 with tubular retractors removed for clarity and with the curved rigid tube in partial cross-section to reveal the tubular implant in the process of being delivered to the spine.
Figure 28:
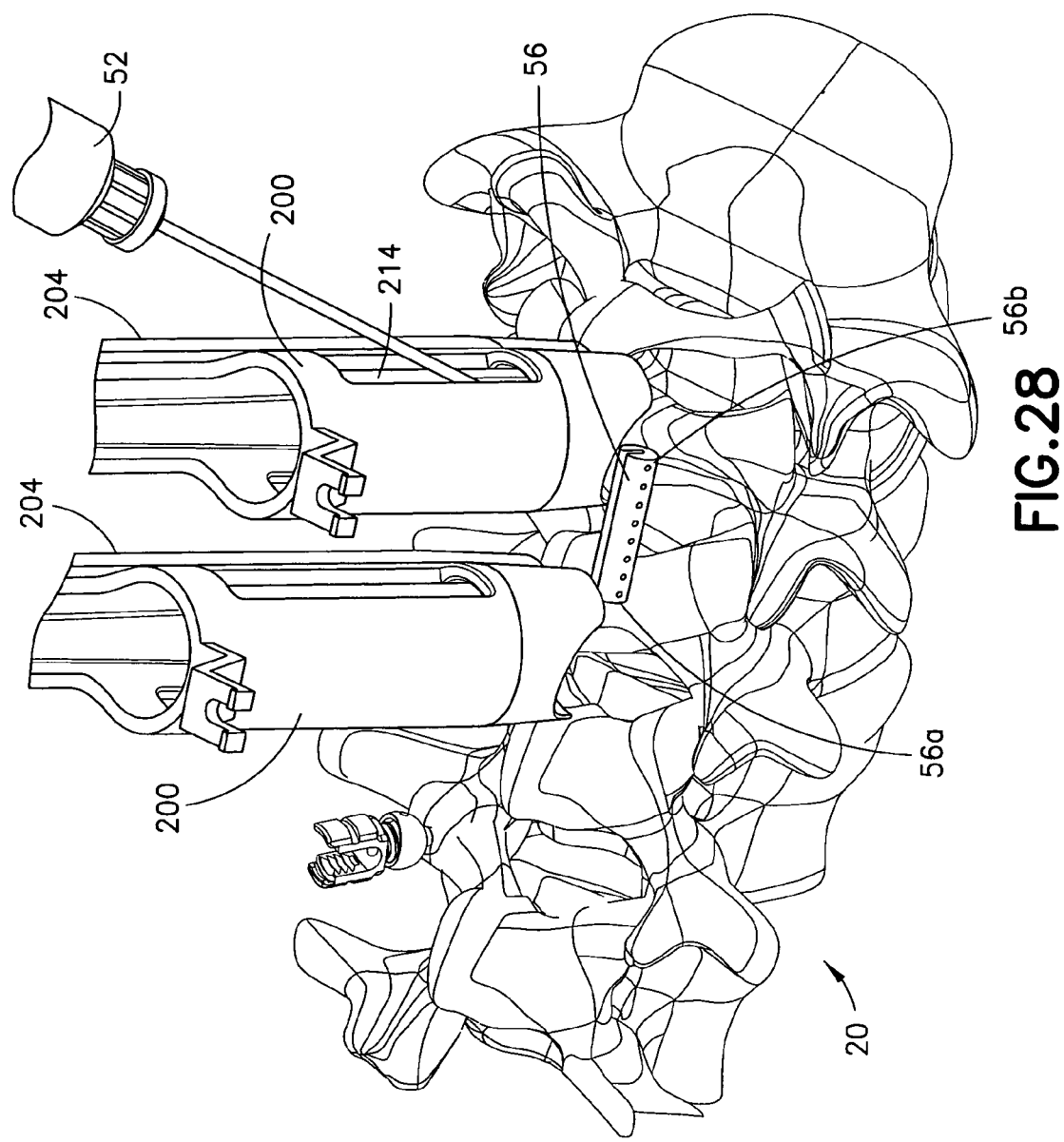
FIG. 28 is a further view of FIG. 27 with tubular retractors in place showing additional bone graft material being injected around the tubular implant.
Figure 29:
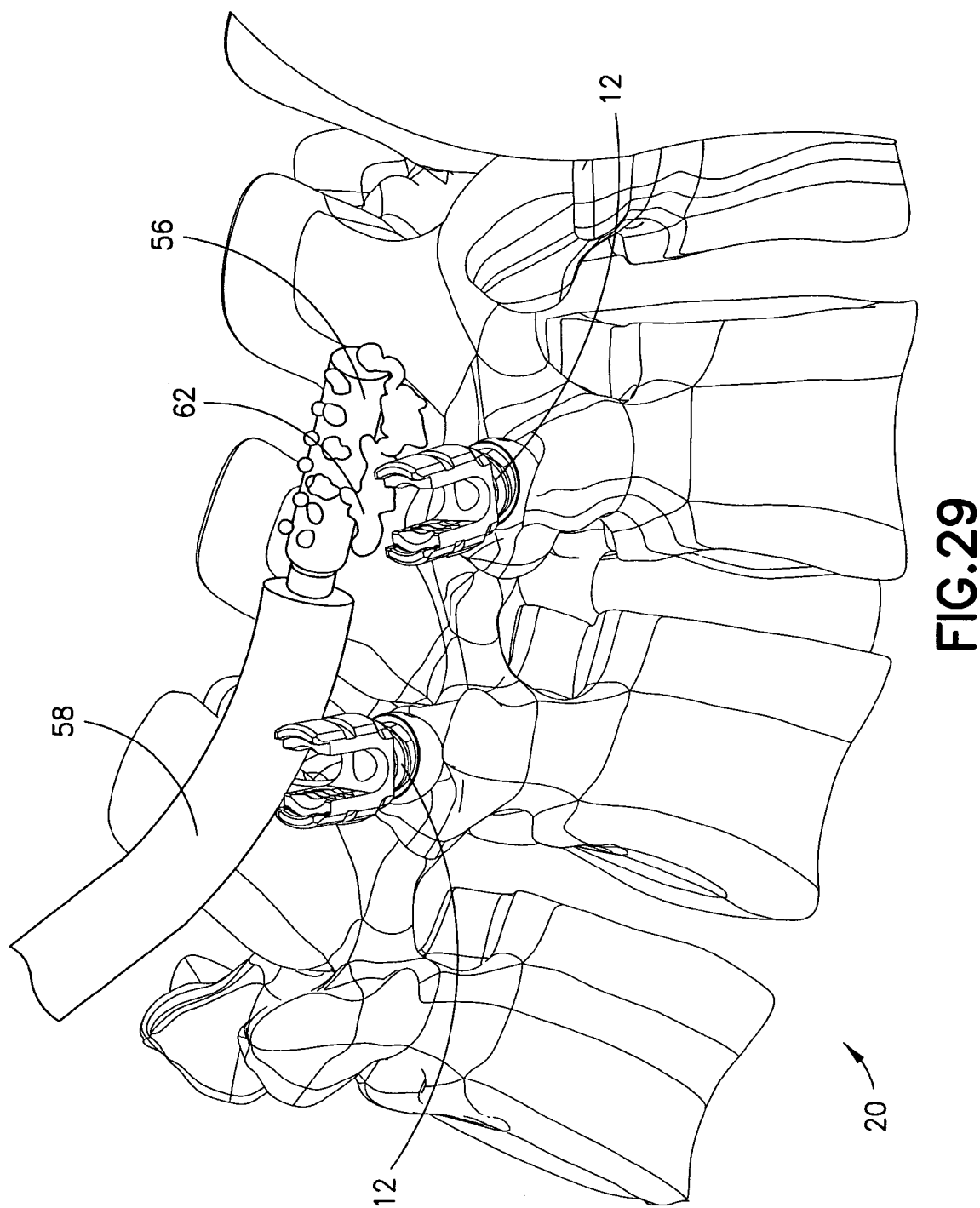
FIG. 29 is a further view of FIG. 28 showing some of the injected graft material surrounding the previously placed tubular implant.

Alternatively, a flexible and perforated tubular implant 56, as shown in FIGS. 26-27 may be used. This implant could be a synthetic biomaterial or an allograft or autograft plug of cancellous bone. Demineralization of the bone would render it more pliable if needed for insertion down the cannula. In this case, implant 56 is pushed along a curved rigid access tube 58 into the space between the spinal levels. Access tube 58 is placed in the space between the spinal elements as visualized through pathways 210. Curved access tube 58 allows for deposition of implant 56 through a trajectory necessary for bridging spinal elements adjacent two spinal screws 12, as depicted in FIG. 27 showing implant 56 in the process of being delivered to the spine. A flexible tamp 60 is used to push flexible implant 56 into place. Flexible implant 56 may be fabricated, for example, of a partially demineralized cancellous (spongy) bone machined into a semicircular shape and perforated. Once implant is expelled from access tube 58 and is in place flowable biomaterial may be injected. FIG. 28 shows additional bone graft material (such as a ceramic hardening cement or bone marrow aspirate) being injected by injector 52 around implant 56 for an enhanced fusion bed as well as better anchorage of implant 56 at its two opposite ends 56a and 56b. FIG. 29 shows some of the injected graft material 62 surrounding the previously placed implant 56. Biomaterial 62 may be injected into and around the perforated implant 56 as shown in FIG. 29 to provide for more surface area, more graft volume, and enhanced anchorage of the implant in the region in which the posterolateral spinal fusion is desired.

Turning now to FIGS. 30-35 an alternative technique for placing a graft implant such as flexible implant 56 is described, with particular reference to tubular retractor 500, as described hereinabove with respect to FIG. 11. As described, tubular retractor 500 may be used for placement of implant 56 between adjacent spinal levels. Opening 514a at the distal end 500a of tubular retractor 500 allows for initially placing implant 56 in a 90° orientation (to the skin line S) and then rotating it 90° into position between the distal forks 502a and 502b and pushing it down to the prepared bony surfaces through openings 514a in a manner analogous to the minimally invasive insertion of the connecting rod described in the '640 patent.

Figure 30:
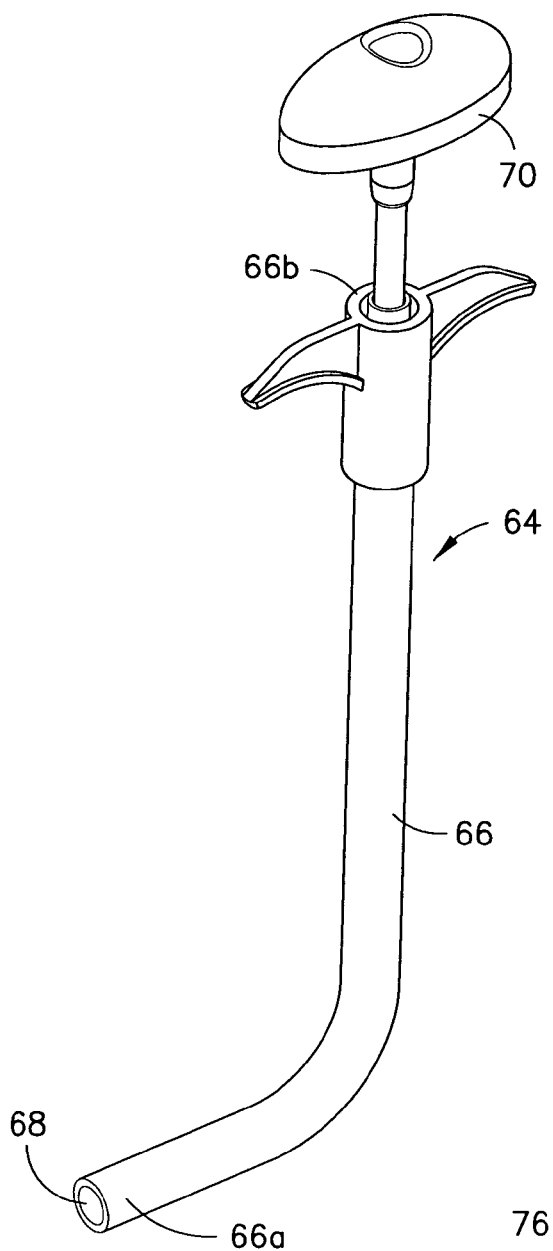
FIG. 30 is a perspective view of a self-contained delivery device for holding and delivering the tubular implant of FIG. 26.

A self-contained delivery device 64 for holding and delivering implant 56 is shown in FIG. 30. Device 64 allows for preloading implant 56 (not shown) into a delivery device outer sheath 66 through an opening 68 at the distal end 66a. Once implant 56 has been loaded the implant 56 may be placed in position between two spinal elements and a plunger 70 at the proximal end 66b is pushed downwardly in order to displace the implant 56 into the previously created tissue passageway between the vertebral elements.

Figure 31:
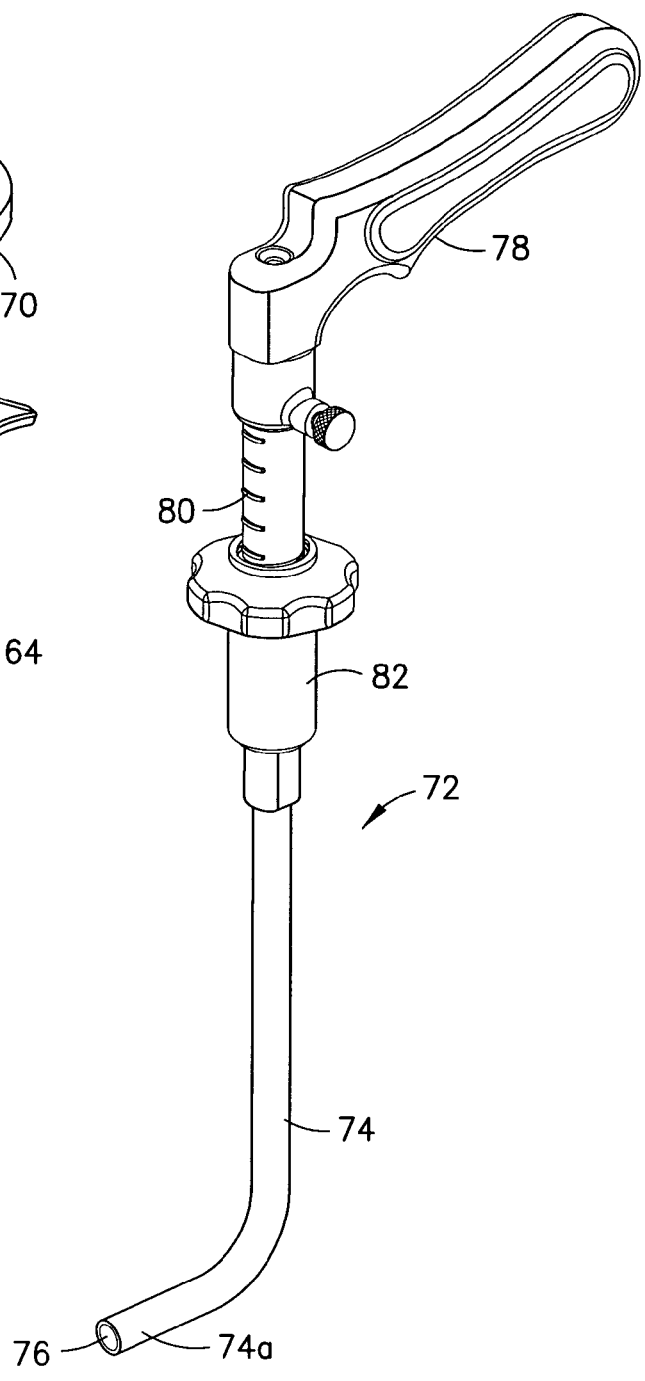
FIG. 31 is perspective view of another device for more controlled delivery of the tubular implant of FIG. 26.
Figure 32:
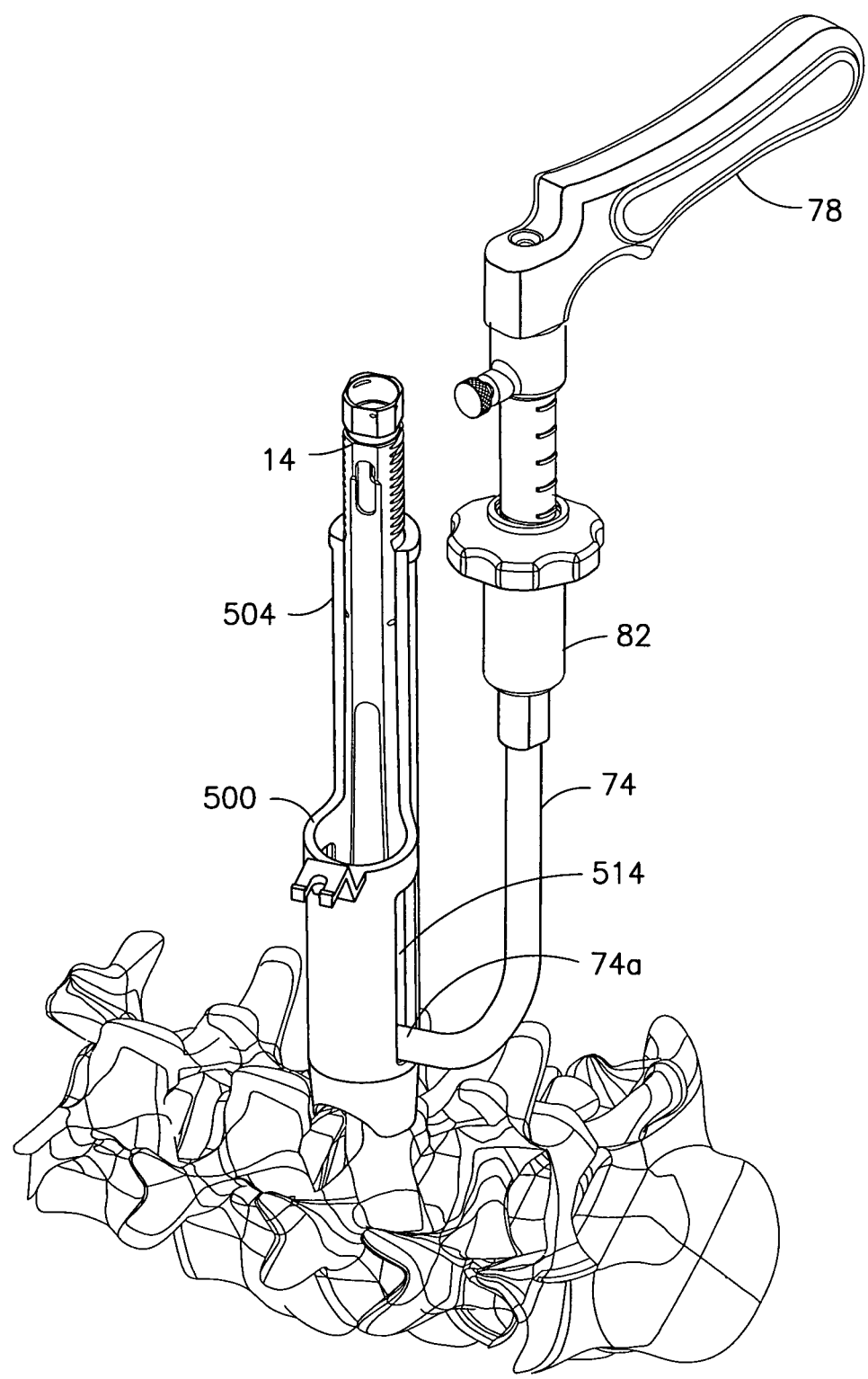
FIG. 32 is a further view of the delivery device of FIG. 31 showing the distal end of an outer sheath of the delivery device extending through a side window of a tubular retractor.

A delivery device 72 for more controlled delivery of implant 56 is shown in FIG. 31. Device 72 like device 64 allows for preloading implant 56 (not shown) into a delivery device outer sheath 74 through an opening 76 at the distal end 74a. Distal end 74a is configured and sized to extend into windows 514 and across tubular retractor 500, as shown in FIG. 32. Once implant 56 has been loaded into outer sheath 74, distal end 74a may be placed through windows 514 for positioning implant 56 between two spinal elements. In this case, a rather large handle 78 is provided for the surgeon for stabilization and orientation of delivery device 72. A screw thread 80 allows for controlled withdrawal of a collar 82 that will draw outer sheath 74 back and expose implant 56 once it has been docked into the desired location between the spinal elements.

Figure 33:
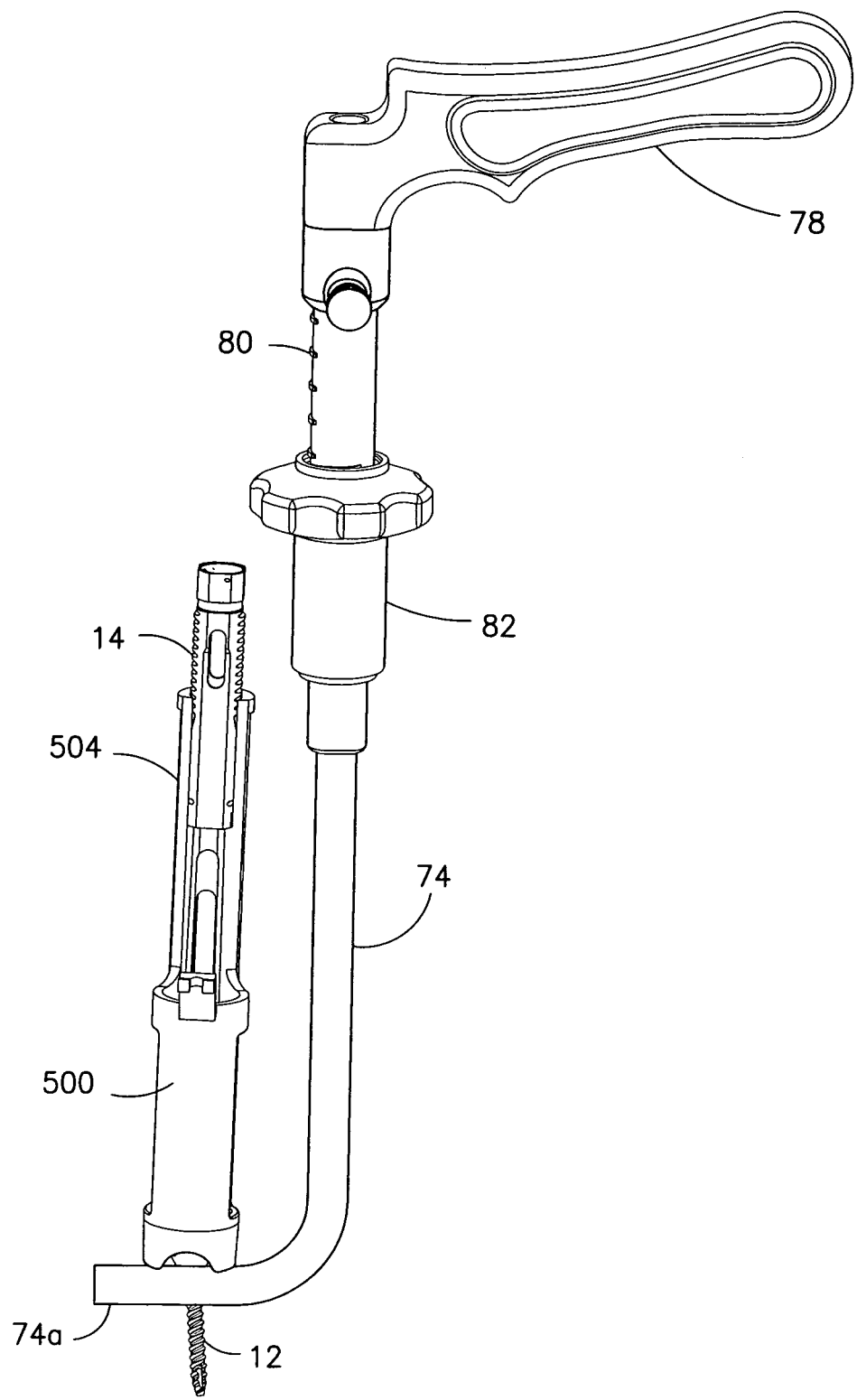
FIGS. 33 and 34 show the process of withdrawing the outer sheath of the delivery device of FIG. 32 and leaving the tubular implant behind on the spinal elements.
Figure 34:
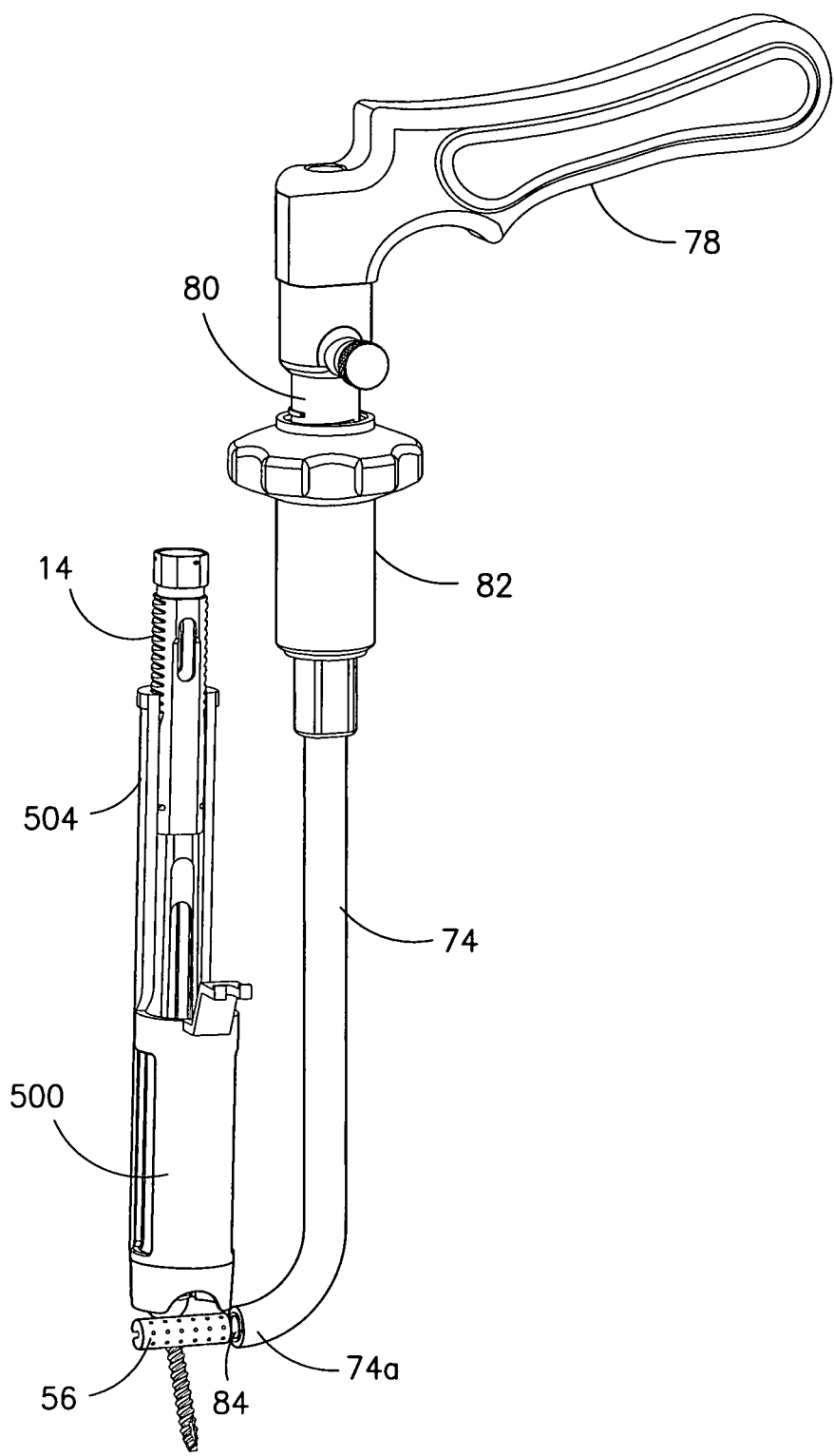
Figure 35:
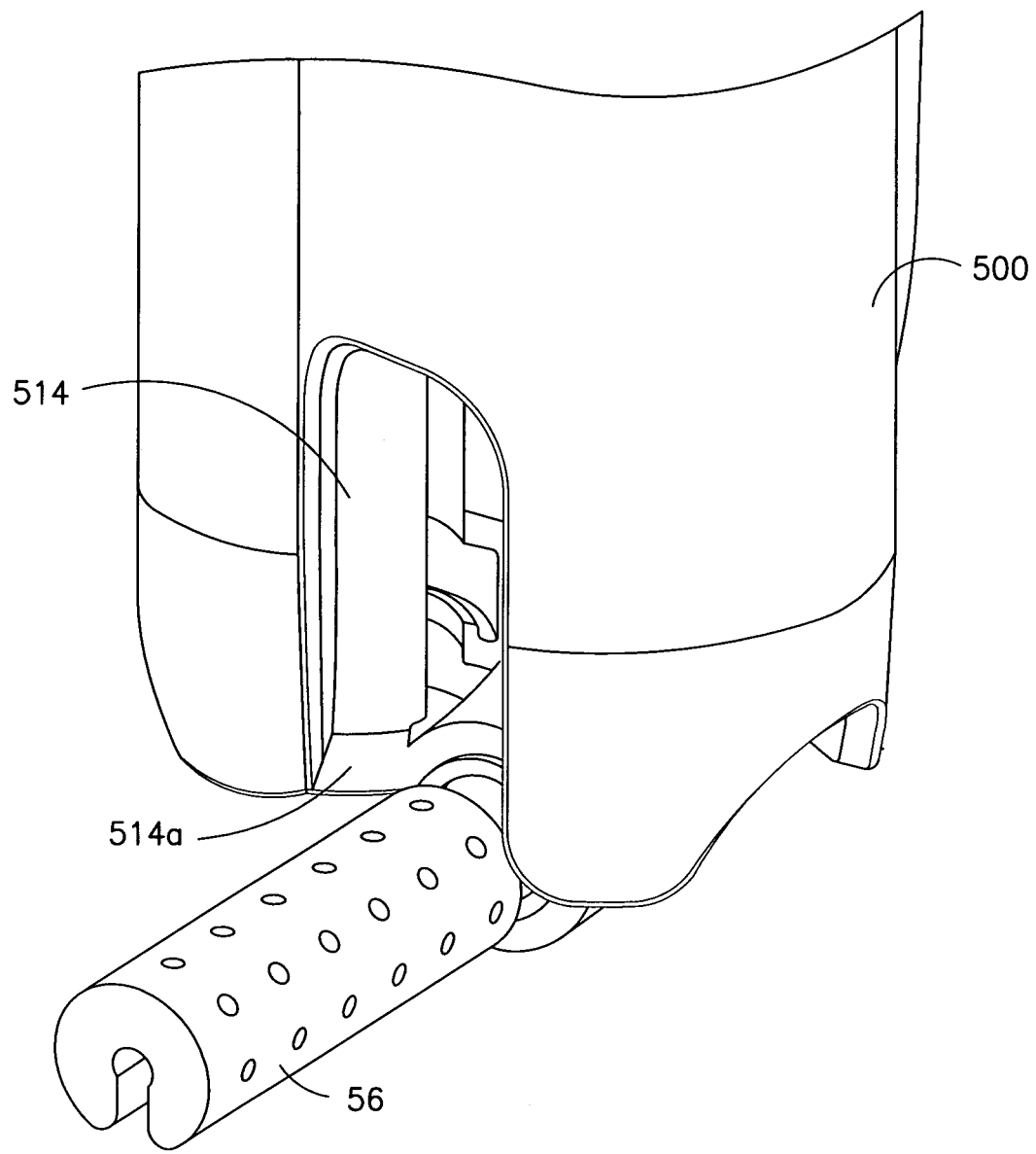
FIG. 35 is an enlarged perspective view of the tubular implant of FIG. 34 after being left behind on the spinal elements.

Rather than pushing implant 56 out into the space in which bone graft is desired, delivery device 72 allows the surgeon to essentially "park" implant 56 across the elements in the location desired and then gradually withdraw outer sheath 74 relative to handle 78, leaving implant 56 behind. This process is shown in FIGS. 33-34 prior to withdrawal of outer sheath 74. In FIG. 34 outer sheath 74 has been withdrawn completely leaving implant 56 behind. As depicted in FIG. 34, delivery device 74 is constructed to include an inner access tube 84 which remains stationary relative to handle 78 while outer sheath 74 is withdrawn upwardly over tube 84. Implant 56 engages inner tube 84 and is thereby maintained in place during the outer sheath withdrawal process. FIG. 35 shows implant 56 in enlarged view after being pushed down through opening 514a of window 514 of tubular retractor 500 toward spinal elements. The dimensions of implant 56 are selected by the surgeon according the anatomy of the patient to span the spinal segment. In the lower lumbar spine, for example, the length of implant 56 may be as large as 60 mm, while in the upper thoracic spine the lengths may be in the range of about 20 to 25 mm. Diameter will range from 5 mm to 15 mm with a diameter of about 9 mm being preferred.

Figure 36:
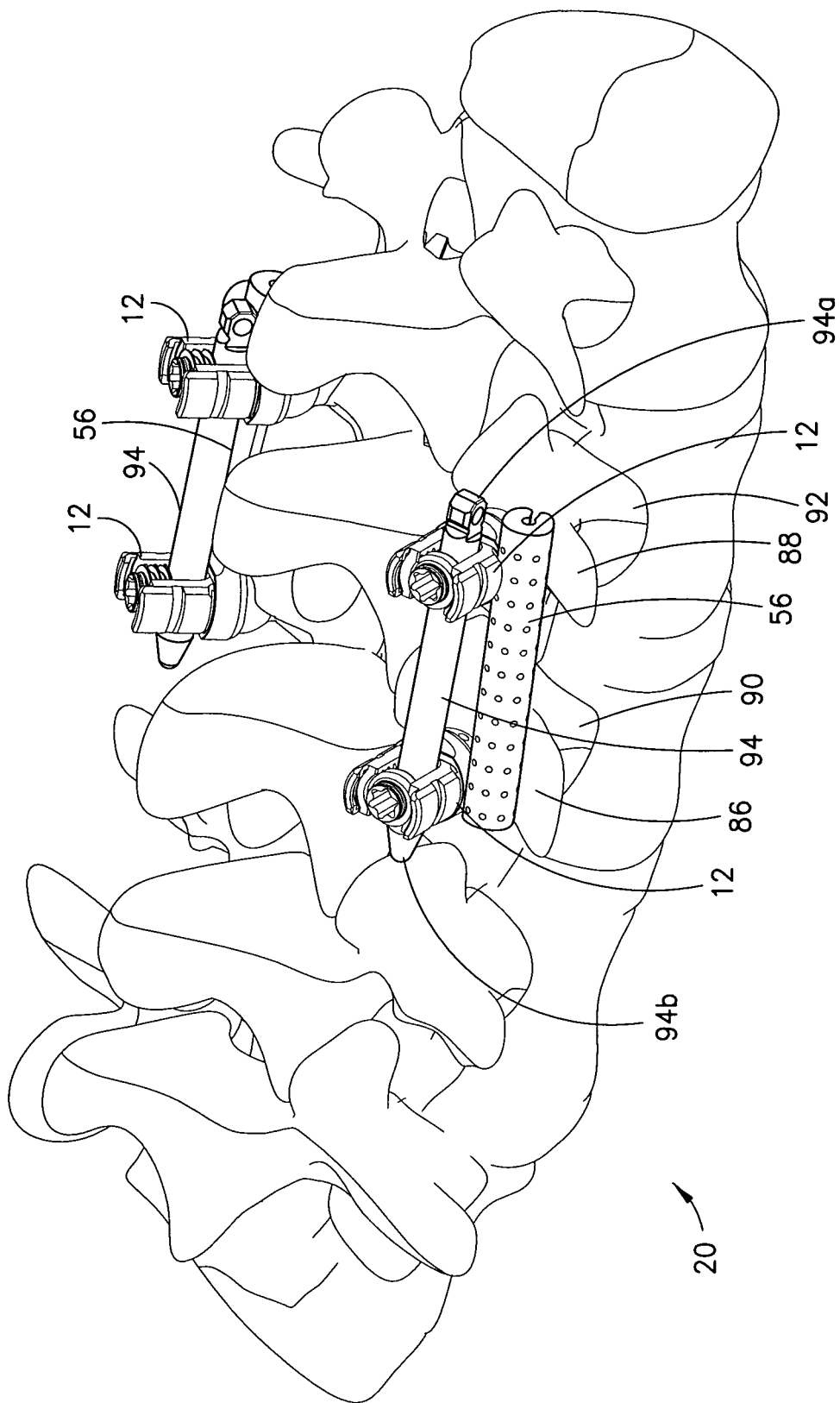
FIG. 36 is a top perspective view of a pair of bilateral tubular implants and connecting rods having been percutaneously placed on the spine.

It should now be appreciated that a bone graft material such as bone graft implant 56 can be placed percutaneously across a spinal segment by spinal fusion system 1 as described herein in order to fuse two a more vertebral bodies of spine 20. The placement of graft implant 56 on the transverse processes 86 and 88 of respective vertebral bodies 90 and 92 is illustrated in FIG. 36. Using a pair of pedicle screw extension assemblies 10 and a tubular retractor 500 together with various tissue preparation instruments as described herein, graft implant 56 has been placed in the position shown in FIG. 36 through a small incision, such as incision $I_1$ or $I_2$, and then moved subcutaneously through a tissue passageway formed by a blunt dilator 422 adjacent to pedicle screws 12 previously inserted into the pedicles of vertebral bodies 90 and 92. In the case depicted in FIG. 36, implant 56 is disposed laterally of pedicle screws 12 on transverse processes 86 and 88. With the instruments of spinal fusion system 1 and related instruments and methods of use as described herein, implant 56 may have been placed alternatively more midline, such as on the elements of the facet or pars intra-articularis.

With graft implant 56 suitably placed in the desired position on the spinal elements and with the tubular retractor 500 removed from screw extension 14 of pedicle screw extension assembly 10, suitable fixation may also be implanted percutaneously adjacent to graft implant 56. Using slots 26 of screw extensions 14 respectively projecting outwardly from the patient through incisions $I_1$ and $I_2$ a connecting rod 94 may be installed in a manner as described in the '640 Patent. In such procedure, connecting rod 94 is pivotally attached at its proximal end 94a to a suitable rod introducer (not shown). The distal end 94b of connecting rod 94 is inserted through incision $I_1$ or $I_2$ and through slots 26 of a first pedicle extension 14 and is then moved subcutaneously through tissue and into and through slots 26 of a second pedicle extension 14. Connecting rod 94 is suitably disconnected from the rod introducer, screw extensions 14 are removed from pedicle screws 12 and incisions $I_1$ and $I_2$ are suitably sutured to complete this aspect of the surgical procedure. Another graft implant 56 and connecting rod 94 may be installed on the contralateral side of spine 20 to vertebral bodies 90 and 92 in the same manner as the installation of first graft implant 56 and connecting rod 94. It can thus be appreciated that the entire surgical procedure including the implantation of graft material to promote fusion between vertebral bodies 90 and 92 and associated fixation may be performed percutaneously.

While the invention has been illustrated and described in detail in the drawings and foregoing description, the same should be considered as illustrative and not restrictive in character. For example, while the placement of the graft implant as well as associated fixation can be placed on the spinal elements in a percutaneous method whereby the graft implants and connecting rods are placed through individual separate incisions, it can be appreciated that the spinal fusion system and instruments described herein may be also be used minimally invasively. As such, in situations for instance where the vertebral bodies of the affected spinal segment are relatively close the formation of separate incisions associated with each vertebral body may be difficult, if not impossible, to achieve. In this instance, a single incision, which may be longer than the small incision described hereinabove, may be formed for access to both vertebral bodies with two pedicle screw extension assemblies and tubular retractors introduced through the same incision in a minimally invasive procedure. In some situations, a surgeon may find it advantageous to use the system described herein, or certain of the instruments or tubular retractors for an open spinal procedure.

Figure 37:
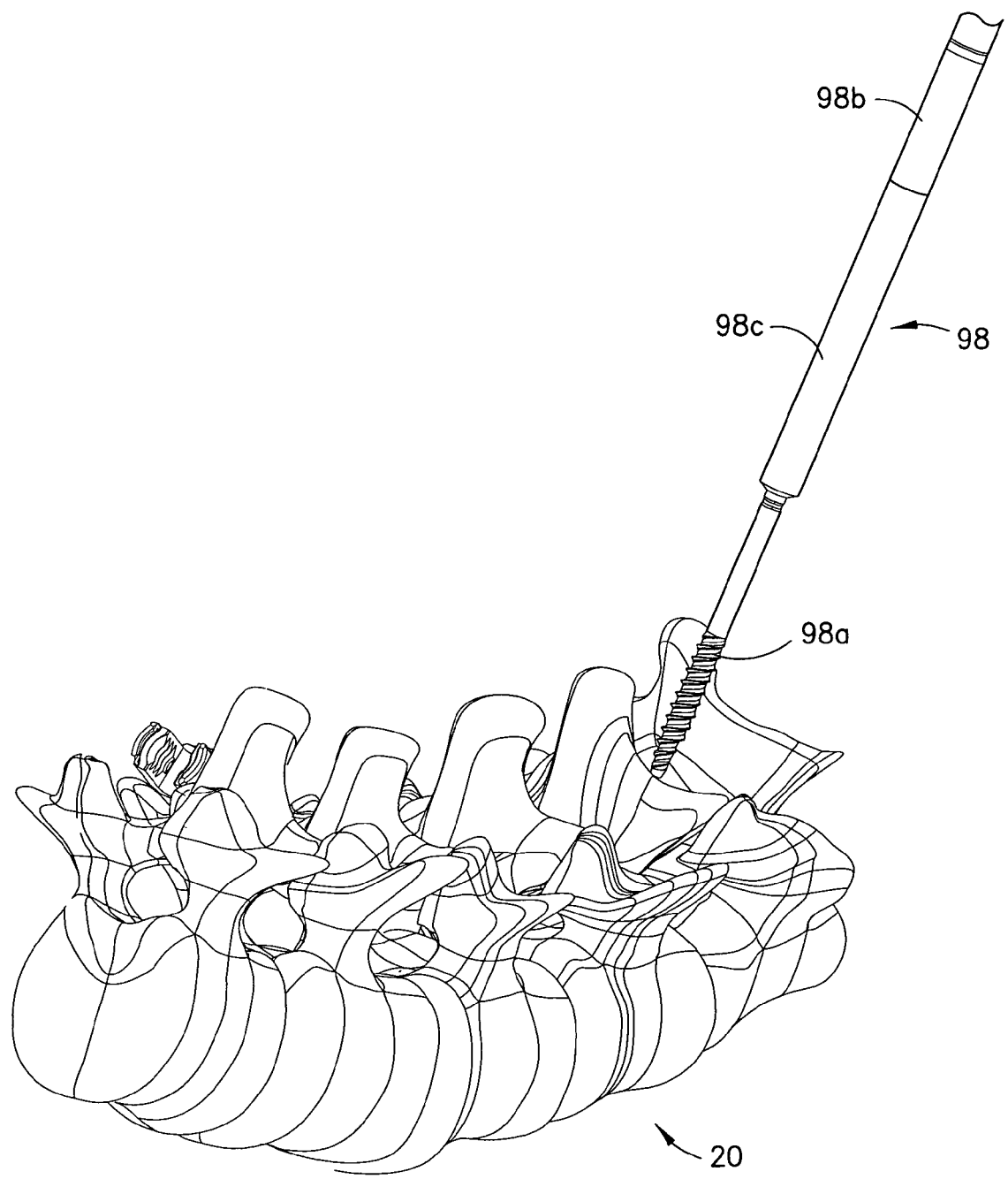
FIG. 37 is a top perspective view of a threaded screw tap as an alternative access point to the spinal elements prior to placement of a multi-axial screw.
Figure 38:
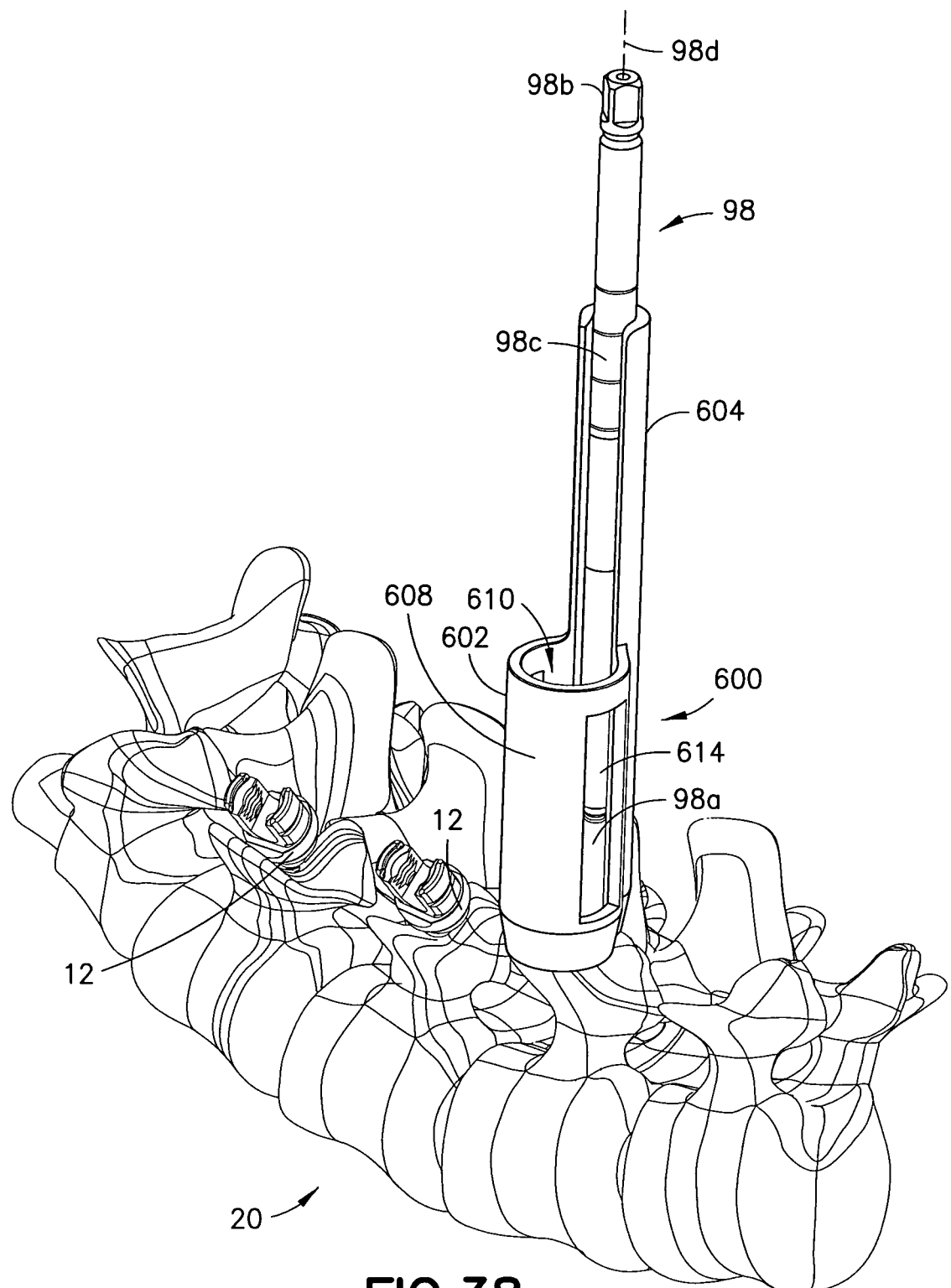
FIG. 38 is a top perspective view similar to FIG. 2, showing a modified retractor rotatably attached to the tap of FIG. 37.
Figure 39:
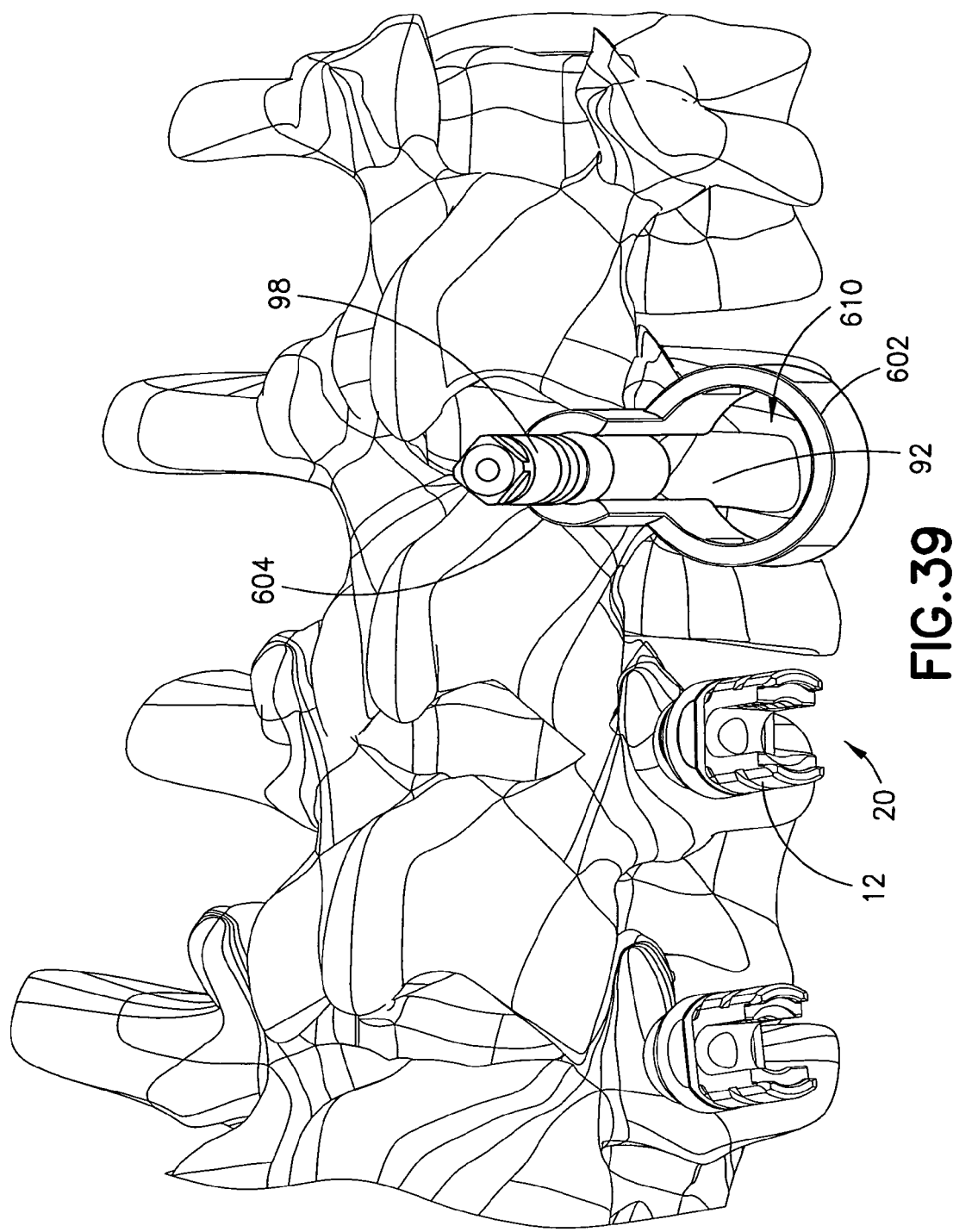
FIG. 39 shows a top view of the tap and tubular retractor of FIG. 38 depicting the access port as would be visualized by a surgeon.

A further variation within the contemplated scope of the invention is shown in FIGS. 37-39. A primary focus of the spinal fusion system 1 described heretofore rests on utilization of multi-axial pedicle screw 12 as a fixed access point which allows for simultaneous rotational variability of screw extension 14 and an attached tubular retractor, such as tubular retractor 100, 200, 300, 400 or 500. Once the multi-axial screw 12 is placed in the pedicle, it is possible that the screw head could obscure the surgeon's access to some areas of the spinal elements, such as the transverse processes in which there may be interest in removing bone and providing for a bony surface for spinal fusion. FIG. 37 shows the use of a rigid tap 98 as an alternative access point, where tap 98 would be placed prior to placement of multi-axial screw 12. Tap 98 is an elongate fixation member including a distal end 98a and a proximal end 98b. Distal end 98a is threaded fixation element for insertion into a pedicle of a vertebral body. An elongate extension 98c extends proximally from distal end 98a defining a longitudinal axis 98d along the length of extension 98c. Threaded end 98a and elongate extension 98c are fixed together for joint rotation.

It is noted that rigid tap 98 would not provide for the multi axial degrees of freedom and rotation provided by multi-axial screw 12. As such, a modified retractor 600 as depicted in FIG. 38 is contemplated. Tubular retractor 600 includes a modification of tubular retractor 200. Reference numerals illustrating elements of tubular retractor 600 that are common with tubular retractor 200 are increased by 400 for ease of description. Unlike tubular retractor 200, however, attachment portion 604 of tubular retractor 600 does not have a flat interior surface and thereby is not keyed to extension 98c of tap 98 when tubular retractor 600 is releasably attached to extension 98c.

Upon attachment of attachment portion 604 to extension 98c the longitudinal attachment axis of attachment portion is substantially coaxial with longitudinal axis 98d of extension 98c and pathway 610 is laterally offset elongate extension 98c. While threaded end 98a and extension 98c are rotationally fixed, attachment portion 604 and thereby tubular retractor 600 with pathway 610 may freely rotate about extension 98c. Rotation of pathway 610 would allow for a broader area of bony decortication that could potentially be impeded by the presence of the head of pedicle screw 12 introduced later in the procedure. In particular, rotating tubular retractor 600 laterally allows for direct visualization of the inter-transverse process and full decortication of those elements prior to bridging bone graft placement. However in this case, the primary exposure and access needed via tap 98 is to provide for decortication of the transverse process 32 of spine 20. FIG. 39 shows an overview of tap 98 and tubular retractor 600 placed over the tap extension 98c. Access port pathway 610 provides for orientation and access to transverse process 32.

Figure 40:
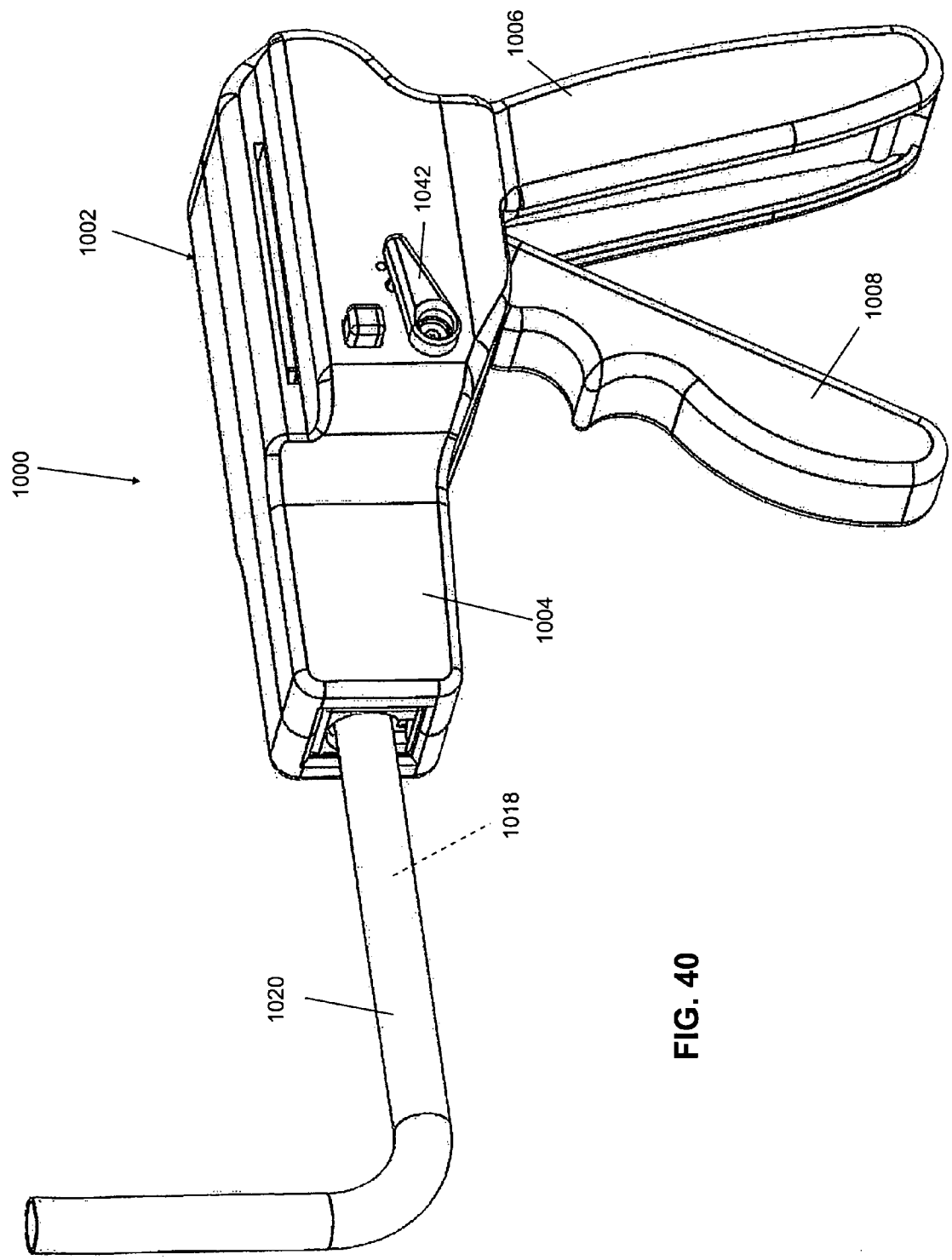
FIGS. 40-42 show an instrument useable for the delivery of a graft, implant and/or graft material in accordance with the subject invention.
Figure 41:
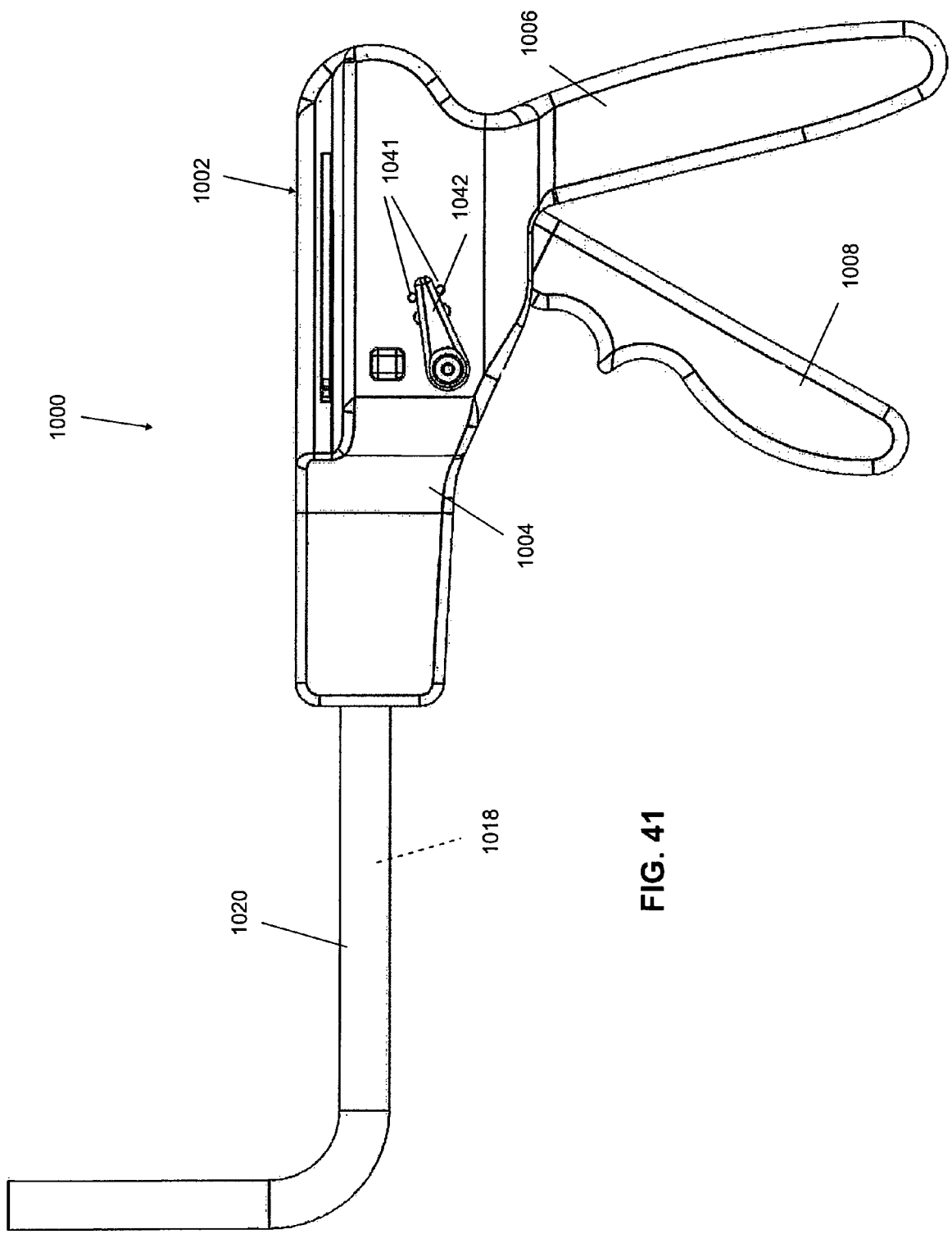
Figure 42:
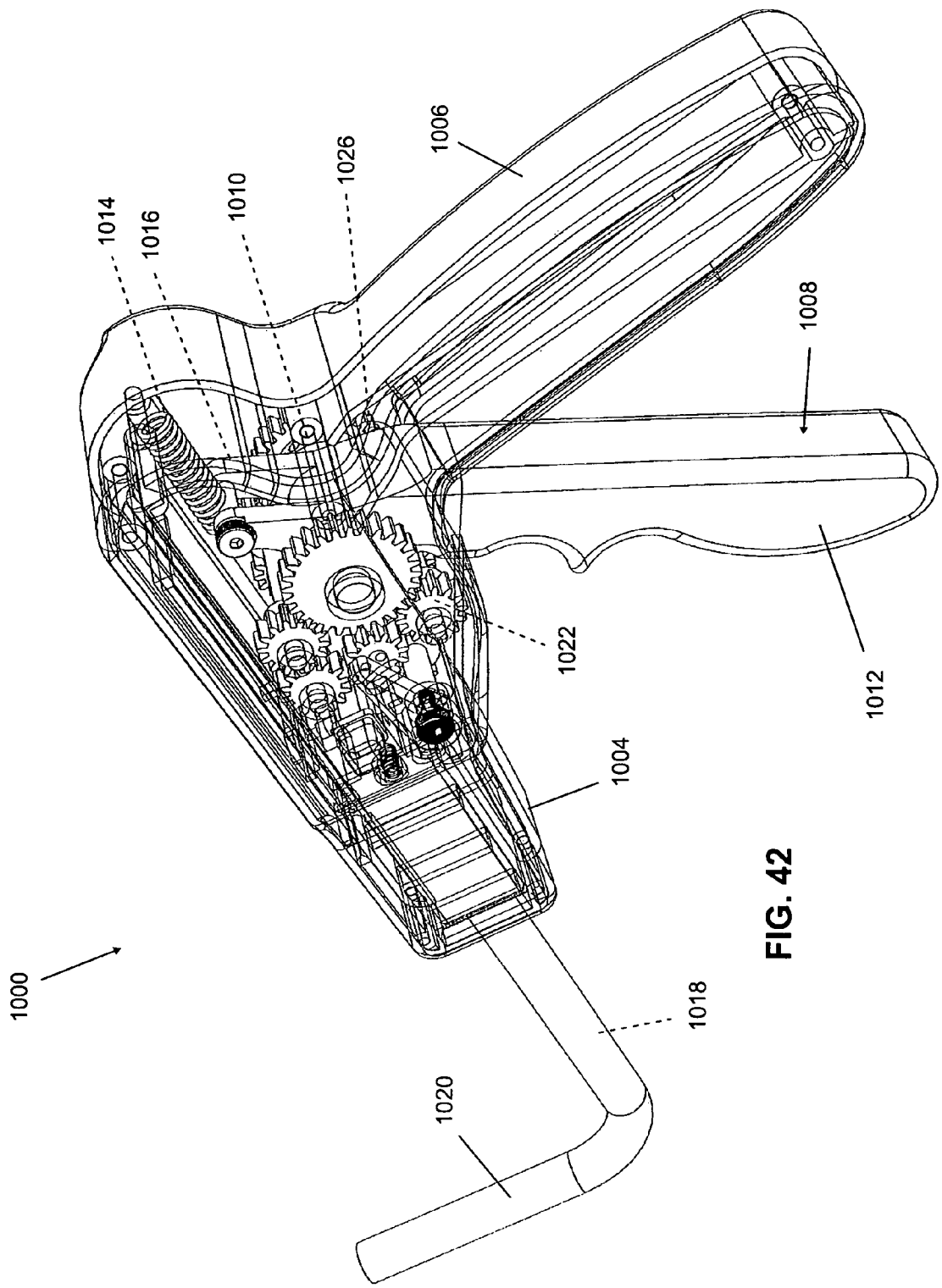
Figure 43:
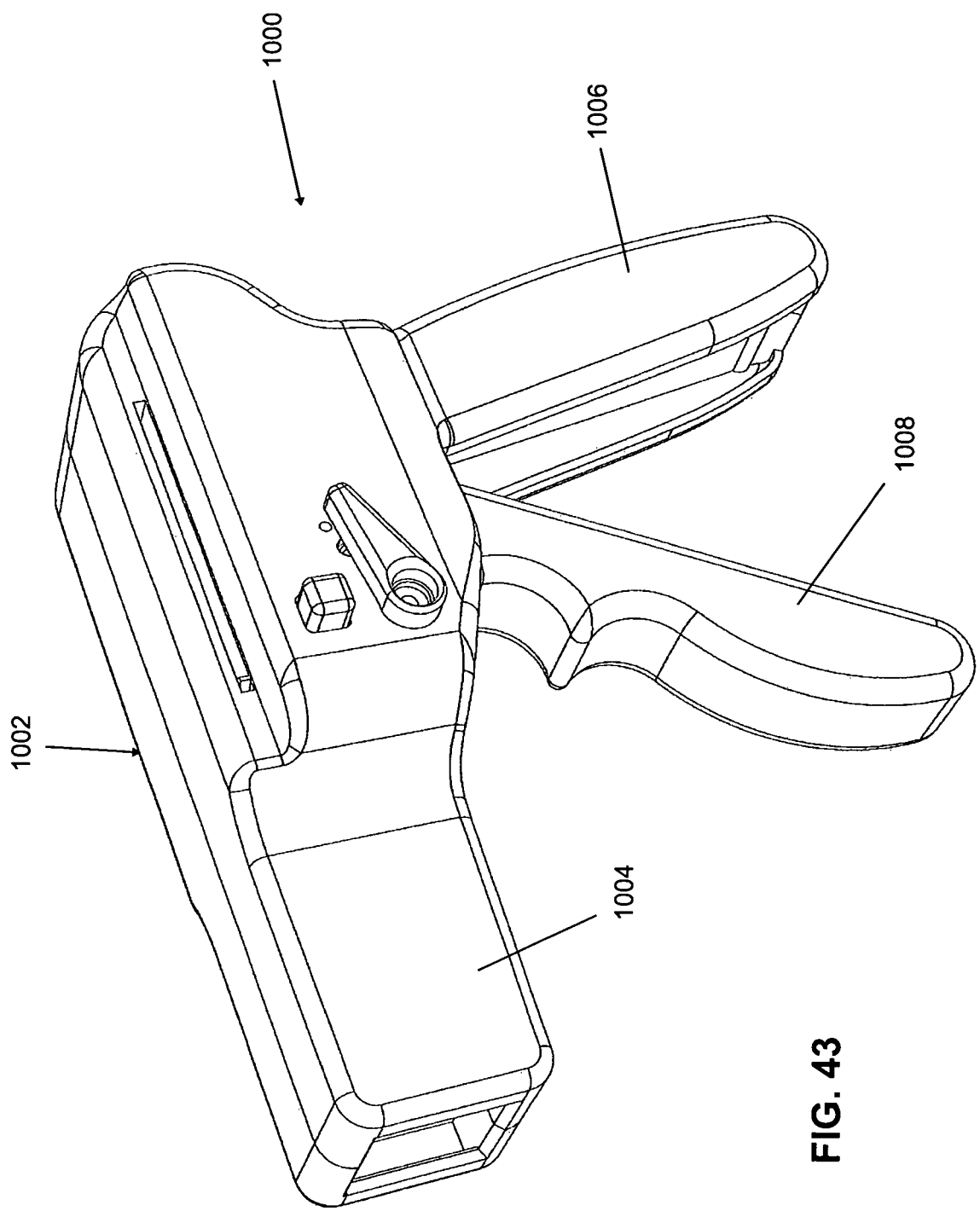
FIG. 43 is a top perspective view of a housing useable with the instrument.
Figure 44:
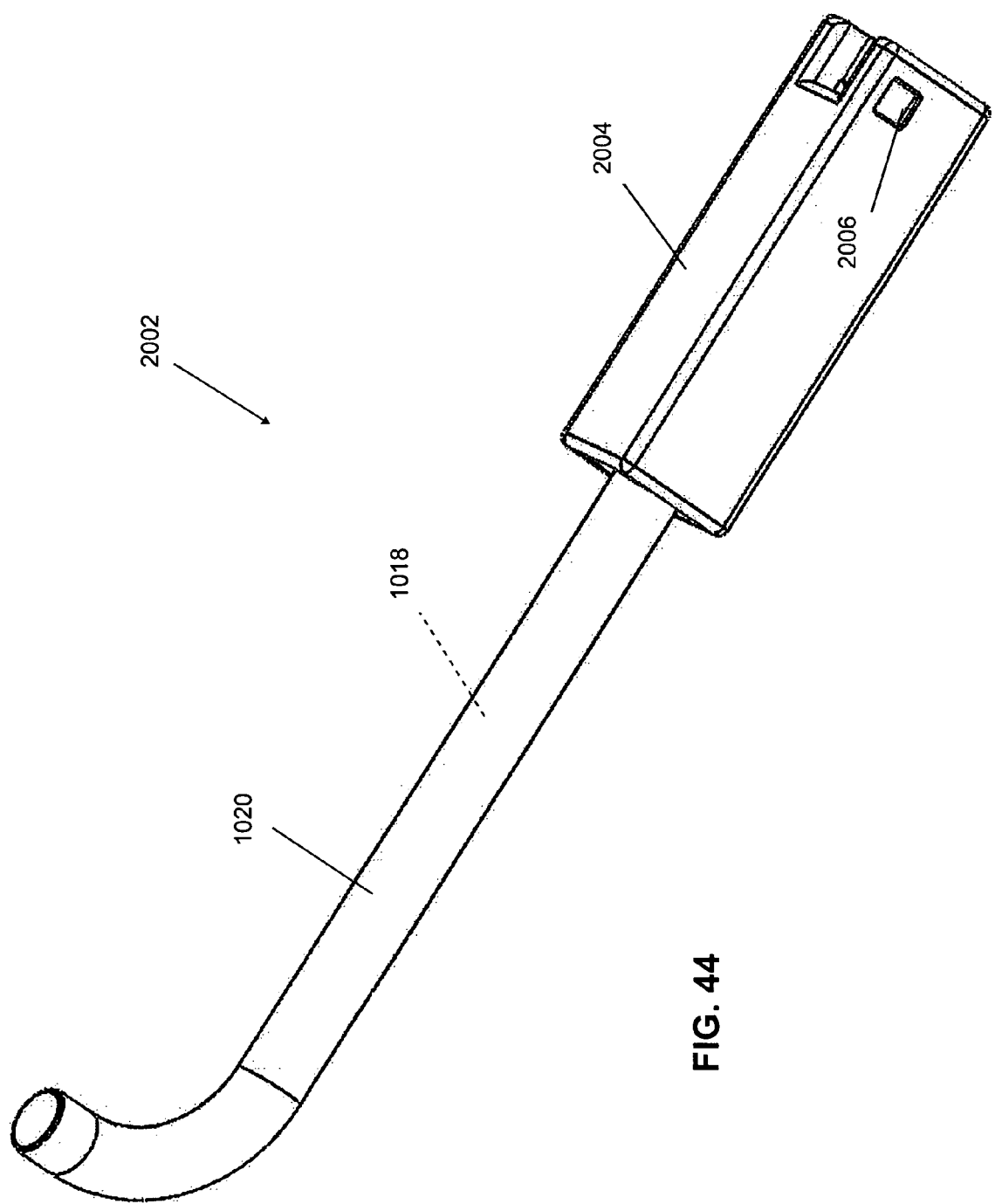
FIG. 44 is a top perspective view of a cartridge useable with the system for delivering a graft, implant and/or graft material.
Figure 45:
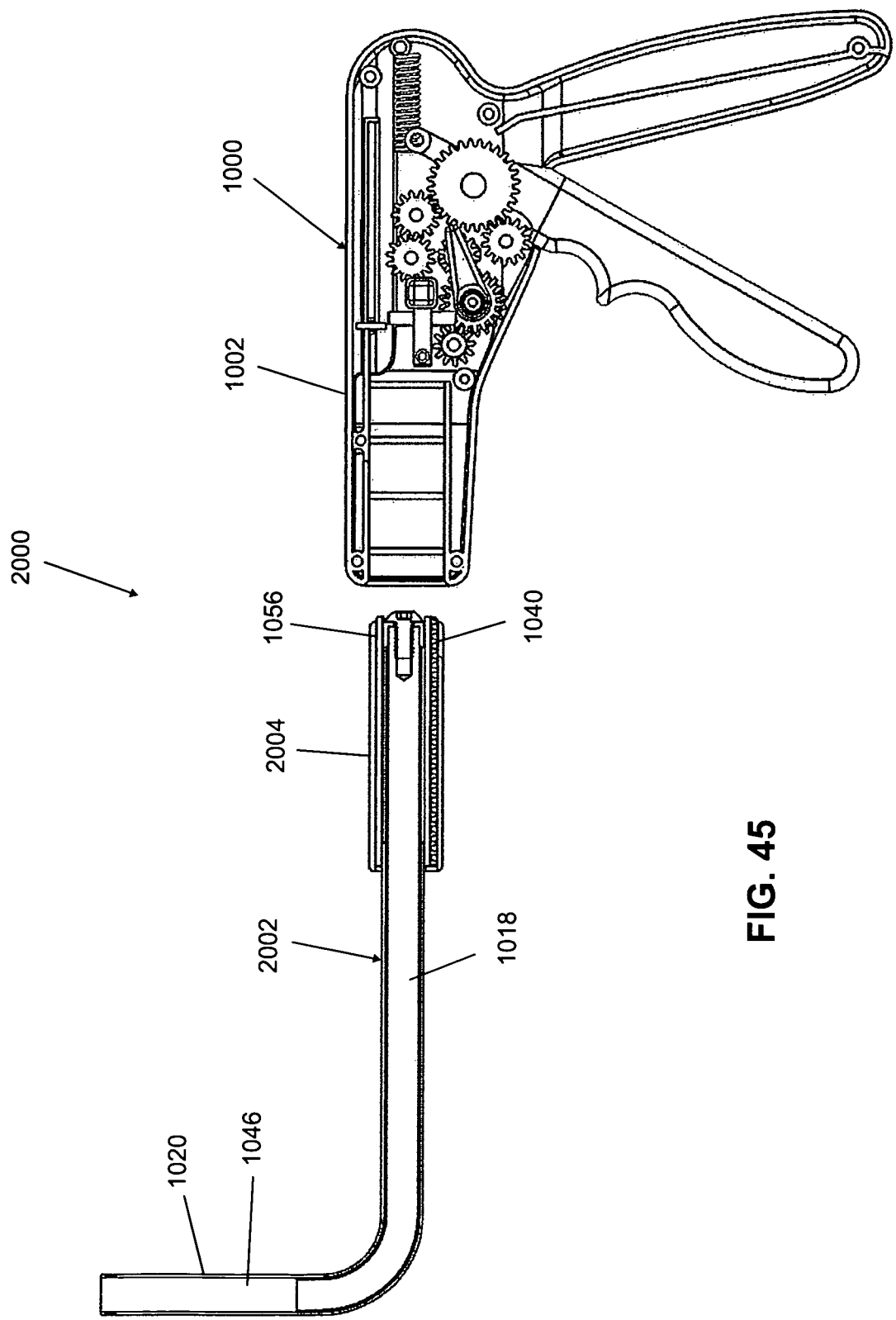
FIG. 45 is an exploded cross-sectional view of a system useable for delivering a graft, implant and/or graft material.
Figure 46:
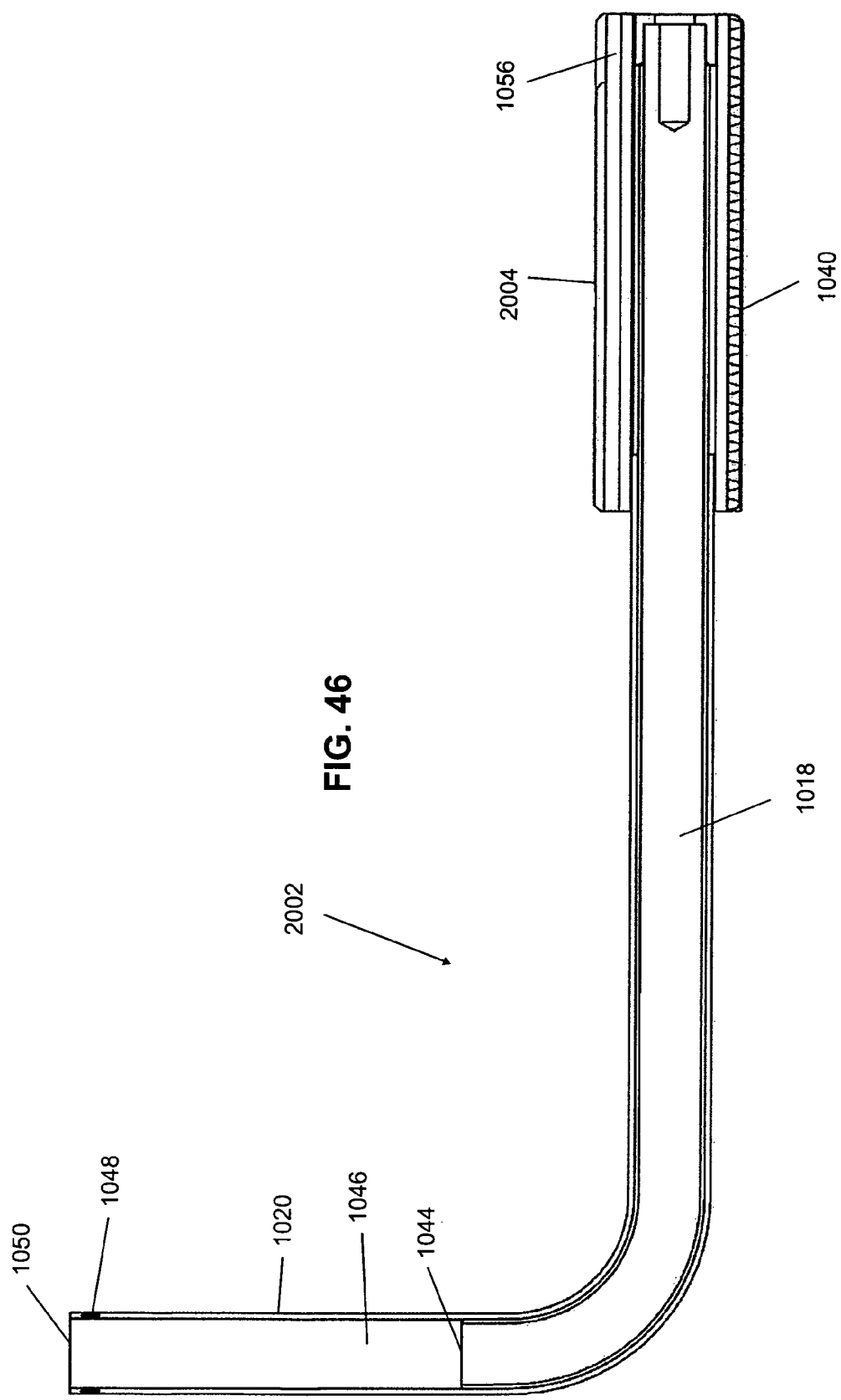
FIG. 46 is cross-sectional view of the cartridge of FIG. 44.

FIGS. 40-74 show an instrument and system which may be used to place the perforated graft 42 or the tubular implant 56 at a target site, such as shown at FIGS. 23 and 28-29. As will be appreciated by those skilled in the art, the instrument and system may be useable with other applications, such as, for example, placement of graft material in the intradiscal space between two opposing vertebrae. In particular, an instrument 1000 is shown which includes a housing 1002. Preferably, the housing 1002 is generally pistol-shaped having a barrel portion 1004 from which extends a hand grip 1006. An actuatable trigger 1008 is associated with the housing 1002. The trigger 1008 may be fixed to the housing 1002, preferably movably. As shown in FIG. 42, the trigger 1008 may be pivotally mounted about mount 1010. In this manner, lower portion 1012 of the trigger 1008 may be engaged by a user to cause actuation of the trigger 1008 with a squeezing action about the grip 1006 and the lower portion 1012. Spring 1014 may be provided to apply a biasing force against the trigger 1008, such as to upper portion 1016, so as to urge the trigger 1008 to an open, at-rest state as shown at FIG. 40.

The instrument 1000 further includes a curved access tube 1018, which is similarly formed to the delivery device outer sheath 66, as shown in FIG. 30, or the outer sheath 74, as shown in FIG. 31. The access tube 1018 is mounted to the housing 1002, permanently or detachably, preferably, to the barrel portion 1004. A sheath 1020 is disposed about, and moveable relative to, the access tube 1018.

A transmission 1022 is provided within the housing 1002 configured to cause incremental displacement of the sheath 1020 relative to the access tube 1018.

Figure 56:
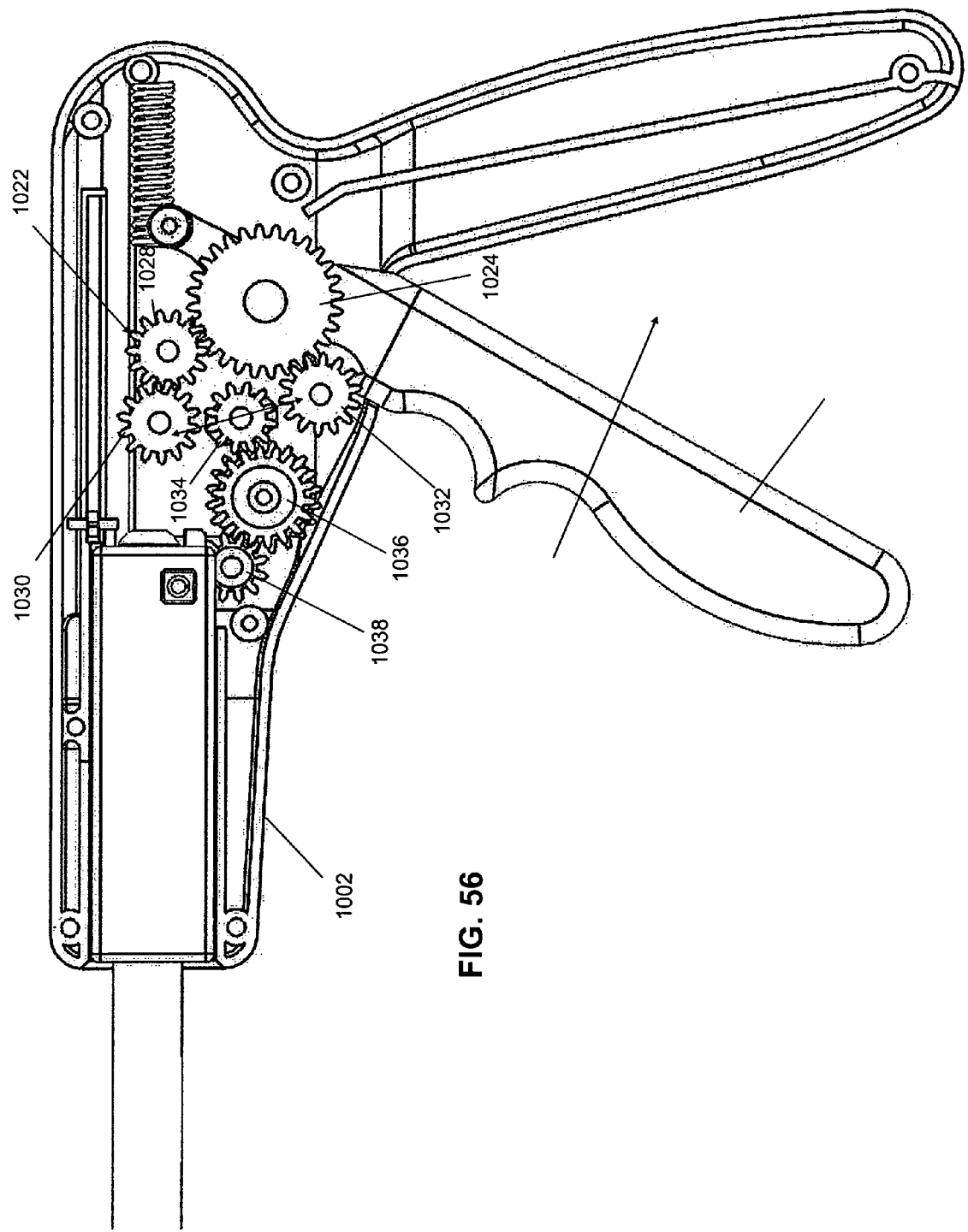
FIGS. 56-58 show a transmission useable with the subject invention.
Figure 57:
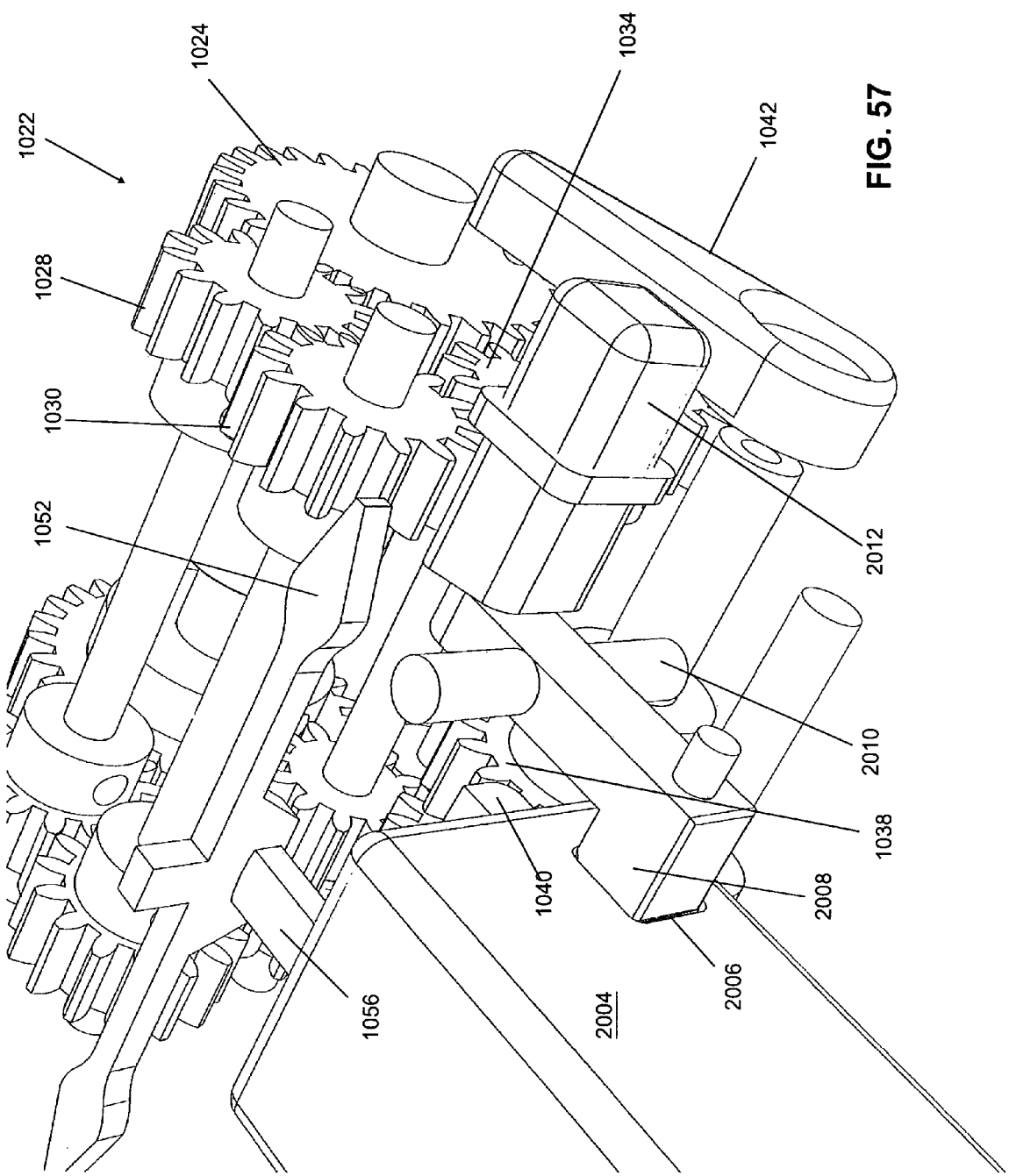
Figure 58:
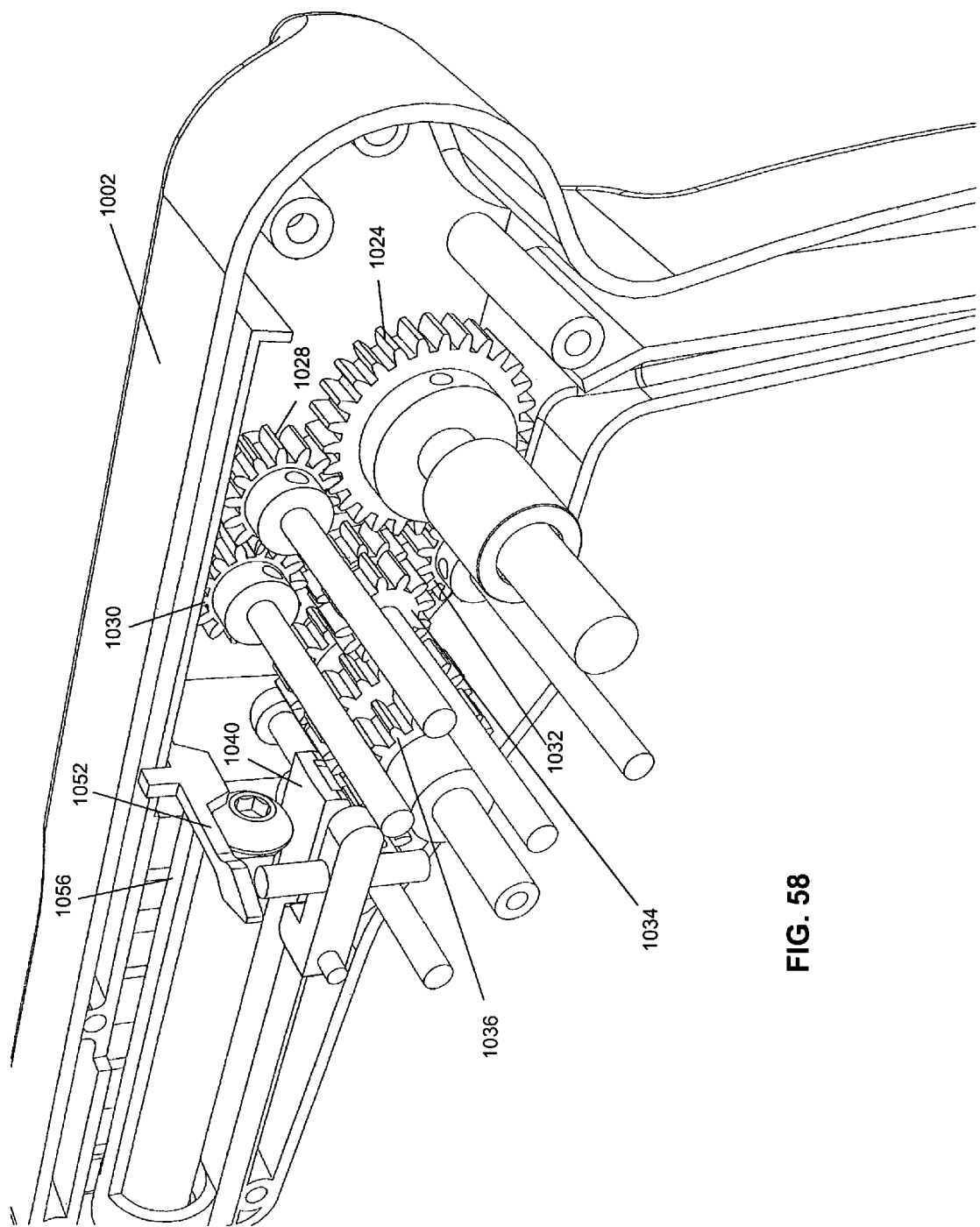

By way of non-limiting example, reference is made to FIGS. 56-58 for one configuration of the transmission 1022. The transmission 1022 may include a gear train of two or more intermeshing gears. At least one main gear 1024 is located to be rotationally displaced over a fixed amount upon an actuation of the trigger 1008. An indexer 1026 (FIG. 42) may be provided on the trigger 1008 which is configured to displace the main gear 1024 the fixed rotational amount. The fixed rotational amount may be defined by the extent of interengagement between the main gear 1024 and the indexer 1026. With the trigger 1008 being pivotally mounted, the indexer 1026 may be caused to sweep across an arc of movement with the actuation of the trigger 1008 (i.e., being squeezed with the grip 1006). With the trigger 1008 in the open, at-rest state, the indexer 1026 is located to be meshed between teeth of the main gear 1024. With actuation, the indexer 1026 is displaced along the arc of movement, causing the main gear 1024 to move, and thus rotate. Upon sufficient movement, the indexer 1026 separates from the main gear 1024, thus, halting movement. In returning to the open, at-rest state, the indexer 1026 is returned to its initial state, again meshed between teeth of the main gear 1024. In this manner, each repeated actuation of the trigger 1008 results in a fixed amount of rotation of the main gear 1024.

The transmission 1022 may further include a follower gear 1028 intermeshed with the main gear 1024 and, separately, intermeshed with a secondary follower gear 1030. A reversing gear 1032 may be also provided intermeshed with the main gear 1024. Movement of the main gear 1024 results in movement of the follower gear 1028, the secondary follower gear 1030, and the reversing gear 1032, if provided.

Figure 56A:
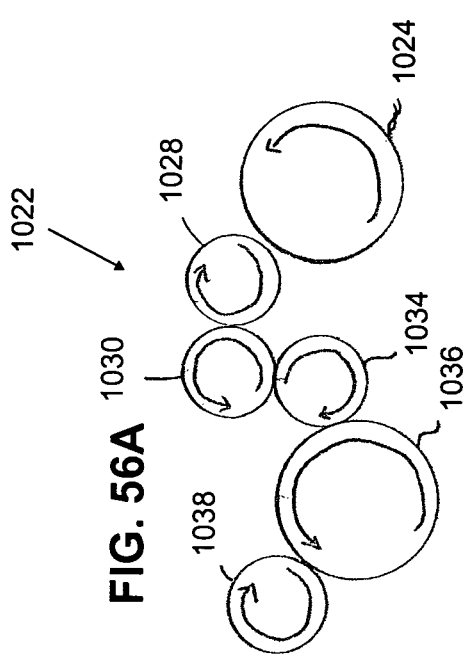
Figure 56B:
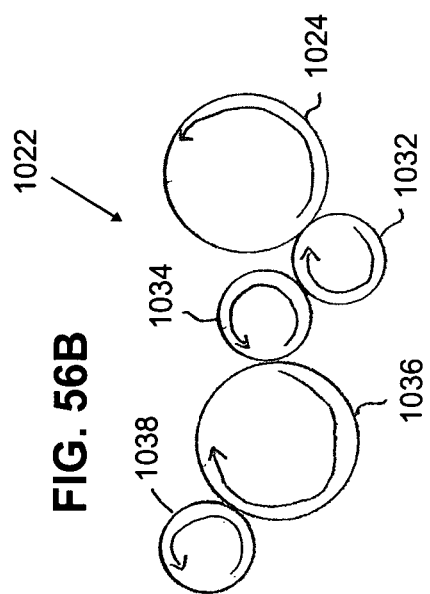

Switching gear 1034 may be provided which is moveable, as shown at FIG. 56, to selectively intermesh with the secondary follower gear 1030 and the reversing gear 1032. The switching gear 1034 is intermeshed with stationary gear 1036. The stationary gear 1036 is sized to allow for intermeshing engagement with the switching gear 1034 in all positions. The stationary gear 1036 is, in turn, intermeshed with pinion 1038. As shown schematically in FIG. 56A, with the switching gear 1034 in intermeshing engagement with the secondary follower gear 1030, the pinion 1038 is caused to rotate in a clockwise fashion as a result of an actuation of the trigger 1008. Conversely, as shown in FIG. 56B, with the switching gear 1034 in intermeshing engagement with the reversing gear 1032, the pinion 1038 is caused to rotate in a counterclockwise fashion. With the transmission 1022 as presented, the pinion 1038 may be selectively caused to rotate in either direction based on discrete actuations of the trigger 1008, with no change to the manner of actuation. Moreover, each of the actuations of the trigger 1008 causes a limited amount of rotation of the pinion 1038 in either direction.

Figure 47:
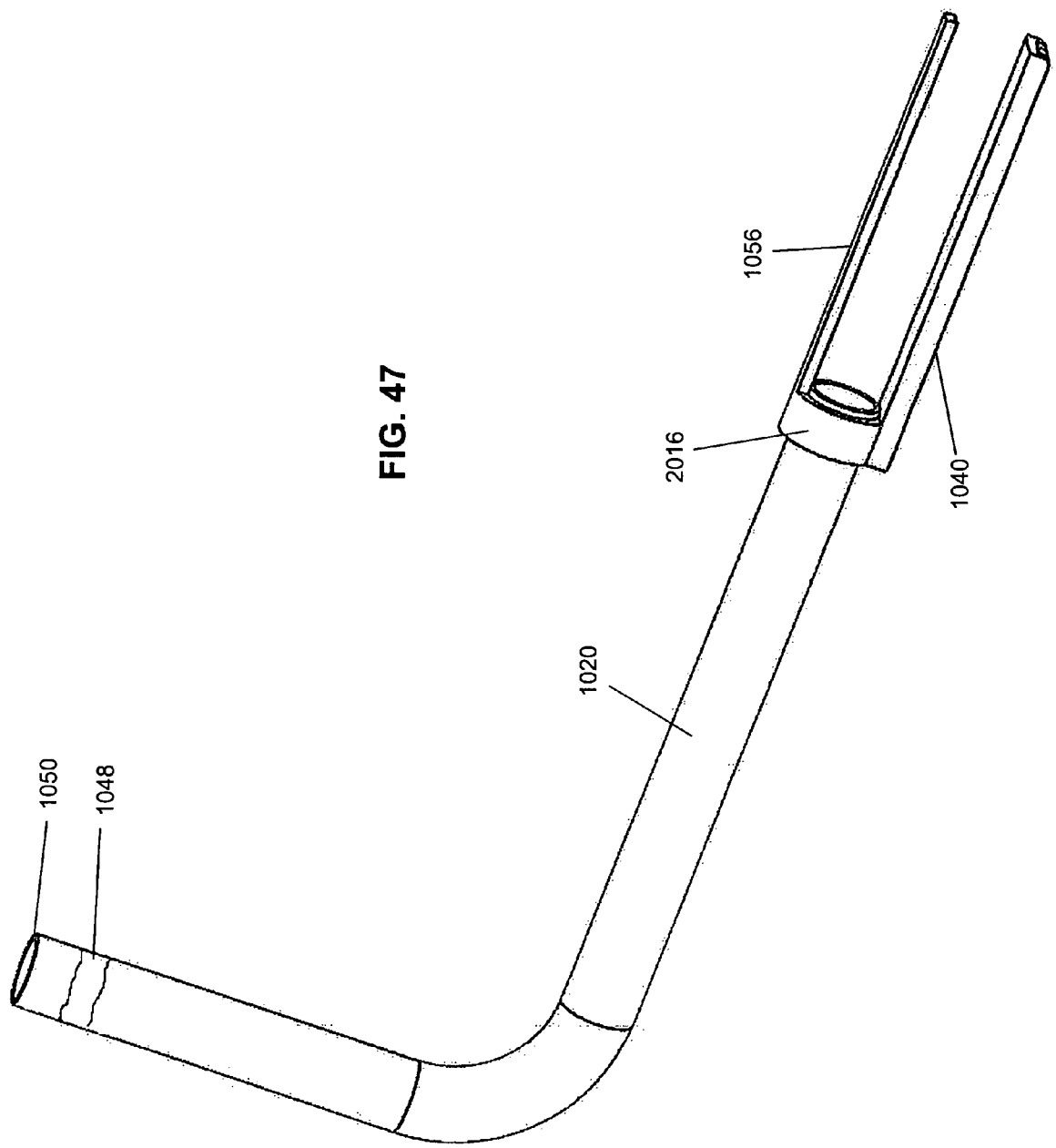
FIG. 47 shows the sheath having fixed thereto the rack and the protrusion.
Figure 48:
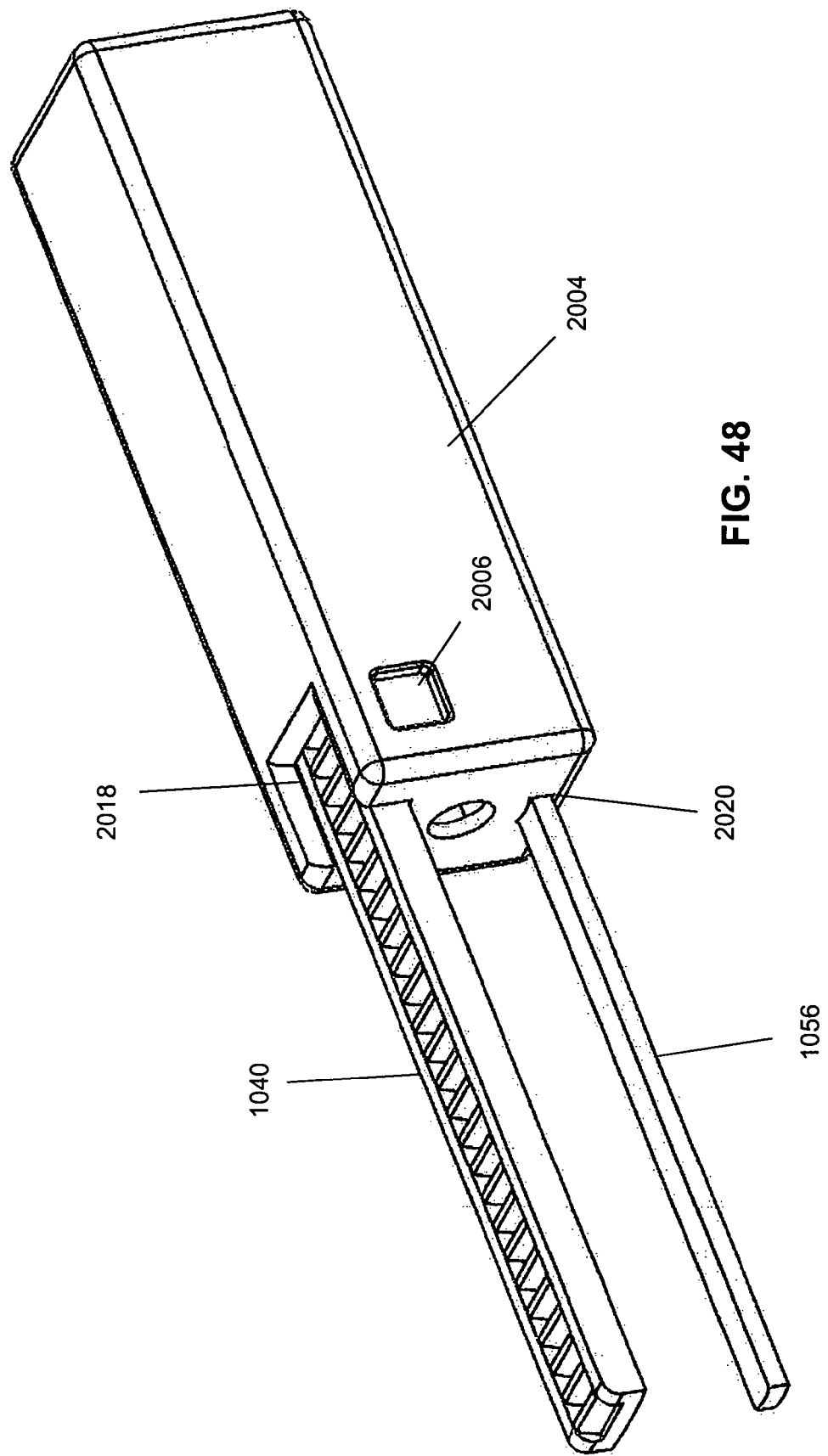
FIGS. 48-50 show the body of the cartridge with the rack and the protrusion being in different locations.

As shown at FIG. 47, a rack 1040 is fixed to the sheath 1020. The rack 1040 is positioned to be in intermeshing engagement with the pinion 1038 (FIG. 57). Rotation of the pinion 1038 causes linear translation of the rack 1040. The direction of linear translation is determined by the direction of rotation of the pinion 1038. Moreover, due to the limited extent of rotation of the pinion 1038 upon an actuation of the trigger 1008, the rack 1040 is correspondingly displaced in limited increments. Through displacement of the rack 1040, the sheath 1020 is caused to move relative to the access tube 1018.

Figure 65:
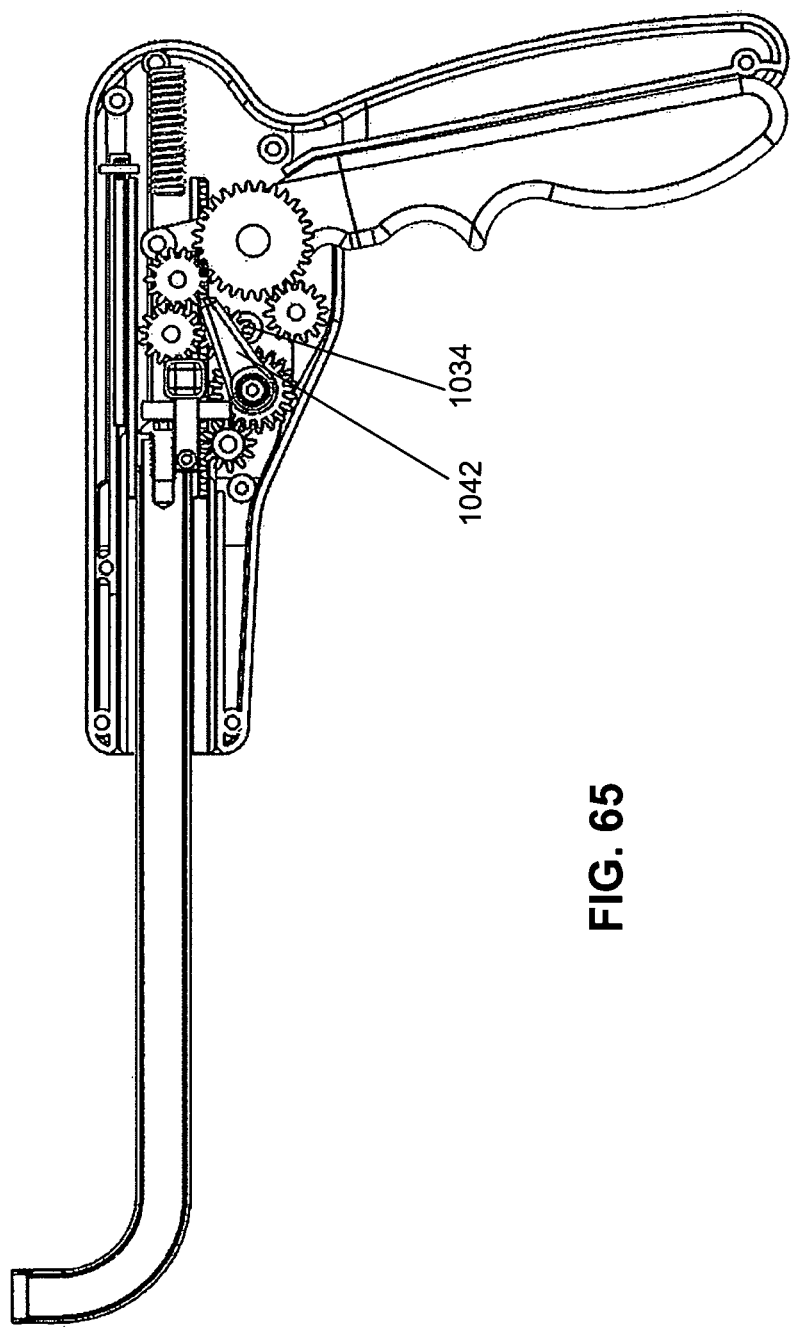
FIGS. 65-66 show the shifter in altered states.
Figure 66:
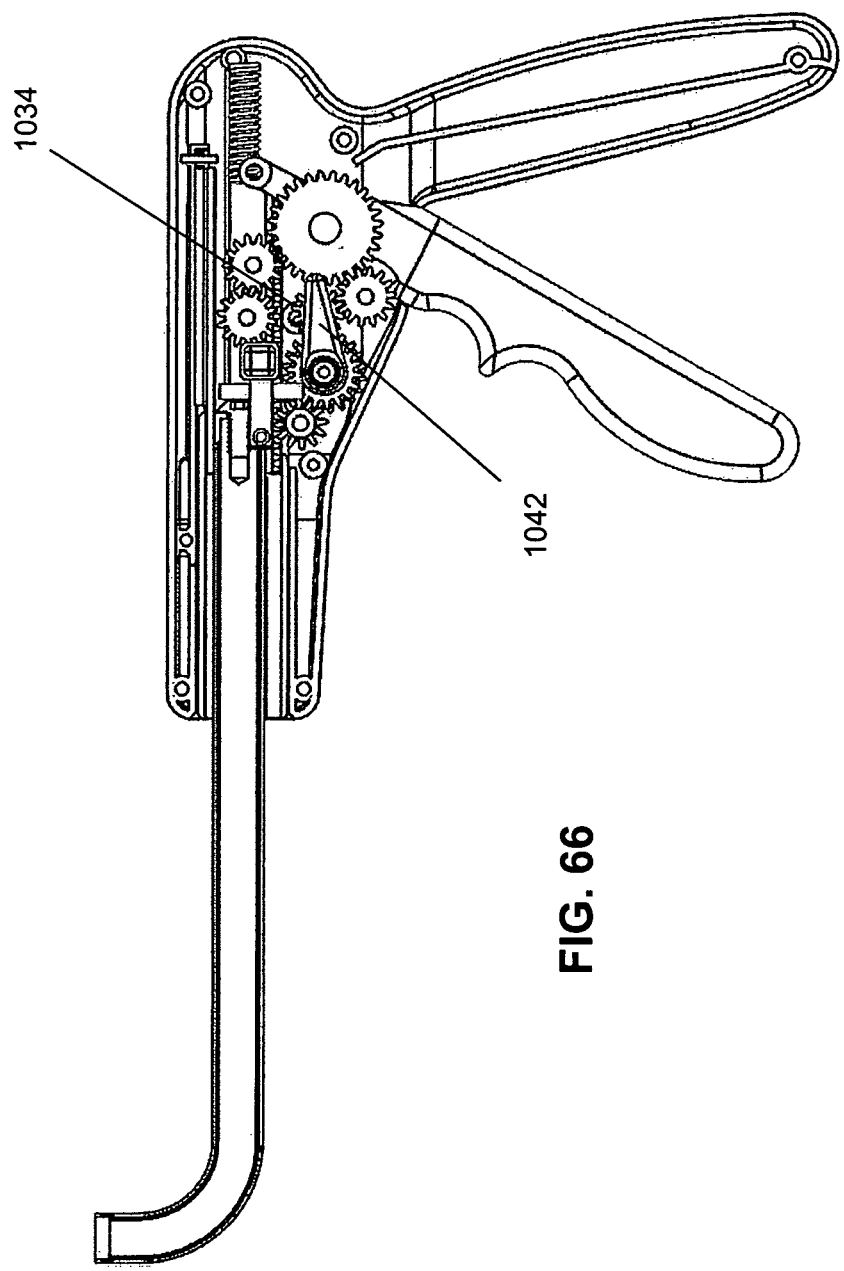

As will be appreciated by those skilled in the art, any manner by which the switching gear 1034 may be caused to be displaced may be used with the subject invention. For example, as shown at FIG. 40, shifter 1042 may be provided on the housing 1002 which may be fixed to the switching gear 1034 so that rotational displacement of the shifter 1042 results in corresponding adjustment of the switching gear 1034. FIGS. 65 and 66 show the shifter 1042 in adjusted positions with the switching gear 1034 being in intermeshing engagement with the secondary follower gear 1030 (FIG. 65) and, alternately, in intermeshing engagement with the reversing gear 1032 (FIG. 66). In addition, the shifter 1042 may be caused to locate the switching gear 1034 out of engagement with the secondary follower gear 1034 and the reversing gear 1032, thus, placing the transmission 1022 into a neutral state. Actuation of the trigger 1008 with the transmission 1022 in the neutral state results in no translation of the rack 1040, in either direction. Detents 1041, or other elements, may be provided on the housing 1002, which may retentively engage the shifter 1042 in a desired state of forward drive, reverse drive, or neutral.

Figure 67:
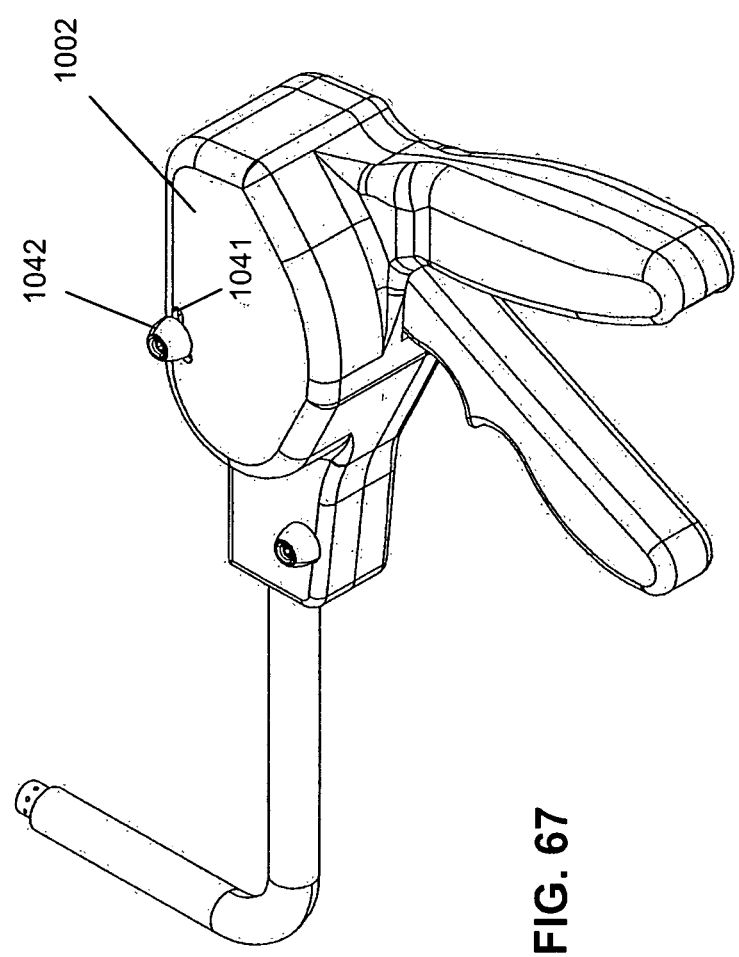
FIGS. 67-68 show an alternate shifter and transmission arrangement.
Figure 68:
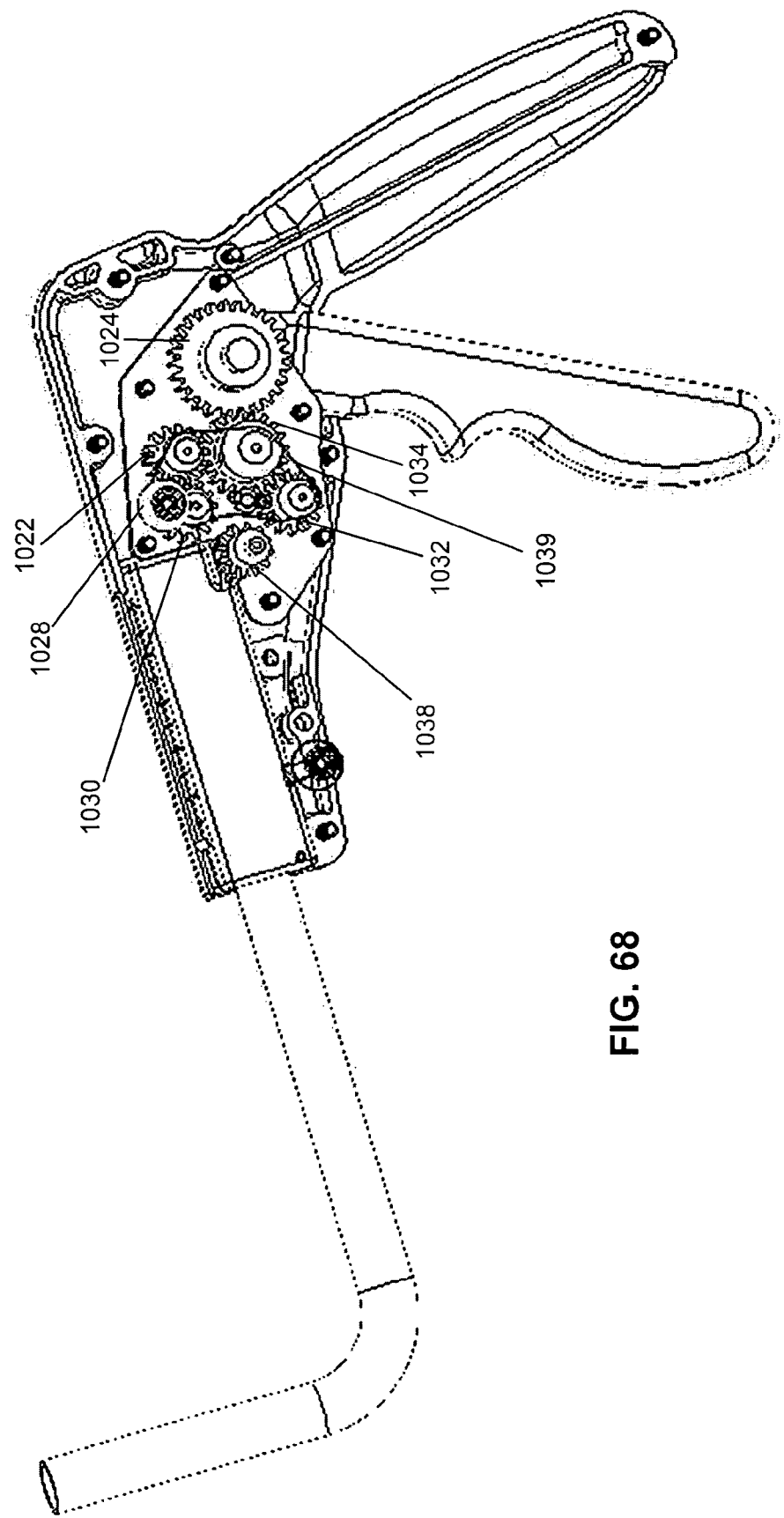

With reference to FIG. 67, the shifter 1042 may be shiftable relative to the housing 1002, e.g., within slot 1041, to cause adjustment of the transmission 1022. As shown in FIG. 68, the gears may be rearranged so that a sub-set of the gears moves together relative to the housing 1002. By way of non-limiting example, the switching gear 1034 may be fixed in a stationary position being in continuous intermeshing engagement with the main gear 1024. In addition, the switching gear 1034 may be in continuous intermeshing engagement with the follower gear 1028 and with the reversing gear 1032. The secondary follower gear 1030, in turn, may be in continuous intermeshing engagement with the follower gear 1028. In a neutral state, both the secondary follower gear 1030 and the reversing gear 1034 are out of engagement with the pinion 1038. With this configuration, the transmission 1022 may be adjusted by adjusting a common mount 1039 to which is fixed the shifter 1042, the switching gear 1034, the follower gear 1022, the secondary follower gear 1028 and the reversing gear 1032. The common mount 1039 may be pivotally mounted, e.g., about the axis of rotation of the switching gear 1034, so that all elements mounted to the common mount 1039 are rotationally shifted with shifting of the shifter 1042. In this manner, the secondary follower gear 1030 and the reversing gear 1032 may be selectively brought into intermeshing engagement with the pinion 1038, resulting in forward or reverse translation of the rack 1040 in similar manner as discussed above.

It is noted that the gear train described herein of the transmission 1022 may be provided on one or both sides of the trigger 1008 and/or in multiples within the housing 1002. If provided on both sides, multiples of the noted gears may be utilized. Two or more of the indexers 1026 may be also provided. The multiples of the same gears, including the pinion 1038, may be mounted to common axles respectively, as shown at FIG. 57. In addition, the gear train may be configured in any known manner, e.g., having the main gear 1024 directly intermeshing with the rack 1040.

With the transmission 1022, the actuation of the trigger 1008 shall cause incremental displacement of the sheath 1020 only in one direction, either proximally or distally. The transmission 1022 must be adjusted, e.g., by adjusting the switching gear 1034, to cause displacement of the sheath 1020 in a reverse direction. With this arrangement, inadvertent "backing up" of the sheath 1020 may be avoided. Each actuation of the trigger 1008 will cause displacement in the same direction. Only adjustment of the transmission 1022 will permit reverse movement. Moreover, the intermeshing engagement between the pinion 1038 and the rack 1040 provides a fixed-state holding force for the sheath 1020 at a given position.

Figure 59:
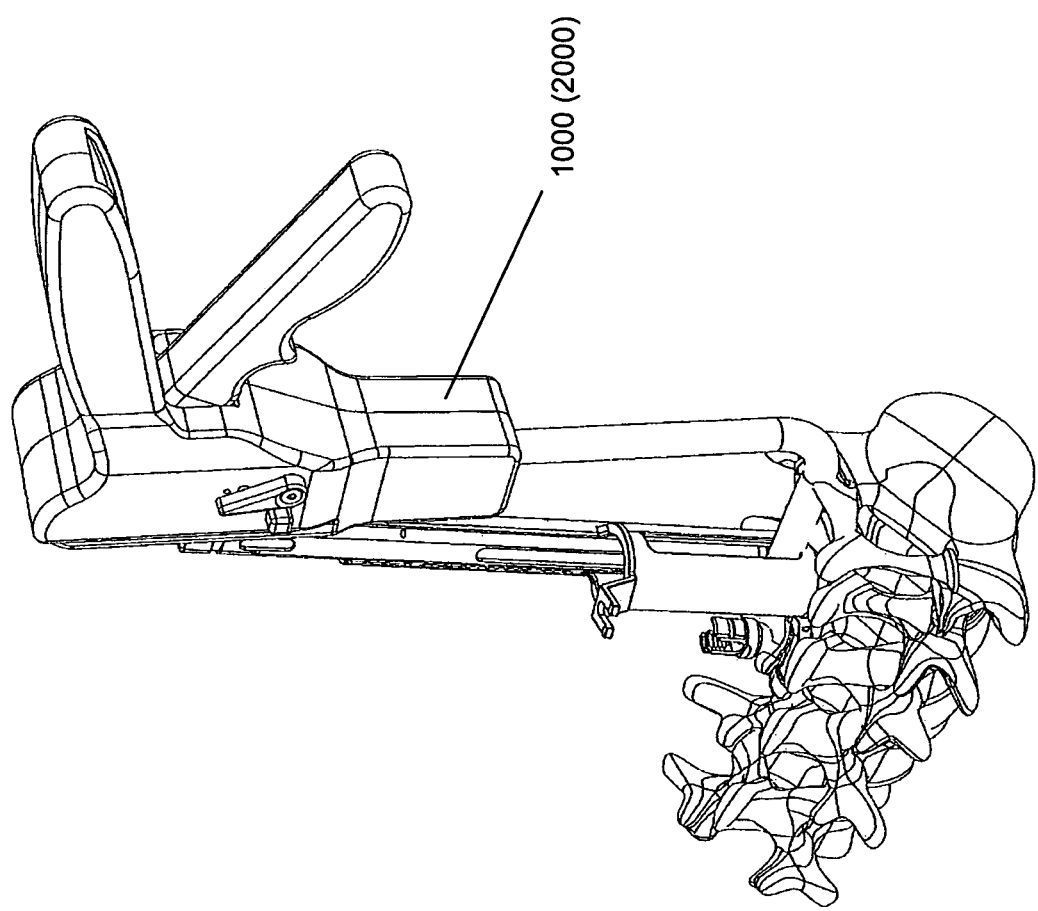
FIGS. 59-61 show the instrument and system in an implantation procedure.
Figure 60:
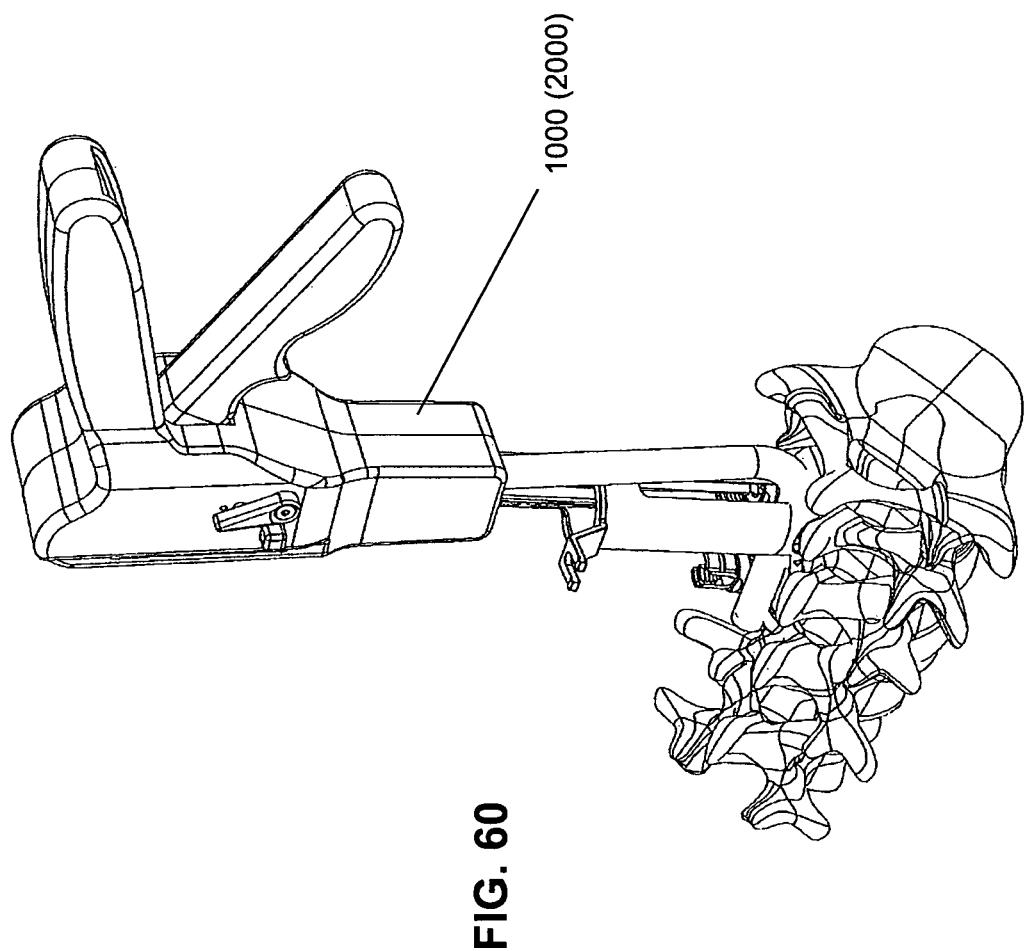
Figure 61:
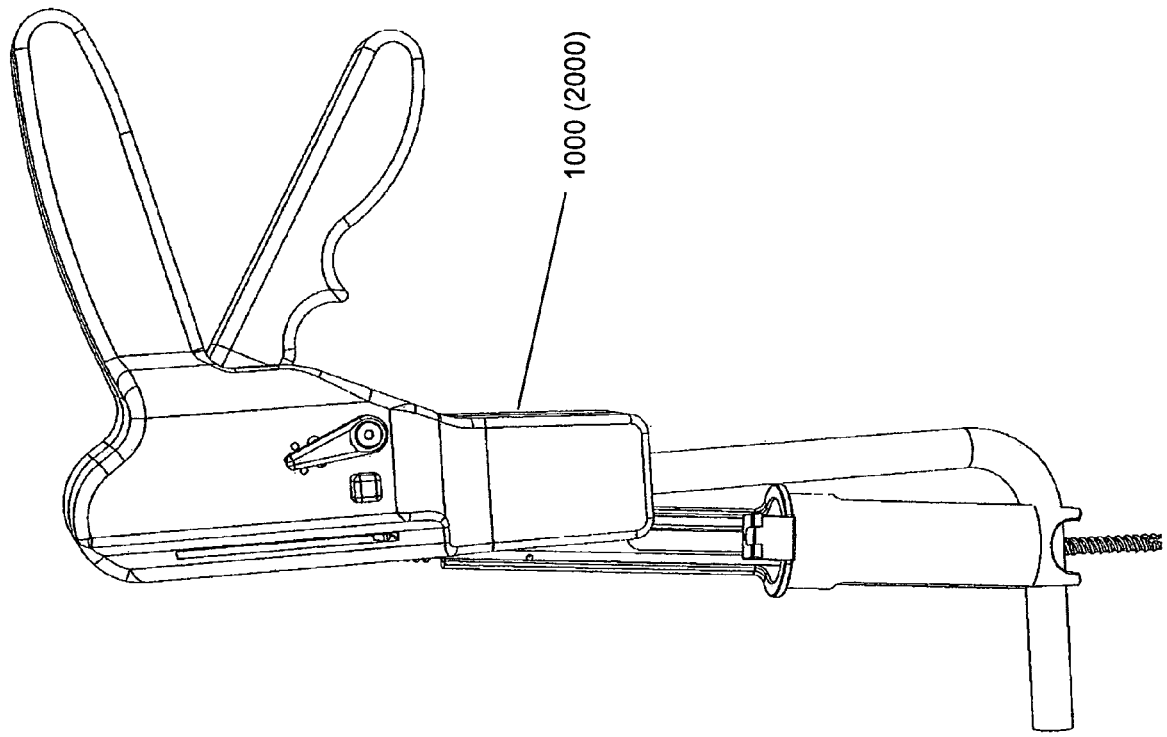
Figure 62:
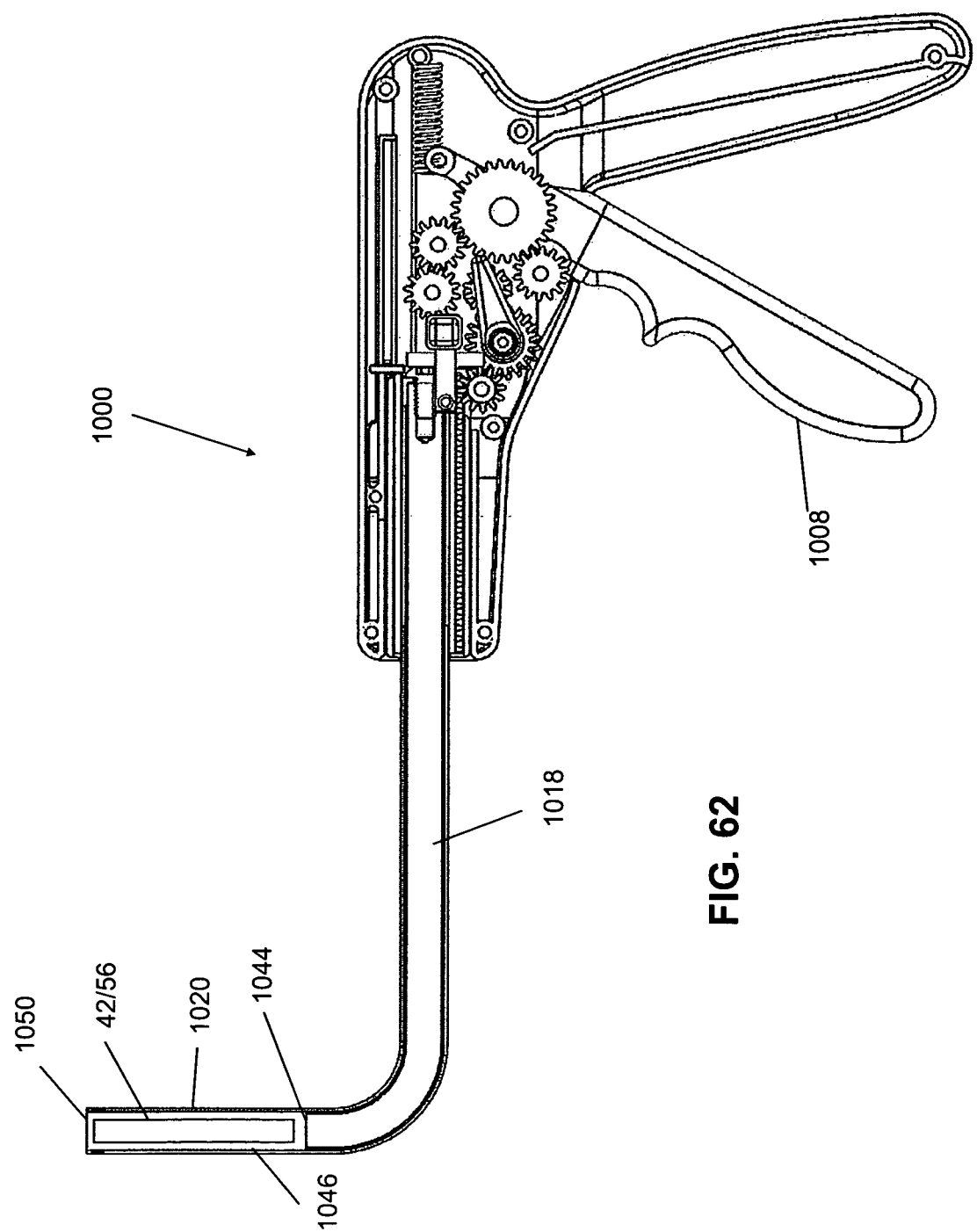
FIGS. 62-64 show proximal withdrawal of the sheath by the instrument in exposing a graft, implant and/or graft material.
Figure 63:
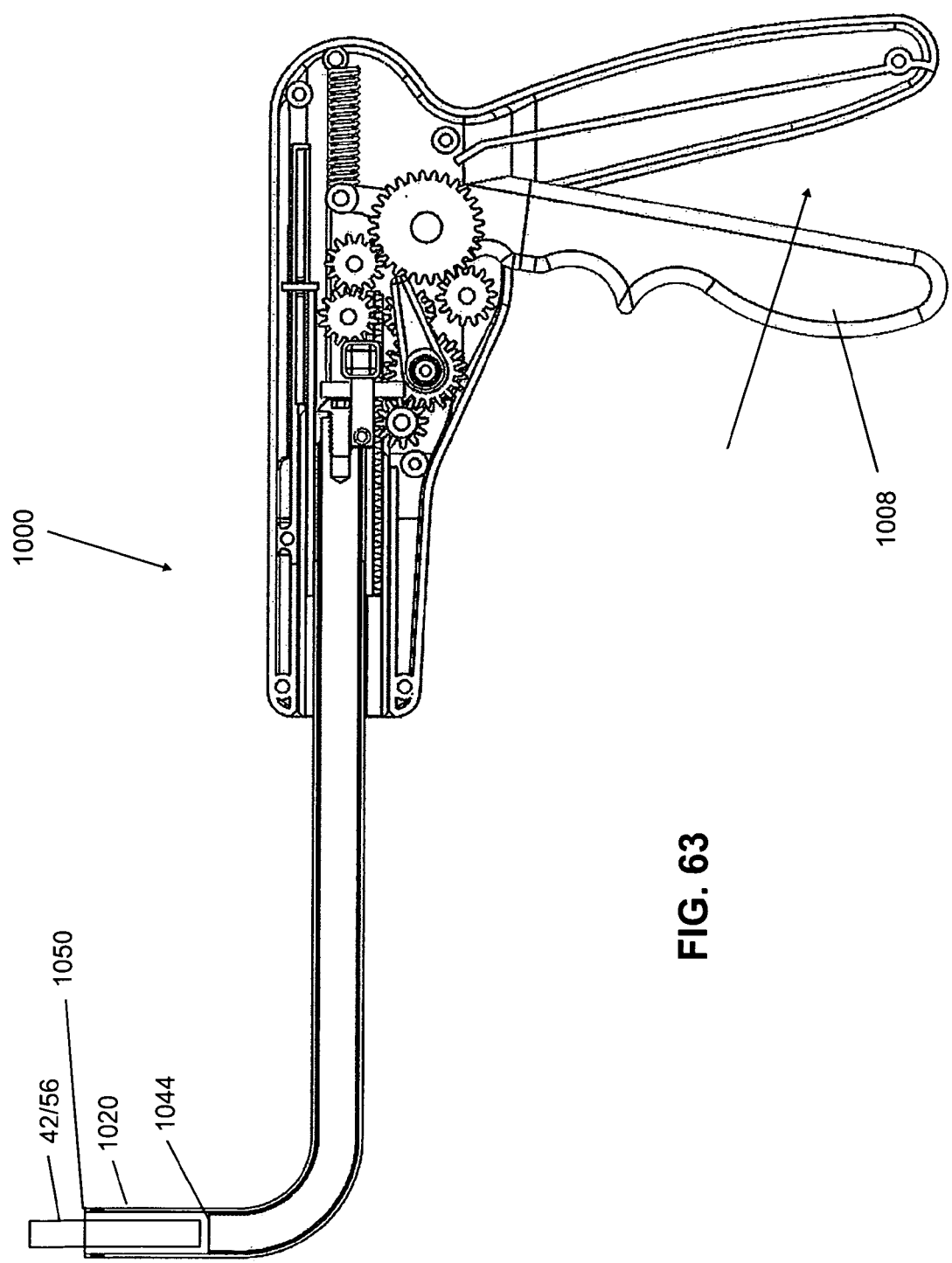
Figure 64:
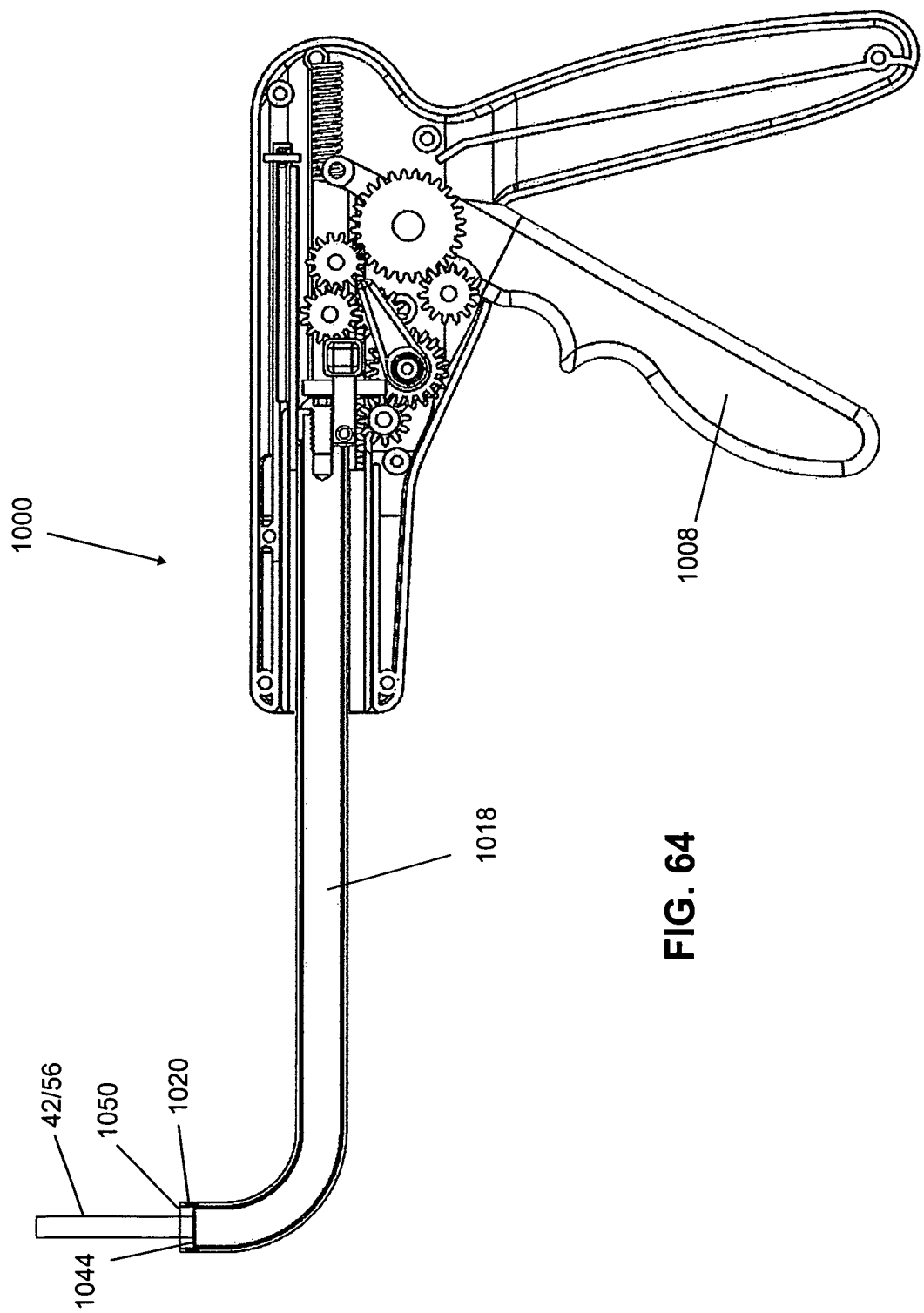

With reference to FIG. 62, in an initial state, the sheath 1020 extends distally past distal end 1044 of the access tube 1018. A space 1046 is defined within the sheath 1020 distally of the distal end 1044 which is sized to accommodate the perforated graft/tubular implant 42/56 and/or graft material. References herein to the "perforated graft/tubular implant 42/56" is to be understood to encompass not only grafts and implants but also graft material as well, such as flowable graft material. As shown at FIGS. 62-64, with actuations of the trigger 1008, the sheath 1020 may be caused to be incrementally displaced in a proximal direction relative to the distal end 1044 of the access tube 1018. With the access tube 1018 being stationary during movement of the sheath 1020, the perforated graft/tubular implant 42/56 is incrementally exposed with the proximal displacement of the sheath 1020. Thus, with the instrument 1000, as shown at FIGS. 59-61, the perforated graft/tubular implant 42/56 may be located at a target site while within the sheath 1020 and placed at the target site by actuations of the trigger 1008. One or more radiopaque markers 1048 (FIGS. 46 and 47) may be provided on the sheath 1020 to provide a surgeon with reference for proper locating. One of the radiopaque markers 1048 may be located at or adjacent to a distal end 1050 of the sheath 1020.

It is noted that during a procedure, a surgeon may require adjustment of the graft, implant and/or graft material during placement. The reversing of the transmission 1022, discussed above, allows for the surgeon to incrementally displace the sheath 1020 distally relative to the distal end 1044 of the access tube 1018, thereby causing the perforated graft/tubular implant 42/56 to be incrementally covered. This may allow for better adjustment during a procedure as needed.

To provide the surgeon with control over placement of the graft, implant, and/or graft material, as well as provide a tactile feel to the procedure, it is preferred that the actuation of the trigger 1008 result in a relatively small incremental displacement of the sheath 1020. The gear ratios of the transmission 1022 and the rack 1040 may be set as needed. Incremental displacements of the sheath 1020 per actuation of the trigger 1008 are desired on the order of 5-7 millimeters.

Figure 54:
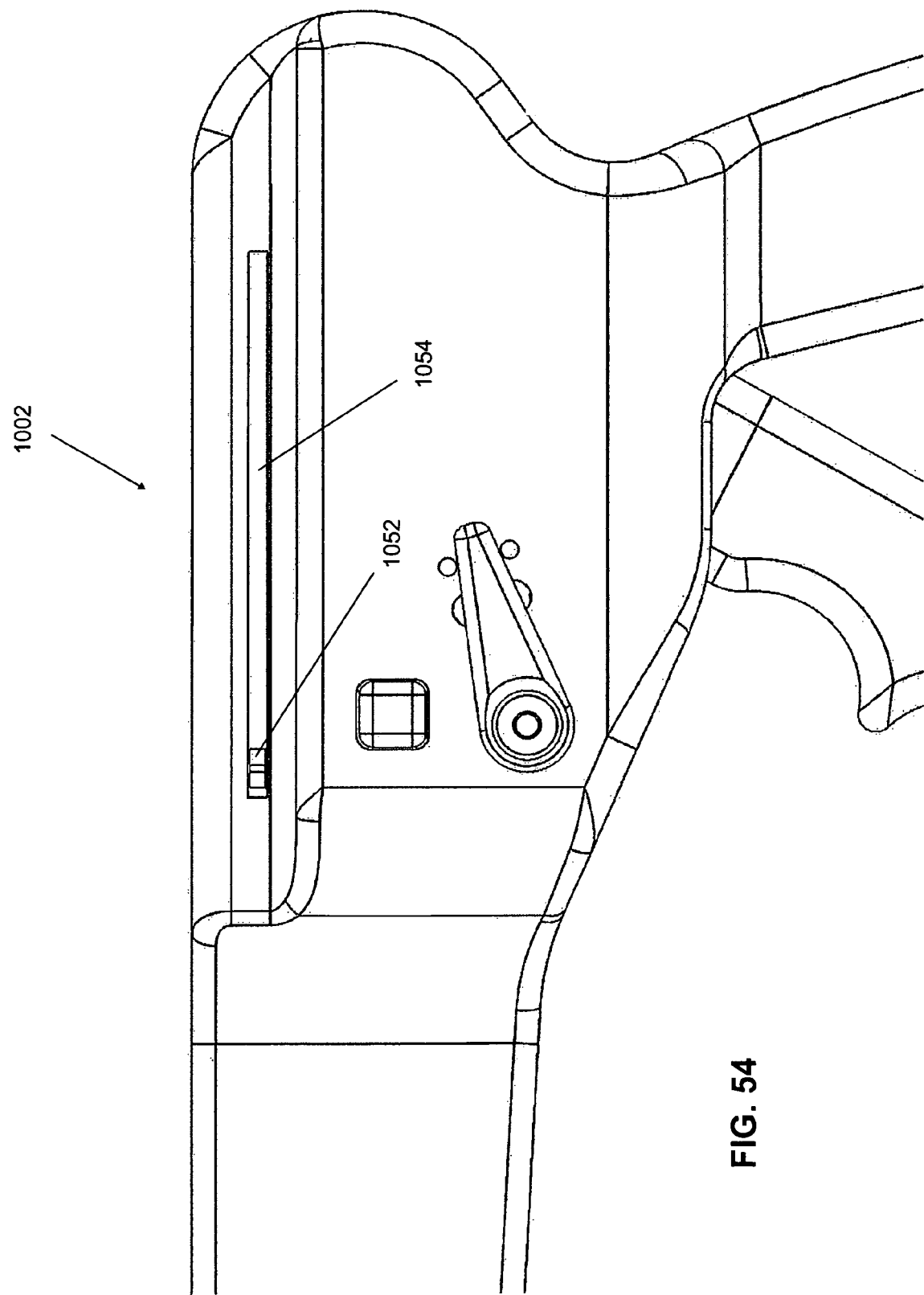
FIGS. 54-55 show a visual indicator provided with the instrument.
Figure 55:
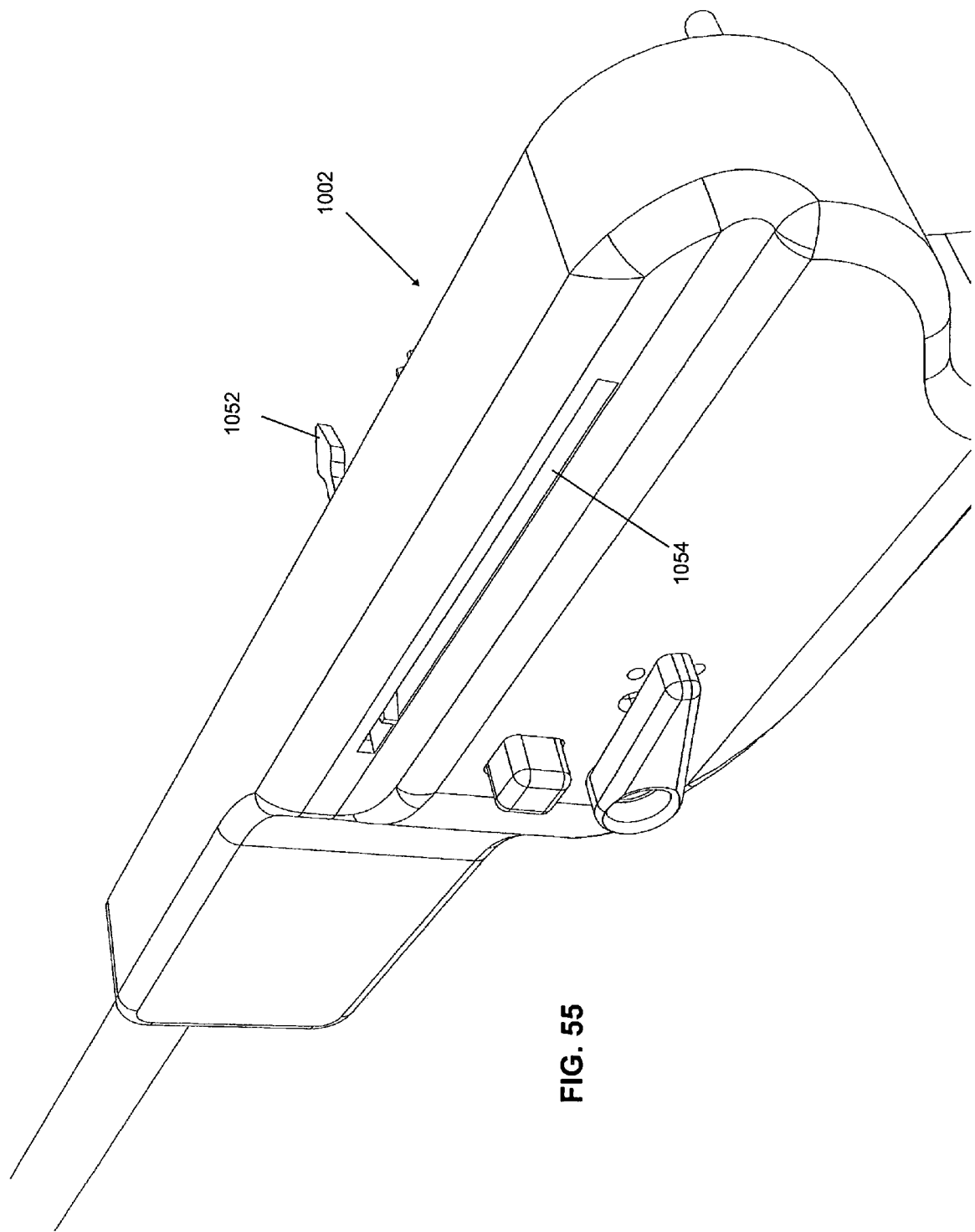

The instrument 1000 may be also provided with a visual indicator to represent actual proximal displacement of the sheath 1020 during a procedure. As shown at FIGS. 54-55, an indicator 1052 may be provided which is disposed to be viewable through one or more slots 154 provided on the housing 1002. A protrusion 1056 is fixed to the sheath 1020 so as to extend proximally therefrom. With reference to FIG. 57, with proximal displacement of the sheath 1020, the protrusion 1056 comes into engagement with the indicator 1052, thereby causing the indicator 1052 to shift proximally. This provides a visual indicator to the surgeon of the progress of the proximal withdrawal of the sheath 1020. With this arrangement, it is noted that distal displacement of the sheath 1020 will not cause adjustment of the indicator 1052.

The instrument 1000 may be provided with the access tube 1018 and the sheath 1020 being fixed thereto. To allow for better reusability of the instrument 1000, a system 2000 is provided, as shown on FIG. 45, which includes the instrument 1000 and a cartridge 2002 which is detachably mountable to the instrument 1000. The cartridge 2002 includes a body 2004 to which is fixed the access tube 1018. The sheath 1020 is provided with the cartridge 2002 and operates in the same manner relative to the access tube 1018 as described above. The detachable mounting of the cartridge 2002 allows for replacement of the cartridge 2002 as needed and preservation of the instrument 1000. The instrument 1000 may be sterilized and reset for each use, e.g., by placing the indicator 1052 to its starting position. The sheath 1020 may be provided with a graft, implant and/or graft material pre-packaged therein in sterile packaging, as part either of the instrument 1000 or the cartridge 2002, or the graft, implant and/or graft material may be loaded therein on-site.

Figure 51:
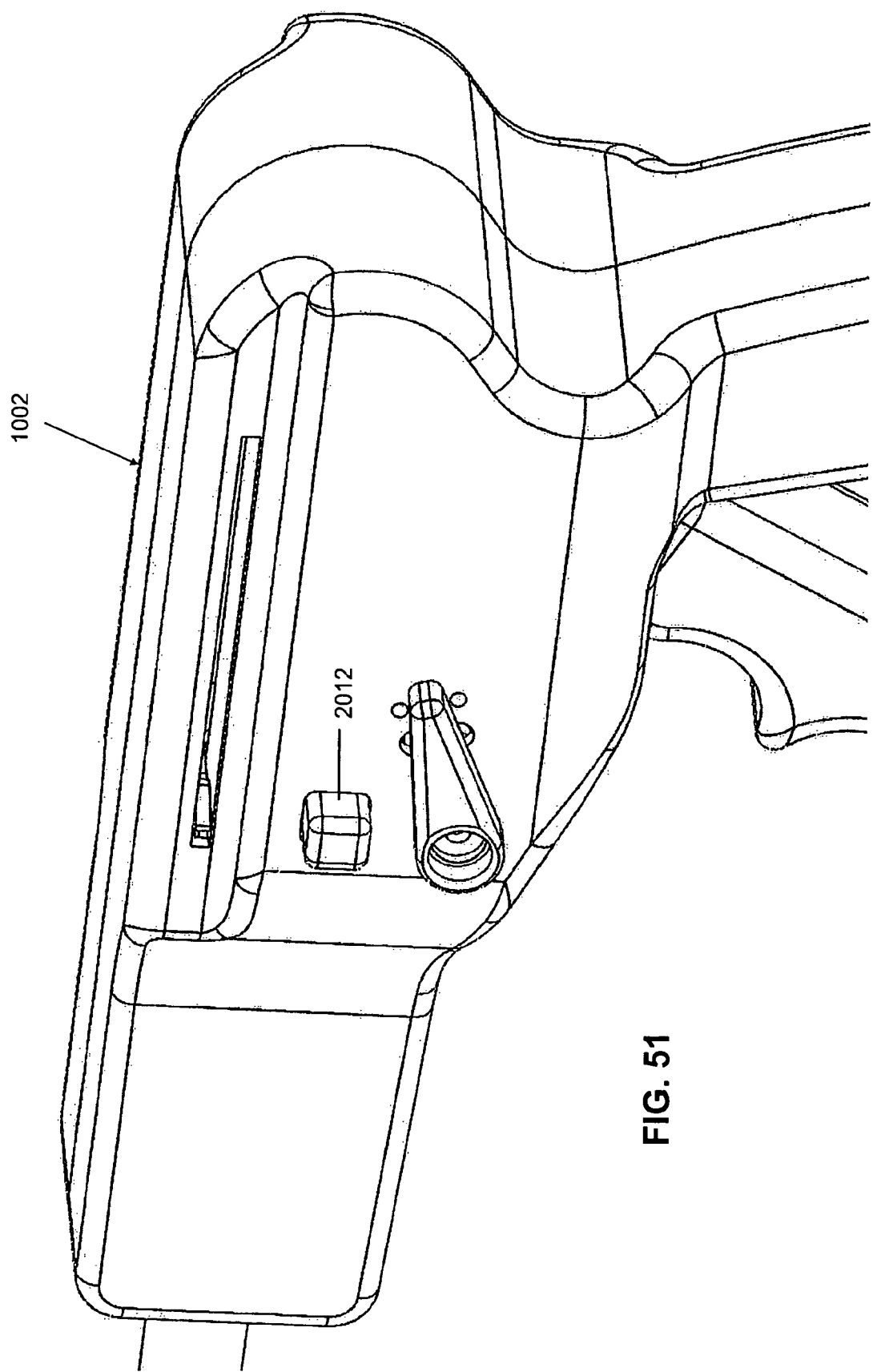
FIG. 51 shows the housing of the instrument.
Figure 52:
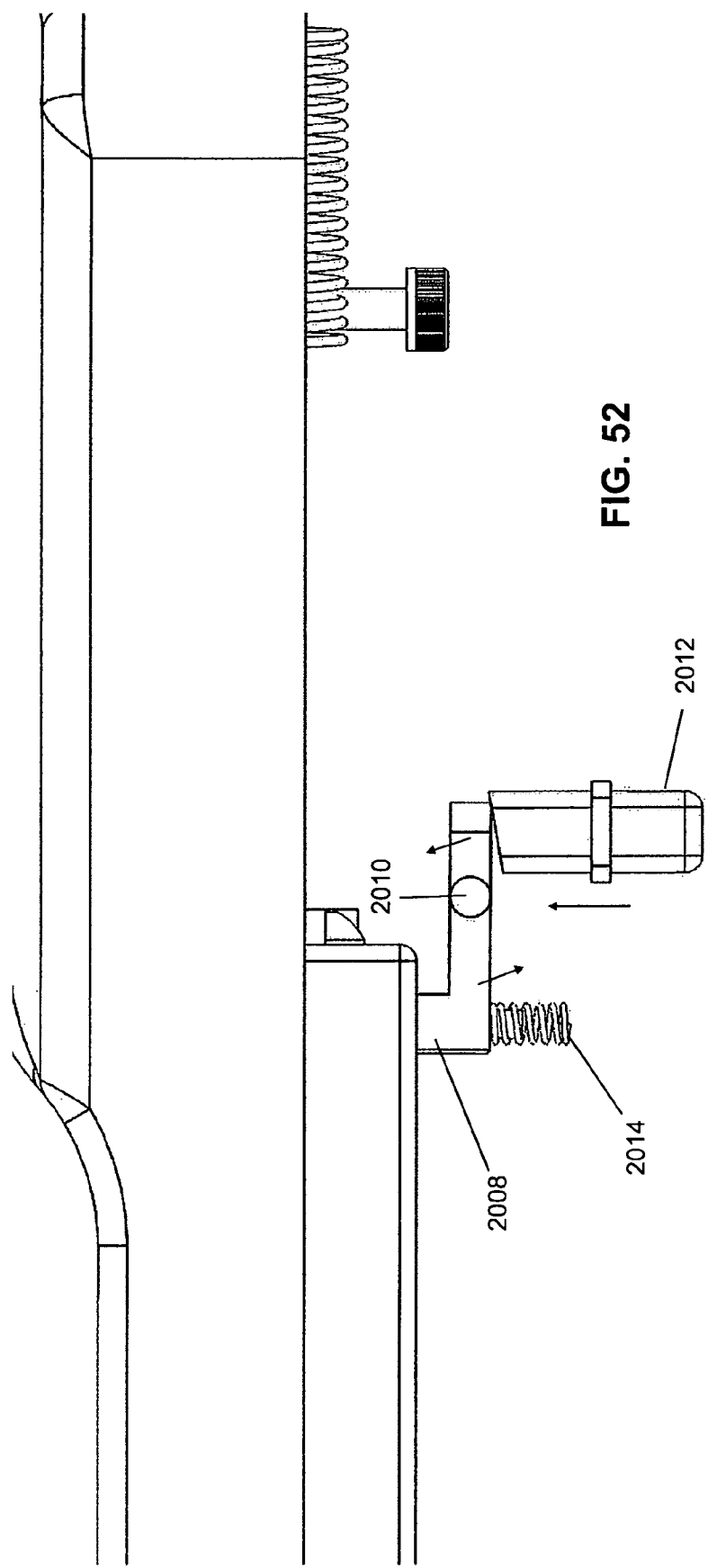
FIGS. 52-53 show an arrangement for detachably mounting the cartridge to the instrument.
Figure 53:
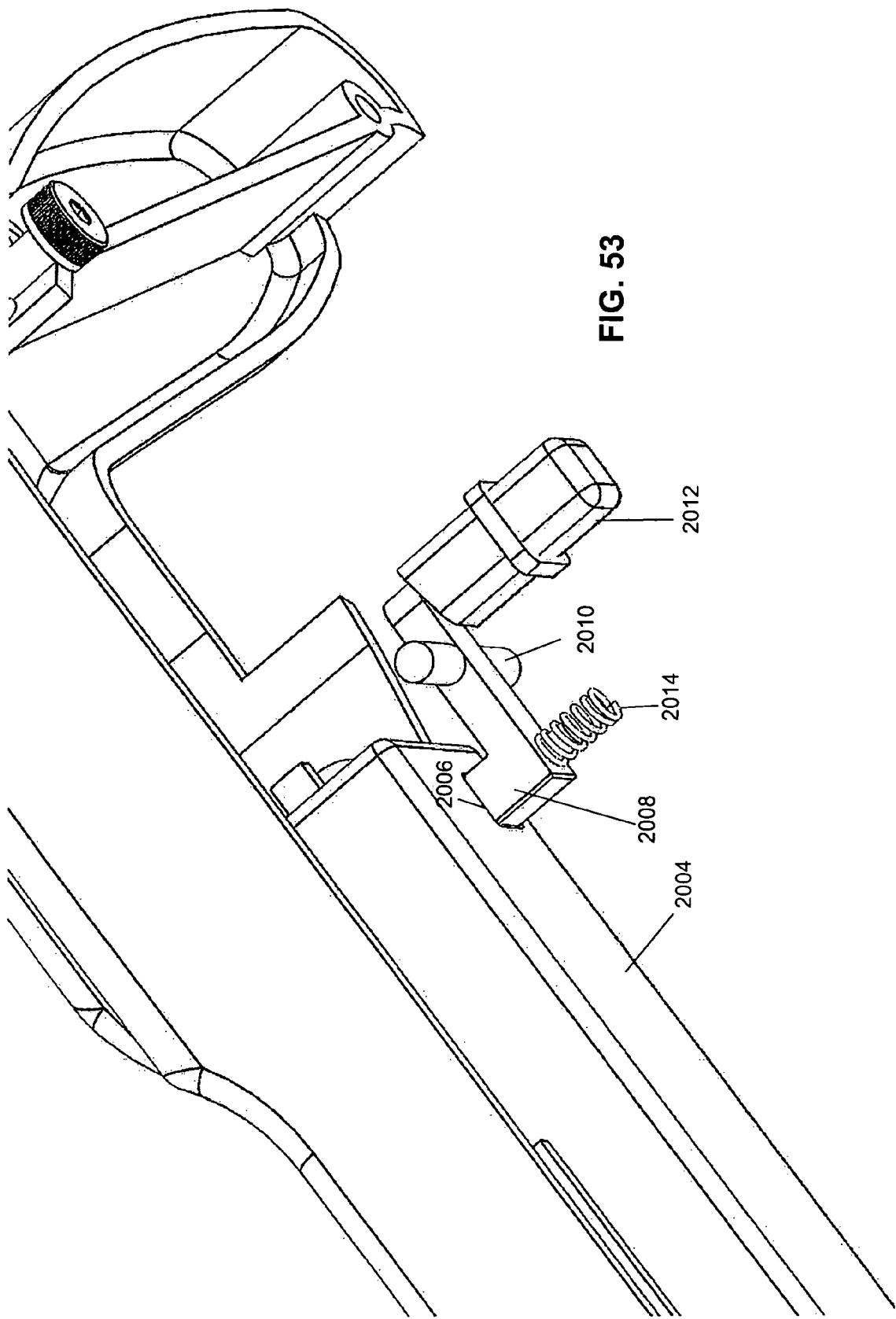
Figure 69:
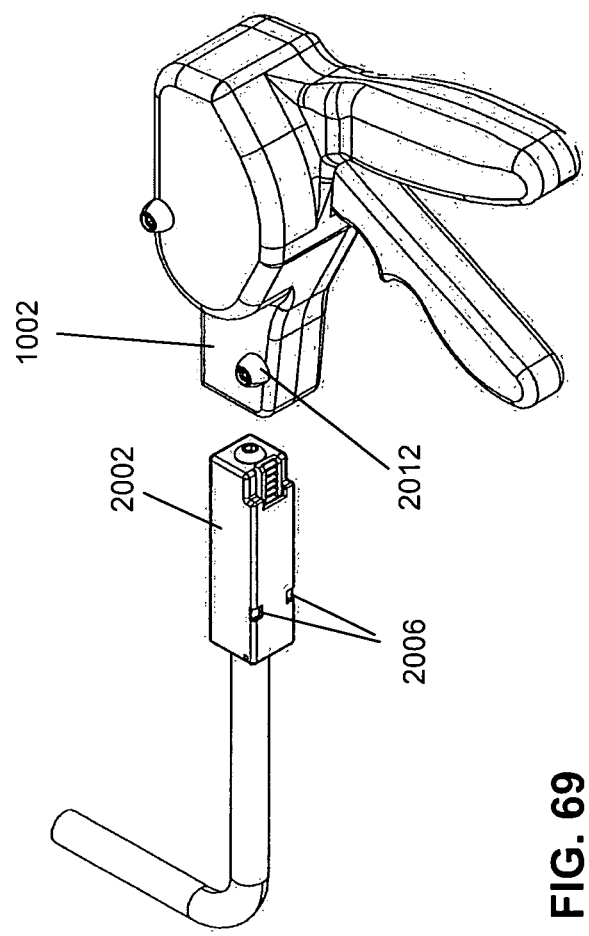
FIGS. 69-70 show an alternate arrangement for detachably mounting the cartridge to the instrument.
Figure 70:
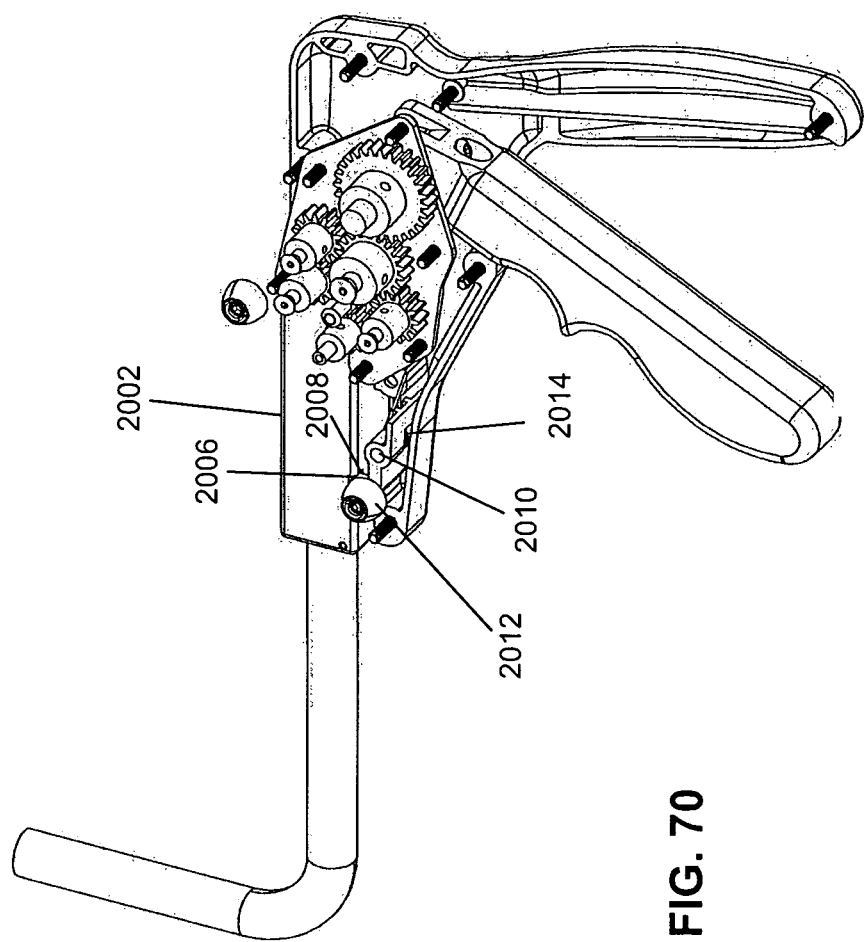
Figure 71:
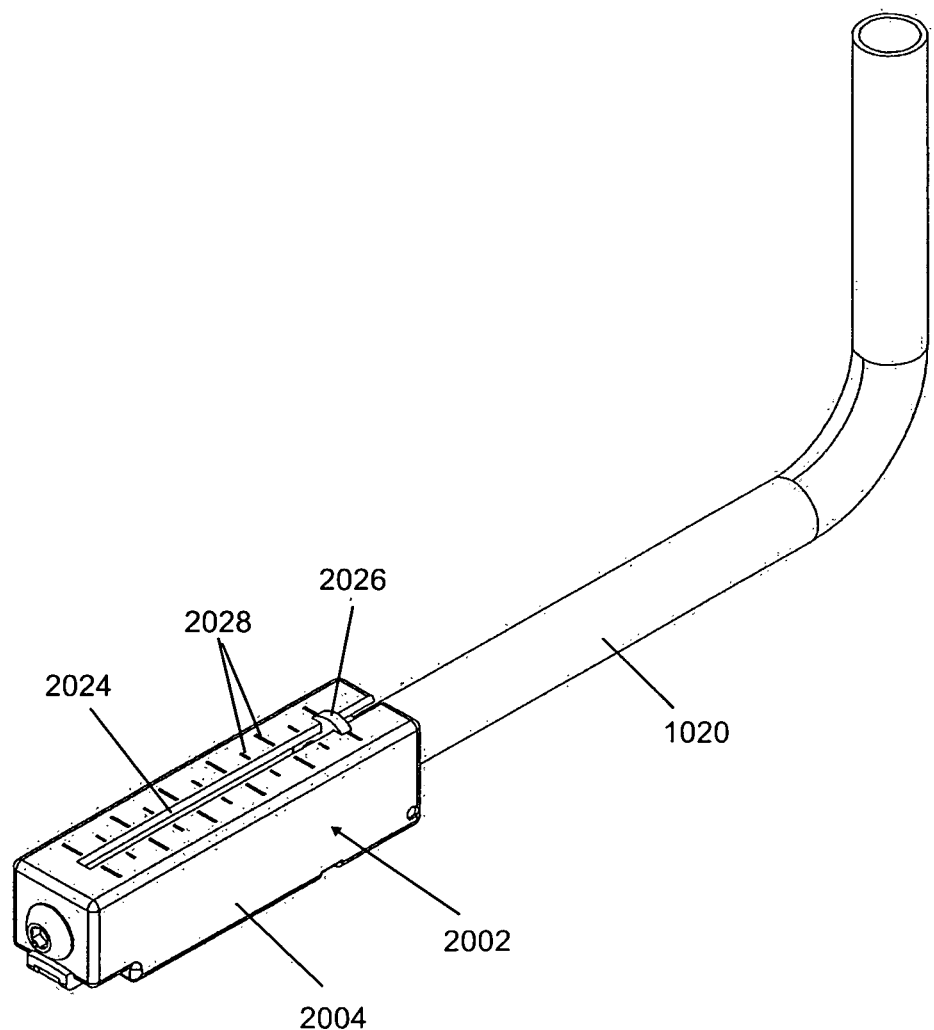
FIGS. 71-74 show a visual indicator provided with the cartridge.

The cartridge 2002 may be detachably mounted to the instrument 1000 in any known manner. By way of non-limiting example, a locking depression 2006, as shown in FIGS. 51-53, may be provided in the body 2004 which snap engages locking protrusion 2008, as shown in FIG. 53. The locking protrusion 2008 is pivotally fixed to the housing 1002 at fulcrum 2010 and includes button 2012 which extends out of the housing 1002, as shown at FIG. 51. The depression of the button 2012 causes outward displacement of the locking protrusion 2008 which facilitates attachment and detachment of the cartridge 2002. Spring 2014 may be provided which acts between the housing 1002 and the locking protrusion 2008 to provide additional holding force therefor. Alternatively, as shown in FIGS. 69-70, the button 2012 may be configured to be shiftable relative to the housing 1002, such as being reversibly upwardly and downwardly shiftable. The locking depression 2006 may be formed on an underside of the cartridge 2002. Shifting of the button 2012 results in outward displacement of the locking protrusion 2008 for release with the spring 2014 urging the locking protrusion 2008 towards the locked state.

Figure 49:
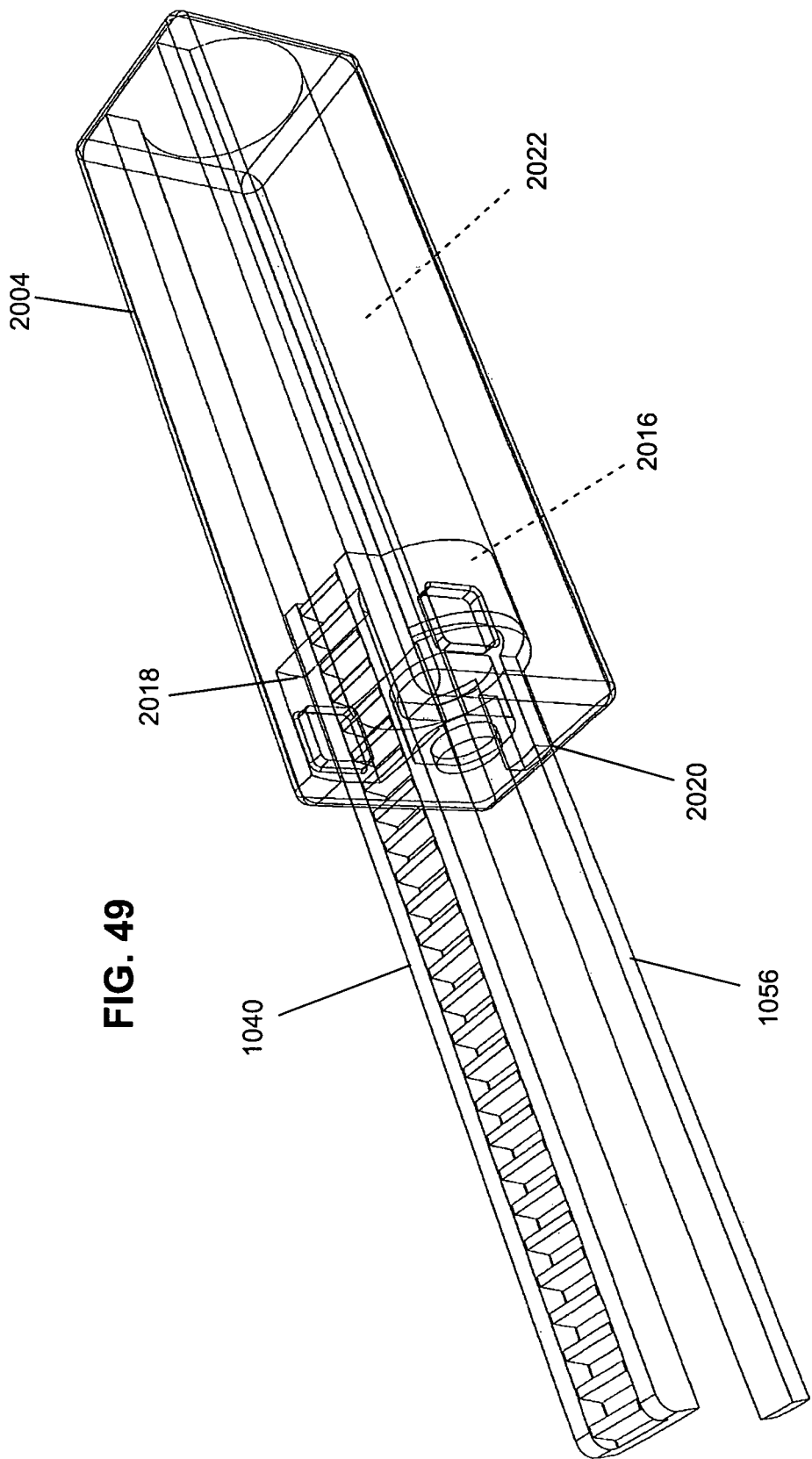
Figure 50:
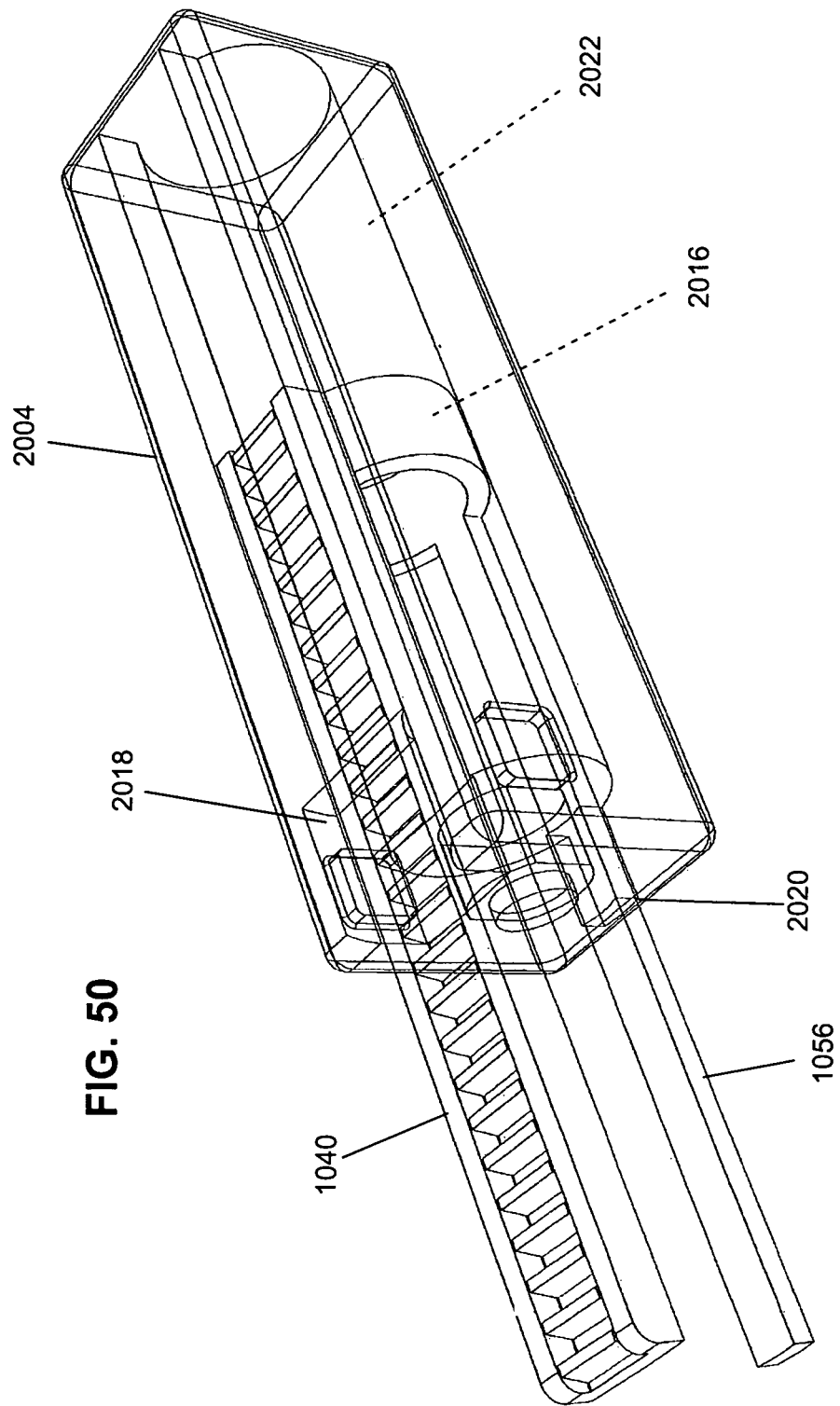

As shown at FIG. 47, a ring 2016 may be provided to which is secured the rack 1040 and the protrusion 1056. Corresponding openings 2018, 2020 are provided in the body 2004 through which the rack 1040 and the protrusion 1056 may extend and which allow for interengagement with the transmission 1022 and the indicator 1052, respectively. The body 2004 may be formed with a channel 2022 internally, as shown at FIG. 49, shaped to the profile of the ring 2016 to allow for guiding sliding movement through the body 2004.

Figure 72:
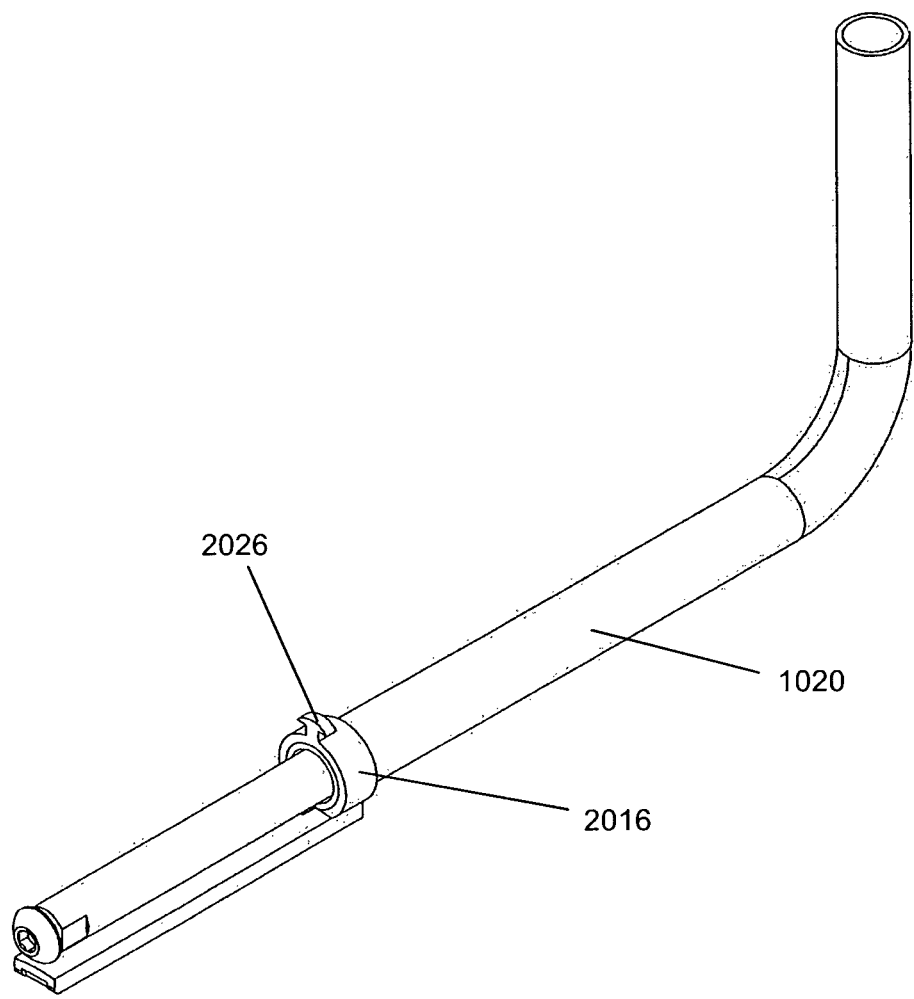
Figure 73:
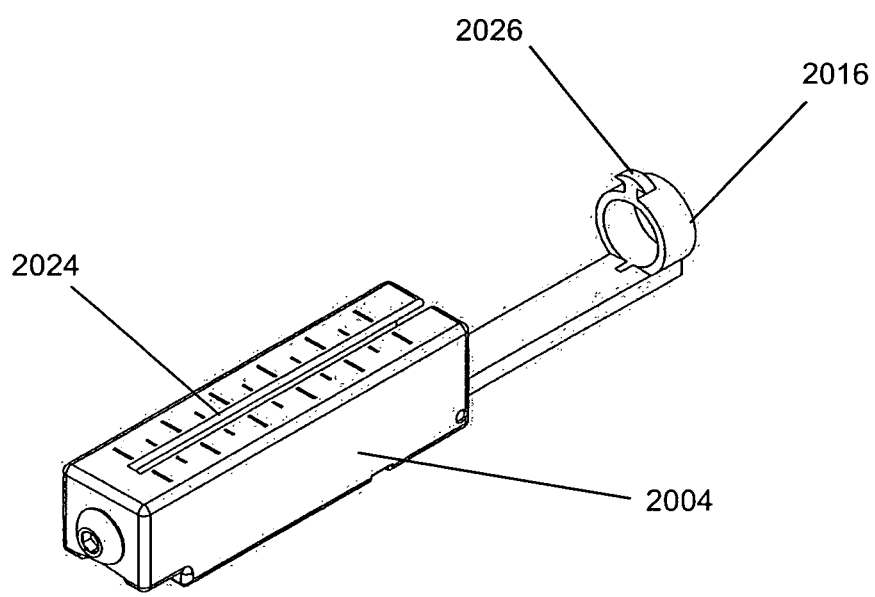
Figure 74:
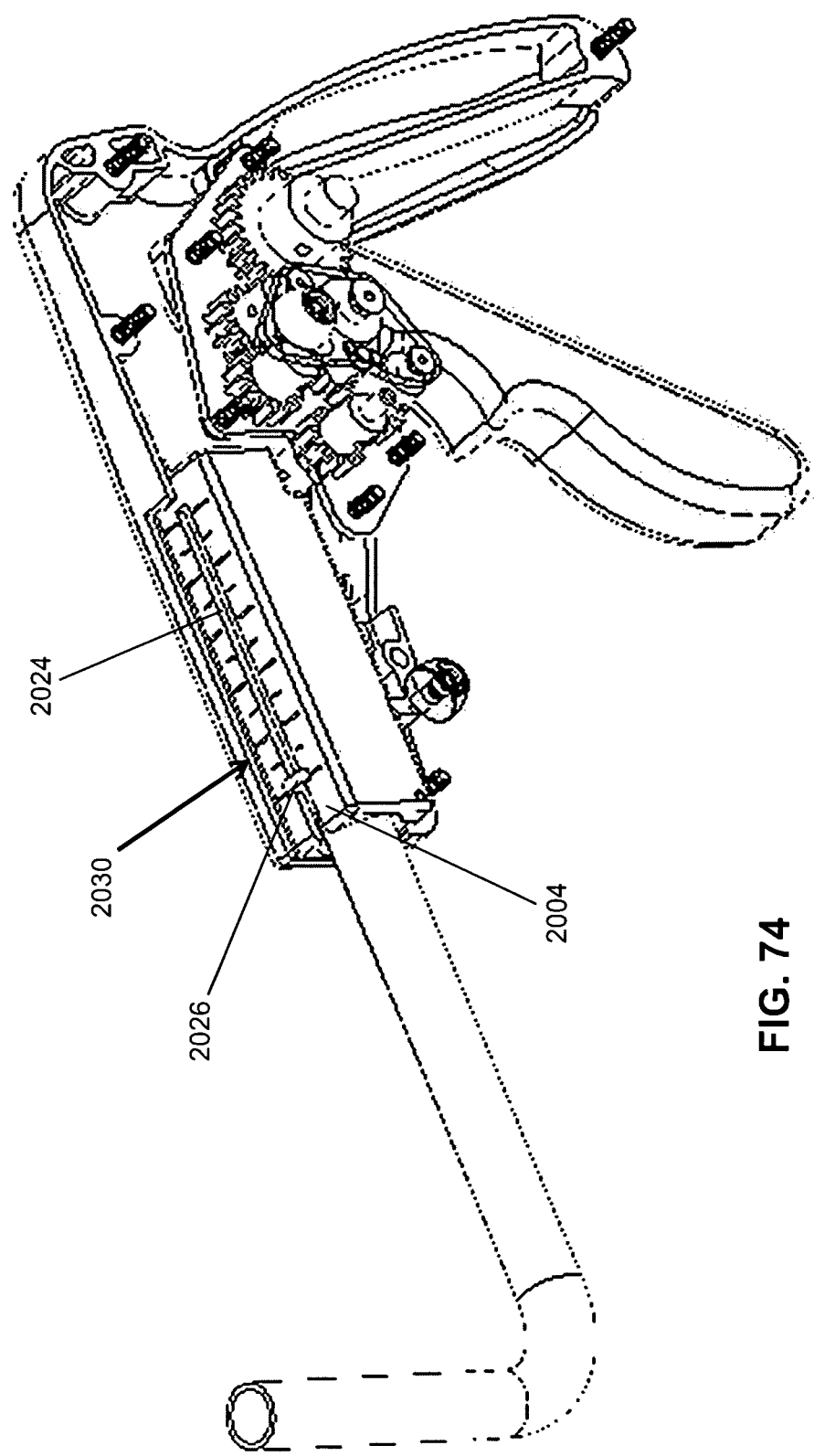

Optionally, a visual indicator may be provided with the cartridge 2002. With reference to FIGS. 71-74, the body 2004 may be provided with a slot 2024 through which indicator 2026 extends. The indicator 2026 is fixed to the sheath 1020 so as to move therewith. With the indicator 2026, proximal and distal displacement of the sheath 1020 may be visually monitored. Gradients 2028 or other markings may be provided on the body 2004 adjacent to the slot 2024 to provide reference points of displacement of the sheath 1020. The indicator 2026 may be fixed to the ring 2016, as shown in FIGS. 72-73. To allow for unobstructed viewing of the indicator 2026, a cut-out 2030 may be provided in the barrel portion 1004 of the housing 1002. The cut-out 2030 is preferable configured to expose the indicator 2026 with the cartridge 2002 mounted to the housing 1002.

As can be seen in FIGS. 59-61, the instrument 1000, alone or as part of the system 2000, in any manner described herein, is useable with the techniques described above for delivering the perforated graft/tubular implant 42/56 to a target site.

Having described the instrument 1000 and the system 2000 herein in a preferred arrangement for placing grafts, implants and/or graft material on transverse processes for posterolateral fusion, it should be appreciated that the instrument 1000 and the system 2000 may be used in other surgical applications. For example, the instrument 1000 and the system 2000 described herein may also be used in the placement of bone graft material in the intradiscal space between two opposing vertebrae in conjunction with a spinal intervertebral fusion implant in the intradiscal space.

What is claimed is:

1. An instrument for placing a graft, implant and/or graft material at a target site for enhancing posterolateral fusion between two or more vertebrae, the instrument comprising:
    a housing;
    an actuatable trigger associated with said housing;
    a rigid access tube having a fixed curve extending from said housing, said access tube terminating at a distal end;
    a sheath disposed about, and moveable relative to, said access tube; and,
    a transmission disposed in said housing,
    wherein, in an initial state, said sheath extends distally past said distal end of said access tube, a space being defined within said sheath distally of said distal end of said access tube to accommodate the graft, implant and/or graft material, and
    wherein, said transmission is configured to cause an incremental displacement of said sheath relative to said distal end of said access tube upon an actuation of said trigger.

2. An instrument as in claim 1, wherein said access tube is detachably mounted to said housing.

3. An instrument as in claim 1, further comprising a rack fixed to said sheath.

4. An instrument as in claim 3, wherein said transmission includes a pinion for intermeshing engagement with said rack.

5. An instrument as in claim 1, further comprising a protrusion fixed to said sheath.

6. An instrument as in claim 5, further comprising an indicator slidably mounted to said housing, said protrusion being located to engage said indicator with proximal displacement of said sheath.

7. An instrument as in claim 1, wherein at least one radiopaque marker is provided on said sheath.

8. An instrument as in claim 1, where said transmission is adjustable to selectively permit proximal and distal displacement of said sheath relative to said distal end of said access tube.

9. An implantation system comprising;
    an instrument as in claim 1; and,
    a graft, implant and/or graft material disposed within said space, said graft, implant and/or graft material configured to enhance posterolateral fusion between two or more vertebrae.

10. A system for placing a graft, implant and/or graft material at a target site for enhancing fusion between two or more vertebrae, the system comprising:
    an instrument including:
        a housing;
        an actuatable trigger associated with said housing; and,
        a transmission,
    and,
    a cartridge detachably mountable to said instrument, said cartridge including:
        a body;
        a rigid access tube having a fixed curve fixed to said body, said access tube terminating at a distal end;
        a sheath disposed about, and moveable relative to, said access tube,
    wherein, with said cartridge mounted to said instrument, said transmission being configured to cause an incremental displacement of said sheath relative to said distal end of said access tube upon an actuation of said trigger.

11. A system as in claim 10, wherein, in an initial state, said sheath extends distally past said distal end of said access tube, a space being defined within said sheath distally of said distal end of said access tube to accommodate the graft, implant and/or graft material.

12. A system as in claim 10, wherein said cartridge further including a rack fixed to said sheath.

13. A system as in claim 12, wherein said transmission includes a pinion for intermeshing engagement with said rack.

14. A system as in claim 10, wherein said cartridge further including a protrusion fixed to said sheath.

15. A system as in claim 14, wherein said instrument further including an indicator slidably mounted to said housing, said protrusion being located to engage said indicator with proximal displacement of said sheath.

16. A system as in claim 10, wherein at least one radiopaque marker is provided on said sheath.

17. A system as in claim 10, wherein said transmission is adjustable to selectively permit proximal and distal displacement of said sheath relative to said distal end of said access tube.

18. A system as in claim 10, wherein an indicator is fixed to said sheath so as to move therewith, said indicator extending through a slot formed in said body.

19. An implantation system comprising:
    a system as in claim 11; and,
    a graft, implant and/or graft material disposed within said space, said graft, implant and/or graft material configured to enhance posterolateral fusion between two or more vertebrae.

20. An implantation system comprising:
    a system as in claim 11; and,
    a graft material disposed within said space, said graft material configured for placement in the intradiscal between two opposing vertebrae to enhance fusion between said vertebrae in conjunction with a spinal intervertebral fusion implant in said intradiscal space.

* * * * *